United States Patent
Qian et al.

(10) Patent No.: US 10,725,053 B2
(45) Date of Patent: Jul. 28, 2020

(54) PROSTATE CANCER-ASSOCIATED SECRETED PROTEINS

(71) Applicants: Battelle Memorial Institute, Richland, WA (US); University of Washington, Seattle, WA (US)

(72) Inventors: Wei-Jun Qian, Richland, WA (US); Tujin Shi, Richland, WA (US); Alvin Y. Liu, Everett, WA (US)

(73) Assignees: Battelle Memorial Institute, Richland, WA (US); University of Washington, Seattle, WA (US)

( * ) Notice: Subject to any disclaimer, the term of this patent is extended or adjusted under 35 U.S.C. 154(b) by 0 days.

(21) Appl. No.: 15/839,635

(22) Filed: Dec. 12, 2017

(65) Prior Publication Data

US 2018/0164329 A1    Jun. 14, 2018

Related U.S. Application Data

(60) Provisional application No. 62/432,946, filed on Dec. 12, 2016.

(51) Int. Cl.
```
G01N 33/574      (2006.01)
G01N 33/68       (2006.01)
C12Q 1/37        (2006.01)
C12Q 1/533       (2006.01)
```

(52) U.S. Cl.
CPC ........... *G01N 33/6893* (2013.01); *C12Q 1/37* (2013.01); *C12Q 1/533* (2013.01); *C12Y 304/24035* (2013.01); *C12Y 503/04001* (2013.01); *G01N 33/57434* (2013.01); *G01N 33/6848* (2013.01); *G01N 33/6863* (2013.01); *G01N 33/6869* (2013.01); *G01N 2333/47* (2013.01); *G01N 2333/52* (2013.01); *G01N 2333/54* (2013.01); *G01N 2333/70503* (2013.01); *G01N 2333/70596* (2013.01); *G01N 2333/96486* (2013.01); *G01N 2333/99* (2013.01)

(58) Field of Classification Search
None
See application file for complete search history.

(56) References Cited

U.S. PATENT DOCUMENTS

| | | | |
|---|---|---|---|
| 9,091,651 B2 * | 7/2015 | Kearney | G01N 33/6848 |
| 2013/0203096 A1 | 8/2013 | Kearney et al. | |
| 2014/0194304 A1 | 7/2014 | Shi et al. | |

OTHER PUBLICATIONS

Duncan et al (Eur. J. Biochem, 1998, 258:37-43).*
Oguic et al (Pathology Research International, 2014, Article ID 262195, 8 pages).*
Sauer et al (Virchows Arch, 2004, 444:518-526).*
Roy et al (Clinical Cancer Research, 2008, 14:6610-6617).*
Moses et al (Cancer Research, 1998, 58:1395-1399).*
Van Gils et al (European Urology, 2005, 48:1031-1041).*
Principe et al (Journal of Proteome Research, 2012, 11:2386-2396).*
Principe et al (Journal of Proteome Research, 2012) Supplementary Information Table 1, p. 18 only.*
Wallace et al (Journal of Cancer, 2014, 5:3-24).*
Wilhem et al (Journal of Biological Chemistry, 1989, 264:17213-17221).*
NCBI Reference Sequence: NP_004985.2 (printed Nov. 2019).*
UniProtKB/Swiss-Prot: P14780.3 (printed Nov. 2019).*
Yocum et al (Proteomics, 2010, 10:3506-3514).*
Vegvari et al (Molecular and Cellular Proteomics, 2013, 12:2761-2773).*
Bolduc, et al., "Urinary PSA: a potential useful marker when serum PSA is between 2.5 ng/mL and 10 ng/mL." *Canadian Urological Association Journal*, vol. 1(4): 377-381 (2007).
Keshishian et al., "Quantitative, multiplexed assays for low abundance proteins in plasma by targeted mass spectrometry and stable isotope dilution." *Molecular & Cellular Proteomics*, vol. 6(12): 2212-2229 (2007).
Marks et al., "Prostate cancer specificity of PCA3 gene testing: examples from clinical practice." *Reviews in Urology*, vol. 10(3): 175-181 (2008).
Mikolajczyk et al.,"Free prostate-specific antigen in serum is becoming more complex." *Urology*, vol. 59(6): 797-802 (2002).
Nakanishi, et al. "PCA3 molecular urine assay correlates with prostate cancer tumor volume: implication in selecting candidates for active surveillance." *The Journal of Urology*, vol. 179(5): 1804-1810 (2008).
Pascal et al., "Gene expression relationship between prostate cancer cells of Gleason 3, 4 and normal epithelial cells as revealed by cell type-specific transcriptames." *BMC Cancer*, vol. 9(1): 452 (2009).
Quek et al., "Processing of voided urine for prostate cancer RNA biomarker analysis." *The Prostate*, vol. 75(16): 1886-1895 (2015).
Shi et al.,"A highly sensitive targeted mass spectrometric assay for quantification of AGR2 protein in human urine and serum." *Journal of Proteome Research*, vol. 13(2): 875-882 (2014).
Shi et al.,"Antibody-free, targeted mass-spectrometric approach for quantification of proteins at low picogram per milliliter levels in human plasma/serum." *Proceedings of the National Academy of Sciences*, vol. 109(38): 15395-15400 (2012).

(Continued)

*Primary Examiner* — Laura B Goddard
(74) *Attorney, Agent, or Firm* — Klarquist Sparkman, LLP

(57) ABSTRACT

Methods are provided for treating a subject with prostate cancer and/or diagnosing a subject at risk for prostate cancer, which can include measuring increased expression of at least two prostate cancer-related molecules in a sample obtained from a subject, including the prostate cancer-related molecules AGR2, AGR3, CRISP3, CCL3, CEACAM5, CEACAM6, IL24, MMP9, CXCL14, CD90, POSTN, and SFRP4. The methods can include administering at therapy to a subject with prostate cancer. Methods are provided for treating a subject with intermediate- or high-risk prostate cancer, which can include measuring increased expression of MMP9 in a sample obtained from a subject compared to a control representing expression of MMP9 expected in a sample from a subject who has low-risk prostate cancer.

17 Claims, 29 Drawing Sheets

Specification includes a Sequence Listing.

(56) References Cited

OTHER PUBLICATIONS

Shi et al., "Long-gradient separations coupled with selected reaction monitoring for highly sensitive, large scale targeted protein quantification in a single analysis." *Analytical Chemistry*, vol. 85(19): 9196-9203 (2013).
Shi et al., "Multiplexed targeted mass spectrometry assays for prostate cancer-associated urinary proteins." *Oncotarget*, vol. 8(60): 101887-101898 (2017).
Shi et al.,"Targeted quantification of low ng/mL level proteins in human serum without immunoaffinity depletion." *Journal of Proteome Research*, vol. 12(7): 3353-3361 (2013).
Végvári et al., "Identification of a novel proteoform of prostate specific antigen (SNP-L132I) in clinical samples by multiple reaction monitoring." *Molecular & Cellular Proteomics: MCP*, vol. 12(10): 2761-2773 (2013).
Wayner et al., "Development of an ELISA to detect the secreted prostate cancer bimmarker AGR2 in voided urine," *The Prostate*, vol. 72(9): 1023-1034 (2012).
Worboys et al., "Systematic evaluation of quantotypic peptides for targeted analysis of the human kinome." *Nature Methods*, vol. 11(10): 1041-1044 (2014).
Zhang et al., "Serum proteomics reveals systemic dysregulation of innate immunity in type 1 diabetes." *Journal of Experimental Medicine*, vol. 210(1): 191-203 (2013).

* cited by examiner

FIG. 1

| UrinePA n=2,500 non-redundant proteins (5 labs) urinary core proteome n=587 | | | |
|---|---|---|---|
| | identifiers | builds | observed |
| UMOD | 15 | 3 | 24,115 |
| ALB | 18 | 3 | 33,149 |
| LGALS3 (Mac-2) | 4 | 3 | 133 |
| APOD | 7 | 3 | 2,352 |
| LMAN2 (VIP36) | 10 | 3 | 639 |
| AMBP | 3 | 3 | 15,223 |
| F2 (thrombin) | 7 | 3 | 1,164 |
| PTGDS (prostaglandin h2 isomerase) | 12 | 3 | 4,479 |
| IGHG1 | 17 | 3 | 6,381 |
| LCN2 | 6 | 3 | 189 |
| KLK3 | 9 | 3 | 193 |
| KLK2 | 6 | 3 | 2 |
| MSMB | 3 | 3 | 21 |
| ACPP | 8 | 3 | 415 |
| AZGP1 | 8 | 3 | 1,903 |
| PSCA | 3 | 3 | 123 |
| PRSS8 (prostasin) | 7 | 3 | 230 |
| TMPRSS2 | 10 | 3 | 17 |
| ERG | 0 | 0 | 0 |
| FOLH1 (PSMA) | 0 | 0 | 0 |
| PENK | 5 | 3 | 6 |
| UPK3A | 2 | 3 | 3 |

| | identifiers | builds | observed |
|---|---|---|---|
| AGR2 | 0 | 0 | 0 |
| AGR3 | 0 | 0 | 0 |
| CRISP3 | 8 | 3 | 65 |
| CEACAM5 | 6 | 3 | 21 |
| CEACAM6 | 2 | 3 | 5 |
| CCL3 | 0 | 0 | 0 |
| CCL4 | 0 | 0 | 0 |
| CD24 | 0 | 0 | 0 |
| IL24 | 0 | 0 | 0 |
| THY1 (vs. CD90v) | 7 | 3 | 261 |
| POSTN | 0 | 0 | 0 |
| MMP9 | 3 | 3 | 115 |
| SFRP4 | 3 | 3 | 17 |
| CXCL14 | 0 | 0 | 0 |
| WISP1 | 0 | 0 | 0 |

| | identifiers | builds | observed |
|---|---|---|---|
| DPP4 (CD26) | 6 | 3 | 1,510 |
| MME (CD10) | 13 | 3 | 98 |
| CD59 | 10 | 3 | 311 |
| CD44 | 53 | 3 | 831 |
| PTPRC (CD45) | 0 | 0 | 0 |
| PECAM1 (CD31) | 7 | 3 | 9 |
| B3GAT1 (CD57) | 0 | 0 | 0 |
| CD38 | 0 | 0 | 0 |
| LAMP1 (CD107a) | 5 | 3 | 121 |
| LAMP2 (CD107b) | 10 | 3 | 321 |
| LAMP3 (CD63) | 4 | 3 | 1 |

FIG. 2

| Gene | Protein | Accession number | Selected surrogate Peptide | Best surrogated peptide[a] | SRM transitions | | | |
|---|---|---|---|---|---|---|---|---|
| | | | | | Q1 | | Q3 | |
| AGR3 | AGR3 | Q8TD06 | LYTYEPR | LYTYEPR | 471.2 | 685.3 | 272.2 | 277.2 |
| | | | NLSPDGQYVPR | | | | | |
| | | | VFAQNEEIQEMAQNK | | | | | |
| | | | RPPQTLSR | | | | | |
| CCL3 | CCL3 | P10147 | QVCADPSEEWVQK[b] | QVCADPSEEWVQK[b] | 788.4 | 1188.6 | 1117.5 | 1002.5 |
| | | | QIPQNFIADYFETSSQCSK[b] | | | | | |
| | | | YVSDLELSA | | | | | |
| CCL4 | CCL4 | P13236 | NFVVDYYETSSLCSQPAVVFQTK[b] | | | | | |
| | | | APMGSDPPTACCFSYTAR[b] | | | | | |
| | | | QVCADPSESWVQEYVYDLELN[b] | | | | | |
| CEACAM5 | CEAM5 | P06731 | INGIPQQHTQVLFIAK | INGIPQQHTQVLFIAK | 603.0 | 847.5 | 761.9 | 705.4 |
| | | | SDLVNEEATGQFR | SDLVNEEATGQFR | 733.3 | 1051.5 | 937.4 | 679.4 |
| | | | CETQNPVSAR[b] | CETQNPVSAR[b] | 581.3 | 872.5 | 643.4 | 529.3 |
| | | | AYVCGIQNSVSANR[b] | | | | | |
| CEACAM6 | CEAM6 | P40199 | EVLLLAHNLPQNR | EVLLLAHNLPQNR | 508.3 | 741.4 | 514.3 | 531.8 |
| | | | SDPVTLNVLYGPDGPTISPSK | SDPVTLNVLYGPDGPTISPSK | 1079.1 | 1055.5 | 998.5 | 331.2 |
| | | | NDAGSYECEIQNPASANR[b] | | | | | |
| CRISP3 | CRISP3 | P54108 | WANQCNYR[b] | WANQCNYR[b] | 556.2 | 925.4 | 854.4 | 612.3 |
| | | | YEDLYSNCK[b] | YEDLYSNCK[b] | 596.3 | 899.4 | 784.4 | 671.3 |
| | | | YYYVCQYCPAGNWANR[b] | | | | | |
| | | | NEDKDPAFTALLTTQTQVQR | | | | | |
| CXCL14 | CXL14 | O95715 | MVIITTK | MVIITTK | 403.2 | 674.4 | 575.4 | 462.3 |
| | | | WYNAWNEK | WYNAWNEK | 555.8 | 761.4 | 847.3 | 576.3 |
| | | | GQEHCLHPK[b] | | | | | |
| | | | YPHCEEK[b] | | | | | |
| IL24 | IL24 | Q13007 | LWEAFWAVK | LWEAFWAVK | 575.3 | 850.4 | 721.4 | 650.4 |
| | | | QLDVEAALTK | | | | | |
| | | | ALGEVDILLTWMQK | | | | | |
| | | | GVVPQK | | | | | |
| MMP9 | MMP9 | P14780 | AVIDDAFAR | AVIDDAFAR | 489.3 | 807.4 | 694.3 | 579.4 |
| | | | FQTFEGDLK | FQTFEGDLK | 542.8 | 809.4 | 708.4 | 561.3 |
| | | | LGLGADVAQVTGALR | LGLGADVAQVTGALR | 720.9 | 914.5 | 815.5 | 744.4 |
| | | | SLGPALLLLQK | SLGPALLLLQK | 576.9 | 952.6 | 727.5 | 614.4 |
| | | | AFALWSAVTPLTFTR | | | | | |
| POSTN | POSTN | Q15063 | AAAITSDILEALGR | AAAITSDILEALGR | 700.9 | 1074.6 | 973.5 | 771.5 |
| | | | VGLNELYNGQILETIGGK | | | | | |
| | | | NGAIHIFR | | | | | |
| | | | LILQNHILK | | | | | |
| SFRP4 | SFRP4 | Q6FHJ7 | GVCISPEAIVTDLPEDVK[b] | GVCISPEAIVTDLPEDVK[b] | 971.5 | 1425.7 | 918.5 | 587.3 |
| | | | SGCNEVTTVVDVK[b] | | | | | |
| | | | VKPTLATYLSK | | | | | |
| | | | NYSYVIHAK | | | | | |
| CD90 | CD90 | P04216 | VLYLSAFTSK | VLYLSAFTSK | 564.8 | 916.5 | 753.4 | 640.3 |
| | | | VTSLTACLVDQSLR[b] | VTSLTACLVDQSLR[b] | 521.6 | 830.5 | 717.4 | 618.3 |
| | | | HVLFGTVGVPEHTYR | HVLFGTVGVPEHTYR | 571.3 | 958.5 | 802.4 | 576.3 |
| WISP1 | WISP1 | O95388 | TIDVSFQCPDGLGFSR[b] | | | | | |
| | | | ISNVNAQCWPEQESR[b] | | | | | |
| | | | DTGAFDAVGEVEAWHR | | | | | |
| | | | YNNGQSFQPNCK[b] | | | | | |

FIG. 4

| Gene | Protein | Accession number | Best surrogate peptide[a] | SRM transitions | | |
|---|---|---|---|---|---|---|
| | | | | Q1 | Q3 | |
| AGR2 | AGR2 | O95994 | LPQTLSR | 407.7 | 476.3 | 351.2 |
| AGR3 | AGR3 | Q8TD06 | LYTYEPR | 471.2 | 272.2 | 277.2 |
| CCL3 | CCL3 | P10147 | QVCADPSEEWVQK[b] | 788.4 | 1188.6 | 1117.5 | 1002.5 |
| CEACAM5 | CEAM5 | P06731 | INGIPQQHTQVLFIAK | 603.0 | 847.5 | 761.9 | 705.4 |
| | | | SDLVNEEATGQFR | 733.3 | 1051.5 | 937.4 | 679.4 |
| | | | CETQNPVSAR[b] | 581.3 | 872.5 | 643.4 | 529.3 |
| CEACAM6 | CEAM6 | P40199 | EVLLLAHNLPQNR | 506.3 | 741.4 | 514.3 | 531.8 |
| | | | SDPVTLNVLYGPDGPTISPSK | 1079.1 | 1055.5 | 998.5 | 331.2 |
| CRISP3 | CRISP3 | P54108 | WANQCNYR[b] | 556.2 | 925.4 | 854.4 | 612.3 |
| | | | YEDLYSNCK[b] | 596.3 | 899.4 | 784.4 | 671.3 |
| CXCL14 | CXL14 | O95715 | MVIITTK | 403.2 | 674.4 | 575.4 | 462.3 |
| | | | WYNAWNEK | 555.8 | 761.4 | 647.3 | 576.3 |
| IL24 | IL24 | Q13007 | LWEAFWAVK | 575.3 | 850.4 | 721.4 | 650.4 |
| MMP9 | MMP9 | P14780 | AVIDDAFAR | 489.3 | 807.4 | 694.3 | 579.4 |
| | | | FQTFEGDLK | 542.8 | 809.4 | 708.4 | 561.3 |
| | | | LGLGADVAQVTGALR | 720.9 | 914.5 | 815.5 | 744.4 |
| | | | SLGPALLLQK | 576.9 | 952.6 | 727.5 | 614.4 |
| POSTN | POSTN | Q15063 | AAAITSDILEALGR | 700.9 | 1074.6 | 973.5 | 771.5 |
| SFRP4 | SFRP4 | Q6FHJ7 | GVCISPEAIVTDLPEDVK[b] | 971.5 | 1425.7 | 916.5 | 587.3 |
| THY1 | CD90 | P04216 | VLYLSAFTSK | 564.8 | 916.5 | 753.4 | 640.3 |
| | | | VTSLTACLVDQSLR[b] | 521.6 | 830.5 | 717.4 | 618.3 |
| | | | HVLFGTVGVPEHTYR | 571.3 | 958.5 | 802.4 | 576.3 |

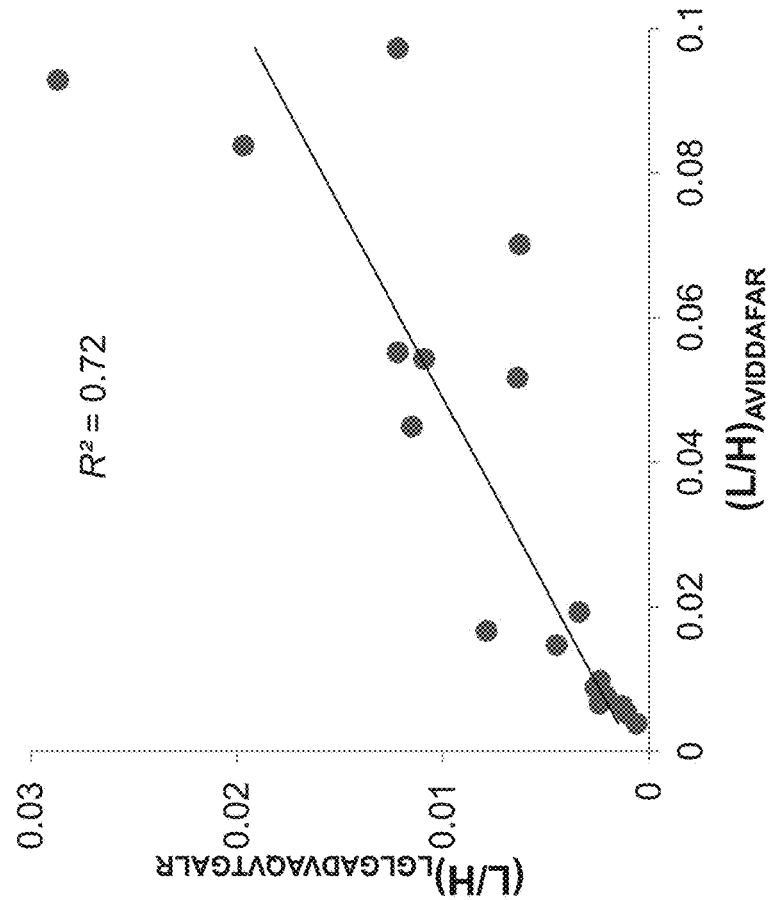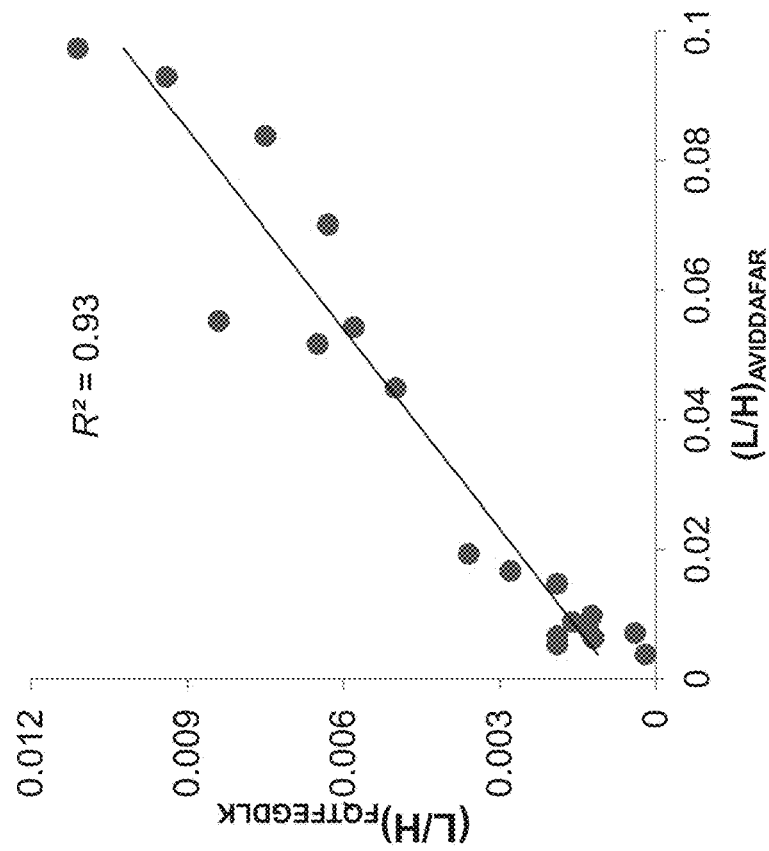
FIG. 5A
FIG. 5B

FIG. 8

| Prostate cancer patient urine ID | | IVGGWECEK (1 fmol/μL IS) | | LSEPAELTDAVK (10 fmol/μL IS) | |
|---|---|---|---|---|---|
| | | L/H | ng/100 μg of urinary protein | L/H | ng/100 μg of urinary protein |
| Non-cancer | P07022BN | 1.243 | 74.58 | 16.969 | 101.81 |
| | P07036BN | 18.011 | 1080.66 | 238.89 | 1433.34 |
| | P08018BN | 0.955 | 57.3 | 17.943 | 107.66 |
| | P08022BN | 1.007 | 60.42 | 13.778 | 82.67 |
| | P08036BN | 3.857 | 231.42 | 52.146 | 312.88 |
| | P09040AN | 0.59 | 35.4 | 8.592 | 51.55 |
| | SAP12-005C | 0.01 | 0.58 | 0.161 | 0.97 |
| | SAP12-005C | 0.007 | 0.41 | 0.098 | 0.59 |
| | SAP12-005C | 0.005 | 0.28 | 0.112 | 0.67 |
| Post-operative | SAP12-005C | 0.001 | 0.06 | 0.015 | 0.09 |
| | SAP12-005C | 0 | 0.02 | 0.002 | 0.01 |
| | SAP12-005C | 0.043 | 2.55 | 0.616 | 3.7 |
| | SAP12-005C | 0.049 | 2.95 | 0.62 | 3.72 |
| | P06003Pre | 0.249 | 14.94 | 2.666 | 16 |
| | P06011Pre | 0.33 | 19.8 | 4.434 | 26.6 |
| | P06017Pre | 0.169 | 10.14 | 1.656[a] | 9.94[a] |
| | P07016Pre | 0.002 | 0.12 | 0.015 | 0.09 |
| | P07018Pre | 0.893 | 53.58 | 13.002 | 78.01 |
| | P07019Pre | 0.003 | 0.18 | 0.031 | 0.19 |
| | P07029Pre | 0.046 | 2.76 | 0.348 | 2.09 |
| Cancer | P07031Pre | 0.196 | 11.76 | 2.702 | 16.21 |
| | P07040Pre | 0.366[a] | 21.96[a] | 5.02 | 30.12 |
| | P07047Pre | 0.145 | 8.7 | 1.94 | 11.64 |
| | P08006rPre | 3.393 | 203.58 | 54.666 | 328 |
| | P08015Pre | 4.739[a] | 284.34[a] | 65.602 | 393.61 |
| | P08028Pre | 0.087 | 5.22 | 1.272 | 7.63 |
| | P08032Pre | 0.681 | 40.86 | 14.453 | 86.72 |

FIG. 10

| Prostate cancer patient urine ID | | IVGGWECEK | | Average (ng/100 μg) | Median (ng/100 μg) | Average | Median |
|---|---|---|---|---|---|---|---|
| | | L/H | ng/100 μg of urinary protein | Pre-operative and non-cancer | Pre-operative and non-cancer | $(PSA_{post-operative})/(PSA_{non-cancer/pre-operative})\%$ | |
| Pre-operative and non-cancer | P07022BN | 1.243 | 74.58 | 110.89 | 28.68 | 0.88% | 1.42% |
| | P07036BN | 18.011 | 1080.66 | | | | |
| | P08018N | 0.955 | 57.3 | | | | |
| | P08022N | 1.007 | 60.42 | | | | |
| | P08036BN | 3.857 | 231.42 | | | | |
| | P09040AN | 0.59 | 35.4 | | | | |
| | P06003Pre | 0.249 | 14.94 | | | | |
| | P06011Pre | 0.33 | 19.8 | | | | |
| | P06017Pre | 0.169 | 10.14 | | | | |
| | P07016Pre | 0.002 | 0.12 | | | | |
| | P07018Pre | 0.893 | 53.58 | | | | |
| | P07019Pre | 0.003 | 0.18 | | | | |
| | P07029Pre | 0.046 | 2.76 | | | | |
| | P07031Pre | 0.196 | 11.76 | | | | |
| | P07040Pre[a] | 0.366 | 21.96 | | | | |
| | P07047Pre | 0.145 | 8.7 | | | | |
| | P08006rPre | 3.393 | 203.58 | | | | |
| | P08015Pre[a] | 4.739 | 284.34 | | | | |
| | P08028Pre | 0.087 | 5.22 | | | | |
| | P08032Pre | 0.681 | 40.86 | | | | |
| | | | | Post-operative | Post-operative | | |
| Post-operative | SAP12-005C | 0.01 | 0.58 | 0.98 | 0.41 | | |
| | SAP12-006C | 0.007 | 0.41 | | | | |
| | SAP12-007C | 0.005 | 0.28 | | | | |
| | SAP12-008C | 0.001 | 0.06 | | | | |
| | SAP12-009C | 0 | 0.02 | | | | |
| | SAP12-0010C | 0.043 | 2.55 | | | | |
| | SAP12-0022C | 0.049 | 2.95 | | | | |

FIG. 11A

| Prostate cancer patient urine ID | | AGR2 LPQTLSR | AGR3 LYTYEPR | CEACAM5 SDLVNEEATGQFR | CEACAM6 EVLLLAHNLPQNR | CRISP3 WANQCNYR | CRISP3 YEDLYSNCK | VLYLSAFTSK | CD90 VTSLTACLVDQSLR | HVLFGTVGVPEHTYR |
|---|---|---|---|---|---|---|---|---|---|---|
| Non-cancer | P07022BN | 0.0017 | 0.0003 | 0.0002 | 0.0002 | 0.294 | 0.1463 | 0.0119 | 0.6726 | 0.8521 |
| | P07036BN | 0.0038 | 0.0005 | 0.0001 | 0.0003 | 0.4128 | 0.2687 | 0.0124 | 0.5856 | 0.9345 |
| | P08018BN | 0.0008 | 0.001 | 0.0009 | 0.0011 | 0.351 | 0.0421 | 0.0332 | 0.101 | 1.2564 |
| | P08022BN | 0.0029 | 0.0015 | 0.0028 | 0.0019 | 0.499 | 0.113 | 0.081 | 0.4831 | 1.9659 |
| | P08036BN | 0.0020 | 0.0031 | 0.0034 | 0.0002 | 0.1407 | 0.0408 | 0.0211 | 0.1166 | 0.4949 |
| | P09040AN | 0.0078 | 0.0007 | 0.0024 | 0.0057 | 0.8341 | 0.1021 | 0.0315 | 0.2858 | 0.8076 |
| | P06003Pre | 0.0004 | 0.0002 | 0.0008 | 0.0005 | 0.1442 | 0.0983 | 0.0152 | 0.7154 | 1.4928 |
| | P06011Pre | 0.0033 | 0.002 | 0.003 | 0.0028 | 0.2389 | 0.0404 | 0.0429 | 0.3053 | 1.0111 |
| | P06017Pre | 0.0034 | 0.0007 | 0.0003 | 0.0002 | 0.3154 | 0.172267 | 0.105733 | 1.608733 | 3.9558 |
| | P07016Pre | 0.0066 | 0.0021 | 0.0004 | 0.0005 | 0.1278 | 0.0896 | 0.046 | 0.7832 | 1.138 |
| | P07018Pre | 0.0134 | 0.0016 | 0.0089 | 0.0032 | 1.8468 | 0.2898 | 0.0664 | 0.4069 | 1.6313 |
| | P07019Pre | 0.0009 | 0.0005 | 0.0029 | 0.0032 | 0.2777 | 0.0469 | 0.0436 | 0.3481 | 1.0873 |
| | P07029Pre | 0.0001 | 0.0009 | 0.0005 | 0.0003 | 0.1311 | 0.0643 | 0.0188 | 0.2366 | 0.8335 |
| Cancer | P07031Pre | 0.0268 | 0.003 | 0.011 | 0.0028 | 0.7751 | 0.166 | 0.0357 | 0.2079 | 0.8057 |
| | P07040Pre | 0.0037 | 0.0032 | 0.0015 | 0.0011 | 0.2103 | 0.0163 | 0.0175 | 0.091 | 0.4373 |
| | P07047Pre | 0.0007 | 0.0015 | 0.0037 | 0.0013 | 0.2924 | 0.0596 | 0.0353 | 0.2578 | 0.9699 |
| | P0800brPre | 0.0015 | 0.0008 | 0.0026 | 0.002 | 0.2887 | 0.0398 | 0.0371 | 0.3319 | 1.0472 |
| | P08015Pre | 0.0021 | 0.002 | 0.0022 | 0.003 | 0.6987 | 0.0663 | 0.0151 | 0.0793 | 0.7124 |
| | P08028Pre | 0.0021 | 0.0016 | 0.0024 | 0.0019 | 0.4659 | 0.0677 | 0.0463 | 0.3123 | 1.2306 |
| | P08032Pre | 0.0009 | 0.0022 | 0.003 | 0.0055 | 0.3565 | 0.0457 | 0.0366 | 0.2275 | 1.0941 |

$(L/H)_{peptide\ marker}$

FIG. 11B

| Prostate cancer patient | | CXCL14 | IL24 | | MMP9 | | | SFRP4 |
|---|---|---|---|---|---|---|---|---|
| | urine ID | MVIITTK | LWEAFWAVK | AVIDDAFAR | FQTFEGDLK | LGLGADVAQVTGALR | SLGPALLLQK | GVCISPEAIVTDLPEDVK |
| | | (L/H)peptide marker | | | | | | |
| Non-cancer | P07022BN | 0.0025 | 0.0017 | 0.0063 | 0.0012 | 0.0013 | 0.0007 | 0.0061 |
| | P07036BN | 0.003 | 0.0012 | 0.0071 | 0.0004 | 0.0023 | 0.0012 | 0.0053 |
| | P08018BN | 0.0041 | 0.0011 | 0.0838 | 0.0075 | 0.0197 | 0.0125 | 0.0598 |
| | P08022BN | 0.0025 | 0.0007 | 0.0973 | 0.0111 | 0.0122 | 0.0049 | 0.0659 |
| | P08036BN | 0.0056 | 0.0013 | 0.0167 | 0.0028 | 0.0079 | 0.0028 | 0.0331 |
| | P09040AN | 0.013 | 0.0013 | 0.0147 | 0.0019 | 0.0045 | 0.0029 | 0.0558 |
| | P06003Pre | 0.0001 | 0.0018 | 0.0088 | 0.0016 | 0.0026 | 0.0016 | 0.0121 |
| | P06011Pre | 0.0046 | 0.0009 | 0.0929 | 0.0094 | 0.0287 | 0.0206 | 0.0521 |
| | P06017Pre | 0.001767 | 0.001233333 | 0.0098 | 0.001233 | 0.0024 | 0.001 | 0.022667 |
| | P07016Pre | 0.0049 | 0.0013 | 0.0053 | 0.0019 | 0.0011 | 0.0005 | 0.0164 |
| | P07018Pre | 0.0043 | 0.0011 | 0.0449 | 0.005 | 0.0115 | 0.0072 | 0.0503 |
| | P07019Pre | 0.0048 | 0.0014 | 0.0077 | 0.0013 | 0.0021 | 0.0007 | 0.0461 |
| Cancer | P07029Pre | 0.0006 | 0.0011 | 0.0038 | 0.0002 | 0.0006 | 0.0006 | 0.0087 |
| | P07031Pre | 0.0086 | 0.0016 | 0.0517 | 0.0065 | 0.0064 | 0.003 | 0.0304 |
| | P07040Pre | 0.0052 | 0.0012 | 0.0701 | 0.0063 | 0.0063 | 0.0114 | 0.0348 |
| | P07047Pre | 0.0198 | 0.0022 | 0.0066 | 0.0019 | 0.0024 | 0.0005 | 0.0352 |
| | P08006rPre | 0.0048 | 0.0011 | 0.0193 | 0.0036 | 0.0034 | 0.002 | 0.0553 |
| | P08015Pre | 0.001 | 0.0013 | 1.3222 | 0.09 | 0.0821 | 0.2222 | 0.0222 |
| | P08028Pre | 0.002 | 0.0014 | 0.0552 | 0.0084 | 0.0122 | 0.0113 | 0.0312 |
| | P08032Pre | 0.0053 | 0.0014 | 0.0543 | 0.0058 | 0.0109 | 0.0079 | 0.0518 |

FIG. 12

| Gene | Protein | Peptide | $(L/H)_{peptide\ marker}$ P value[a] | AUC | P value[a] | $(L/H)_{peptide\ marker}/(L/H)_{PSA}$ AUC | Sensitivity | Specificity[b] |
|---|---|---|---|---|---|---|---|---|
| AGR2 | AGR2 | LPQTLSR | 0.773 | 0.45 | 0.063 | 0.77 | 0.93 | 0.67 |
| AGR3 | AGR3 | LYTYEPR | 0.283 | 0.66 | 0.019 | 0.85 | 0.79 | 1 |
| CEACAM5 | CEAM5 | SDLVNEEATGQFR | 0.322 | 0.65 | 0.012 | 0.87 | 0.71 | 1 |
| CEACAM6 | CEAM6 | EVLLLAHNLPQNR | 0.246 | 0.67 | 0.029 | 0.82 | 0.79 | 0.83 |
| CRISP3 | CRISP3 | WANQCNYR[c] | 0.386 | 0.63 | 0.035 | 0.86 | 0.86 | 0.83 |
| CRISP3 | CRISP3 | YEDLYSNCK[c] | 0.433 | 0.38 | 0.035 | 0.81 | 0.64 | 1 |
| THY1 | CD90 | VLYLSAFTSK | 0.174 | 0.70 | 0.015 | 0.86 | 0.86 | 0.83 |
| THY1 | CD90 | VTSLTACLVDQSLR[c] | 0.967 | 0.45 | 0.063 | 0.77 | 0.64 | 1 |
| THY1 | CD90 | HVLFGTVGVPEHTYR | 0.650 | 0.57 | 0.012 | 0.87 | 0.86 | 0.83 |
| CXCL14 | CXL14 | MVIITTK | 0.836 | 0.46 | 0.091 | 0.75 | 0.79 | 0.83 |
| IL24 | IL24 | LWEAFWAVK | 0.479 | 0.61 | 0.015 | 0.86 | 0.71 | 1 |
| MMP9 | MMP9 | AVIDDAFAR | 1 | 0.50 | 0.029 | 0.82 | 0.93 | 0.67 |
| MMP9 | MMP9 | FQTFEGDLK | 0.710 | 0.56 | 0.015 | 0.86 | 0.93 | 0.67 |
| MMP9 | MMP9 | LGLGADVAQVTGALR | 0.869 | 0.47 | 0.015 | 0.86 | 0.86 | 0.83 |
| MMP9 | MMP9 | SLGPALLLQK | 1 | 0.49 | 0.015 | 0.86 | 0.85 | 0.83 |
| SFRP4 | SFRP4 | GVCISPEAIVTDLPEDVK[c] | 0.592 | 0.42 | 0.023 | 0.83 | 0.64 | 1 |

FIG. 13A

| | | AGR2 | AGR3 | CEACAM5 | CEACAM6 | CRISP3 | | | CD90 | |
|---|---|---|---|---|---|---|---|---|---|---|
| | | | | | | | | | $(L/H)_{peptide\ marker}/(L/H)_{PSA}$ | |
| Prostate cancer patient urine ID | | LPQTLSR | LYTYEPR | INGIPQQHTQ VLFIAK | EVILLAHNLP QNR | WANQCNYR | YEDLYSNCK | VLYLSAFTSK | VTSLTACLVD QSLR | HVLFGTVGVPE HTYR |
| Non-cancer | P07022BN | 0.00138 | 0.00024 | 0.00016 | 0.00016 | 0.23649 | 0.11768 | 0.00957 | 0.54104 | 0.68543 |
| | P07036BN | 0.00021 | 0.00003 | 0.00001 | 0.00002 | 0.02292 | 0.01492 | 0.00069 | 0.03251 | 0.05188 |
| | P08018BN | 0.00086 | 0.00105 | 0.00094 | 0.00115 | 0.36762 | 0.04409 | 0.03477 | 0.10578 | 1.31589 |
| | P08022BN | 0.00288 | 0.00149 | 0.00278 | 0.00189 | 0.49569 | 0.11225 | 0.08046 | 0.4799 | 1.95287 |
| | P08036BN | 0.00051 | 0.0008 | 0.00088 | 0.00005 | 0.03648 | 0.01058 | 0.00547 | 0.03023 | 0.12832 |
| | P09040AN | 0.01323 | 0.00119 | 0.00407 | 0.00967 | 1.41489 | 0.17319 | 0.05343 | 0.48481 | 1.36994 |
| | P06003Pre | 0.00149 | 0.0008 | 0.00321 | 0.00201 | 0.57839 | 0.39428 | 0.06097 | 2.86949 | 5.98767 |
| | P06011Pre | 0.01009 | 0.00606 | 0.00909 | 0.00848 | 0.72382 | 0.1224 | 0.12998 | 0.925 | 3.06344 |
| | P06017Pre | 0.02006 | 0.00414 | 0.00177 | 0.00118 | 1.86532 | 1.01881 | 0.62532 | 9.51428 | 23.39518 |
| | P07016Pre | 3.41433 | 1.09181 | 0.20796 | 0.25996 | 66.44465 | 46.58404 | 23.91591 | 407.19443 | 591.65891 |
| | P07018Pre | 0.01495 | 0.00179 | 0.00997 | 0.00358 | 2.06809 | 0.32453 | 0.07436 | 0.45566 | 1.82677 |
| | P07019Pre | 0.28319 | 0.15053 | 0.87306 | 0.96337 | 83.60257 | 14.11941 | 13.12593 | 104.79674 | 327.33553 |
| Cancer | P07029Pre | 0.00232 | 0.01942 | 0.01079 | 0.00647 | 2.8282 | 1.38714 | 0.40557 | 5.10414 | 17.98099 |
| | P07031Pre | 0.13680 | 0.01531 | 0.05612 | 0.01429 | 3.95468 | 0.84696 | 0.18215 | 1.06074 | 4.11081 |
| | P07040Pre[a] | 0.00999 | 0.00874 | 0.0041 | 0.00301 | 0.57459 | 0.04454 | 0.04781 | 0.24863 | 1.19481 |
| | P07047Pre | 0.00481 | 0.01037 | 0.02557 | 0.00898 | 2.02063 | 0.41187 | 0.24394 | 1.78153 | 6.70251 |
| | P08006rPre | 0.00044 | 0.00024 | 0.00077 | 0.00059 | 0.08508 | 0.01173 | 0.01093 | 0.09781 | 0.30862 |
| | P08015Pre[a] | 0.00044 | 0.00042 | 0.00046 | 0.00063 | 0.14744 | 0.01399 | 0.00319 | 0.01673 | 0.15033 |
| | P08028Pre | 0.02370 | 0.0184 | 0.0276 | 0.02185 | 5.35712 | 0.77844 | 0.53238 | 3.59096 | 14.14996 |
| | P08032Pre | 0.00139 | 0.00323 | 0.00441 | 0.00808 | 0.52381 | 0.06715 | 0.05378 | 0.33427 | 1.60757 |

FIG. 13B

| Prostate cancer patient urine ID | | CXCL14 MVIITTK | IL24 LWEAFWAVK | AVIDDAFAR | MMP9 FQTFEGDLK | LGLGADVA QVTGALR | SLGPALLLQK | SFRP4 GVCISPEAIVT DLPEDVK |
|---|---|---|---|---|---|---|---|---|
| | | | | $(L/H)_{peptide\ marker}/(L/H)_{PSA}$ | | | | |
| Non-cancer | P07022BN | 0.00201 | 0.00137 | 0.00507 | 0.00097 | 0.00105 | 0.00056 | 0.00491 |
| | P07036BN | 0.00017 | 0.00007 | 0.00039 | 0.00002 | 0.00013 | 0.00007 | 0.00029 |
| | P08018BN | 0.00429 | 0.00115 | 0.08777 | 0.00786 | 0.02063 | 0.01309 | 0.06263 |
| | P08022BN | 0.00248 | 0.0007 | 0.09666 | 0.01103 | 0.01212 | 0.00487 | 0.06546 |
| | P08036BN | 0.00145 | 0.00034 | 0.00433 | 0.00073 | 0.00205 | 0.00073 | 0.00858 |
| | P09040AN | 0.02205 | 0.00221 | 0.02494 | 0.00322 | 0.00763 | 0.00492 | 0.09465 |
| | P06003Pre | 0.0004 | 0.00722 | 0.0353 | 0.00642 | 0.01043 | 0.00642 | 0.04853 |
| | P06011Pre | 0.01394 | 0.00273 | 0.28147 | 0.02848 | 0.08696 | 0.06241 | 0.15785 |
| | P06017Pre | 0.01045 | 0.00729 | 0.05796 | 0.00729 | 0.01419 | 0.00591 | 0.13405 |
| | P07016Pre | 2.54756 | 0.67588 | 2.75553 | 0.98783 | 0.5719 | 0.25996 | 8.52654 |
| | P07018Pre | 0.00482 | 0.00123 | 0.05028 | 0.0056 | 0.01288 | 0.00806 | 0.05633 |
| | P07019Pre | 1.44506 | 0.42147 | 2.31811 | 0.39137 | 0.63221 | 0.21074 | 13.87857 |
| Cancer | P07029Pre | 0.01294 | 0.02373 | 0.08198 | 0.00431 | 0.01294 | 0.01294 | 0.18768 |
| | P07031Pre | 0.04388 | 0.00816 | 0.26378 | 0.03316 | 0.03265 | 0.01531 | 0.15511 |
| | P07040Pre[a] | 0.01421 | 0.00328 | 0.19153 | 0.01721 | 0.01721 | 0.03115 | 0.09508 |
| | P07047Pre | 0.13683 | 0.0152 | 0.04561 | 0.01313 | 0.01659 | 0.00346 | 0.24325 |
| | P08006grPre | 0.00141 | 0.00032 | 0.00569 | 0.00106 | 0.001 | 0.00059 | 0.0163 |
| | P08015Pre[a] | 0.00021 | 0.00027 | 0.279 | 0.01899 | 0.01732 | 0.04689 | 0.00468 |
| | P08028Pre | 0.023 | 0.0161 | 0.63471 | 0.09659 | 0.14028 | 0.12993 | 0.35875 |
| | P08032Pre | 0.00779 | 0.00206 | 0.07978 | 0.00852 | 0.01602 | 0.01161 | 0.07611 |

FIG. 15

| Combinations (gene/surrogate peptide) | P value[a] | AUC | Sensitivity[b] | Specificity[b] |
|---|---|---|---|---|
| AGR2/LPQTLSR, AGR3/LYTYEPR, CEACAM5/SDLVNEEATGQFR, CEACAM6/EVLLLAHNLPQNR | 0.0044 | 0.92 | 0.78 | 1 |
| AGR2/LPQTLSR, AGR3/LYTYEPR, CEACAM5/SDLVNEEATGQFR, CEACAM6/EVLLLAHNLPQNR, THY1/VTSLTACLVDQSLR[c] | 0.0034 | 0.93 | 0.86 | 1 |
| AGR2/LPQTLSR, AGR3/LYTYEPR, CEACAM5/SDLVNEEATGQFR, CEACAM6/EVLLLAHNLPQNR, MMP9/LGLGADVAQVTGALR | 0.0034 | 0.93 | 0.86 | 1 |
| AGR2/LPQTLSR, AGR3/LYTYEPR, CEACAM5/SDLVNEEATGQFR, THY1/VTSLTACLVDQSLR[c], SFRP4/GVCISPEAIVTDLPEDVK[c] | 0.0020 | 0.95 | 0.86 | 1 |
| AGR3/LYTYEPR, CEACAM5/SDLVNEEATGQFR, CEACAM6/EVLLLAHNLPQNR, CRISP3/WANQCNYR[c] | 0.0043 | 0.92 | 0.78 | 1 |
| AGR3/LYTYEPR, CEACAM5/SDLVNEEATGQFR, CEACAM6/EVLLLAHNLPQNR, CRISP3/WANQCNYR[c], THY1/VLYLSAFTSK | 0.0034 | 0.93 | 0.78 | 1 |
| CEACAM5/SDLVNEEATGQFR, CEACAM6/EVLLLAHNLPQNR, CRISP3/WANQCNYR[c], THY1/VLYLSAFTSK, IL24/LWEAFWAVK | 0.0034 | 0.93 | 0.86 | 1 |
| CEACAM5/SDLVNEEATGQFR, CEACAM6/EVLLLAHNLPQNR, CRISP3/WANQCNYR[c], CRISP3/YEDLYSNCK[c], THY1/VLYLSAFTSK | 0.0034 | 0.93 | 0.86 | 1 |
| CD90/HVLFGTVGVPEHTYR, CXCL14/MVIIITTK, IL24/LWEAFWAVK, MMP9/AVIDDAFAR, MMP9/FQTFEGDLK | 0.0044 | 0.92 | 0.86 | 1 |
| IL24/LWEAFWAVK, MMP9/AVIDDAFAR, MMP9/FQTFEGDLK, MMP9/LGLGADVAQVTGALR | 0.0057 | 0.90 | 0.86 | 1 |

FIG. 17

| Prostate cancer patient urine ID | | ng/100 μg of total urinary protein | ng/mL in serum |
|---|---|---|---|
| Non-cancer | P07022BN | 74.58 | 0.91 |
| | P07036BN | 1080.66 | 3.59 |
| | P08018BN | 57.3 | 4.7 |
| | P08022BN | 60.42 | 1.7 |
| | P08036BN | 231.42 | 2.29 |
| | P09040AN | 35.4 | |
| | P06003Pre | 14.94 | 5.2 |
| | P06011Pre | 19.8 | 5.82 |
| | P06017Pre | 10.14 | 5.75 |
| | P07016Pre | 0.12 | |
| | P07018Pre | 53.58 | 5.89 |
| | P07019Pre | 0.18 | 6.6 |
| Cancer | P07029Pre | 2.76 | 3.75 |
| | P07031Pre | 11.76 | 87.2 |
| | P07040Pre[a] | 21.96 | 3.4 |
| | P07047Pre | 8.7 | 6 |
| | P08006rPre | 203.58 | 6.4 |
| | P08015Pre[a] | 284.34 | 3.6 |
| | P08028Pre | 5.22 | 5.3 |
| | P08032Pre | 40.86 | 8.1 |

FIG. 18A

| Sample ID | Type | Gleason score | tumor volume | stage | AGR2 LPQTLSR | AGR3 LVTYEPR | CEACAM5 SDLVNEEA TGQFR | CEACAM6 EVLILLAHN LPQNR | WANQCNYR | CRISP3 YEDLYSNCK |
|---|---|---|---|---|---|---|---|---|---|---|
| P06-003Pre | Cancer | 3+3 bx | na | na | 0.001495 | 0.000802 | 0.0032 | 0.002 | 0.578391 | 0.394285 |
| P06-017Pre | Cancer | 3+3 bx | na | na | 0.020063 | 0.00414 | 0.0018 | 0.0012 | 1.865322 | 1.018812 |
| P07-018Pre | Cancer | 3+3 bx | na | na | 0.014954 | 0.001792 | 0.01 | 0.0036 | 2.068094 | 0.324526 |
| P07-040Pre | Cancer | 3+3 | 0.1 | T2a | 0.009992 | 0.008743 | 0.0041 | 0.003 | 0.57459 | 0.044536 |
| P07-029Pre | Cancer | 3+3 | 0.5 | T2c | 0.002316 | 0.019416 | 0.0108 | 0.0065 | 2.828203 | 1.387136 |
| P08-006Pre | Cancer | 3+3 | 0.5 | T2c | 0.000436 | 0.000236 | 0.0008 | 0.0006 | 0.085082 | 0.011729 |
| P08-015Pre | Cancer | 3+4 | 2.5 | T2c | 0.000443 | 0.000422 | 0.0005 | 0.0006 | 0.147436 | 0.01399 |
| P08-028Pre | Cancer | 3+4 | 4 | T3b | 0.023695 | 0.018397 | 0.0276 | 0.0218 | 5.357116 | 0.778443 |
| P07-032Pre | Cancer | 4+3 | 1 | T2c | 0.001386 | 0.003232 | 0.0044 | 0.0081 | 0.52381 | 0.067148 |
| P07-047Pre | Cancer | 4+3 | 1.5 | T2c | 0.004811 | 0.010366 | 0.0256 | 0.009 | 2.020635 | 0.411867 |
| P07-031Pre | Cancer | 4+5 bx | na | TxN1 | 0.136805 | 0.015306 | 0.0561 | 0.0143 | 3.954685 | 0.846959 |
| Average value | | ≤ 6 | ≤ 0.5 | | 0.008209 | 0.005855 | 0.0051 | 0.00281 | 1.333281 | 0.530171 |
| | | > 6 | > 0.5 | | 0.033428 | 0.009545 | 0.02283 | 0.01077 | 2.400736 | 0.423681 |
| Median value | | ≤ 6 | ≤ 0.5 | | 0.006154 | 0.002966 | 0.00365 | 0.00251 | 1.221857 | 0.359405 |
| | | > 6 | > 0.5 | | 0.004811 | 0.010366 | 0.02557 | 0.00898 | 2.020635 | 0.411867 |
| Mann-Whitney U test, p value | | | | | 0.784 | 0.523 | 0.235 | 0.083 | 0.648 | 1 |

FIG. 18B

| Sample ID | Type | Gleason score | tumor volume | stage | CD90 VLYLSAFT SK | CD90 VTSLTACL VDQSLR | CD90 HVLFGTVGV PEHTYR | CXCL14 MVIHTTK | IL24 AVK | IL24 LWEAFW AR | AVIDDAF | MMP9 FQTFEGD LK | MMP9 LGLGAD ALR | MMP9 VAQVTG SLGPALLLL QK | SFRP4 GVCISPE AIVTDLP EDVK | sPSA | uPSA |
|---|---|---|---|---|---|---|---|---|---|---|---|---|---|---|---|---|---|
| P06-003Pre | Cancer | 3+3 bx | na | na | 0.061 | 2.8695 | 5.9877 | 0.0004 | 0.0072 | 0.0353 | | 0.0064 | 0.0104 | 0.0064 | 0.0485 | 5.2 | 0.2493 |
| P06-017Pre | Cancer | 3+3 bx | na | na | 0.6253 | 9.5143 | 23.395 | 0.01045 | 0.0073 | 0.058 | | 0.0073 | 0.0142 | 0.0059 | 0.1341 | 5.75 | 0.1691 |
| P07-018Pre | Cancer | 3+3 bx | na | na | 0.0744 | 0.4557 | 1.8268 | 0.00482 | 0.0012 | 0.0503 | | 0.0056 | 0.0129 | 0.0081 | 0.0563 | 5.89 | 0.893 |
| P07-040Pre | Cancer | 3+3 | 0.1 | T2a | 0.0478 | 0.2486 | 1.1948 | 0.01421 | 0.0033 | 0.1915 | | 0.0172 | 0.0172 | 0.0311 | 0.0951 | 3.4 | 0.356 |
| P07-029Pre | Cancer | 3+3 | 0.5 | T2c | 0.4056 | 5.1041 | 17.981 | 0.01294 | 0.0237 | 0.082 | | 0.0043 | 0.0129 | 0.0129 | 0.1877 | 3.75 | 0.0464 |
| P08-006Pre | Cancer | 3+3 | 0.5 | T2c | 0.0109 | 0.0978 | 0.3086 | 0.00141 | 0.0003 | 0.0057 | | 0.0011 | 0.001 | 0.0006 | 0.0163 | 6.4 | 3.3932 |
| P08-015Pre | Cancer | 3+4 | 2.5 | T2c | 0.0032 | 0.0167 | 0.1503 | 0.00021 | 0.0003 | 0.279 | | 0.019 | 0.0173 | 0.0469 | 0.0047 | 3.6 | 4.739 |
| P08-028Pre | Cancer | 3+4 | 4 | T3b | 0.5324 | 3.591 | 14.15 | 0.023 | 0.0161 | 0.6347 | | 0.0966 | 0.1403 | 0.1299 | 0.3588 | 5.3 | 0.087 |
| P08-032Pre | Cancer | 4+3 | 1 | T2c | 0.0538 | 0.3343 | 1.6076 | 0.00779 | 0.0021 | 0.0798 | | 0.0085 | 0.016 | 0.0116 | 0.0761 | 8.1 | 0.6806 |
| P07-047Pre | Cancer | 4+3 | 1.5 | T2c | 0.2439 | 1.7815 | 6.7025 | 0.13683 | 0.0152 | 0.0456 | | 0.0131 | 0.0166 | 0.0035 | 0.2433 | 6 | 0.1447 |
| P07-031Pre | Cancer | 4+5 bx | na | TxN1 | 0.1821 | 1.0607 | 4.1108 | 0.04388 | 0.0082 | 0.2638 | | 0.0332 | 0.0327 | 0.0153 | 0.1551 | 87.2 | 0.196 |
| Average value | | ≤ 6 | ≤ 0.5 | | 0.008209 | 0.005855 | 0.0051 | 0.00281 | 1.333281 | 0.530171 | | 0.00698 | 0.01144 | 0.01085 | 0.08966 | 5.065 | 0.85282 |
| | | > 6 | > 0.5 | | 0.033428 | 0.009545 | 0.02283 | 0.01077 | 2.400736 | 0.423681 | | 0.03408 | 0.04457 | 0.04144 | 0.15758 | 22.04 | 1.16945 |
| Median value | | ≤ 6 | ≤ 0.5 | | 0.006154 | 0.002966 | 0.00365 | 0.00251 | 1.221857 | 0.359405 | | 0.00601 | 0.01291 | 0.00724 | 0.0757 | 5.475 | 0.30766 |
| | | > 6 | > 0.5 | | 0.004811 | 0.010366 | 0.02557 | 0.00898 | 2.020635 | 0.411867 | | 0.01899 | 0.01732 | 0.01531 | 0.15511 | 6 | 0.196 |
| Mann-Whitney U test, p value | | | | | 0.784 | 0.523 | 0.235 | 0.083 | 0.648 | 1 | | 0.022 | 0.022 | 0.235 | 0.411 | 0.32 | 0.92 | ial

SEQUENCE LISTING

```
<160> NUMBER OF SEQ ID NOS: 78

<210> SEQ ID NO 1
<211> LENGTH: 175
<212> TYPE: PRT
<213> ORGANISM: Homo sapiens

<400> SEQUENCE: 1

Met Glu Lys Ile Pro Val Ser Ala Phe Leu Leu Leu Val Ala Leu Ser
1               5                   10                  15
```

```
Tyr Thr Leu Ala Arg Asp Thr Val Lys Pro Gly Ala Lys Lys Asp
             20                  25                  30

Thr Lys Asp Ser Arg Pro Lys Leu Pro Gln Thr Leu Ser Arg Gly Trp
         35                  40                  45

Gly Asp Gln Leu Ile Trp Thr Gln Thr Tyr Glu Glu Ala Leu Tyr Lys
 50                  55                  60

Ser Lys Thr Ser Asn Lys Pro Leu Met Ile Ile His His Leu Asp Glu
 65                  70                  75                  80

Cys Pro His Ser Gln Ala Leu Lys Lys Val Phe Ala Glu Asn Lys Glu
                 85                  90                  95

Ile Gln Lys Leu Ala Glu Gln Phe Val Leu Leu Asn Leu Val Tyr Glu
            100                 105                 110

Thr Thr Asp Lys His Leu Ser Pro Asp Gly Gln Tyr Val Pro Arg Ile
            115                 120                 125

Met Phe Val Asp Pro Ser Leu Thr Val Arg Ala Asp Ile Thr Gly Arg
130                 135                 140

Tyr Ser Asn Arg Leu Tyr Ala Tyr Glu Pro Ala Asp Thr Ala Leu Leu
145                 150                 155                 160

Leu Asp Asn Met Lys Lys Ala Leu Lys Leu Leu Lys Thr Glu Leu
                165                 170                 175

<210> SEQ ID NO 2
<211> LENGTH: 996
<212> TYPE: DNA
<213> ORGANISM: Homo sapiens

<400> SEQUENCE: 2
aatcacttgg ggaaaggaag gttcgtttct gagttagcaa caagtaaatg cagcactagt      60
gggtgggatt gaggtatgcc ctggtgcata aatagagact cagctgtgct ggcacactca     120
gaagcttgga ccgcatccta gccgccgact cacacaaggc aggtgggtga ggaaatccag     180
agttgccatg gagaaaattc cagtgtcagc attcttgctc cttgtggccc tctcctacac     240
tctggccaga gataccacag tcaaacctgg agcaaaaaag gacacaaagg actctcgacc     300
caaactgccc cagaccctct ccagaggttg gggtgaccaa ctcatctgga ctcagacata     360
tgaagaagct ctatataaat ccaagacaag caacaaaccc ttgatgatta ttcatcactt     420
ggatgagtgc ccacacagtc aagctttaaa gaaagtgttt gctgaaaata agaaatccga     480
gaaattggca gagcagtttg tcctcctcaa tctggtttat gaaacaactg acaaacacct     540
ttctcctgat ggccagtatg tccccaggat tatgtttgtt gacccatctc tgacagttag     600
agccgatatc actggaagat attcaaatcg tctctatgct tacgaacctg cagatacagc     660
tctgttgctt gacaacatga agaaagctct caagttgctg aagactgaat tgtaaagaaa     720
aaaaatctcc aagcccttct gtctgtcagg ccttgagact tgaaaccaga agaagtgtga     780
gaagactggc tagtgtggaa gcatagtgaa cacactgatt aggttatggt ttaatgttac     840
aacaactatt ttttaagaaa aacaagtttt agaaatttgg tttcaagtgt acatgtgtga     900
aaacaatatt gtatactacc atagtgagcc atgattttct aaaaaaaaaa ataaatgttt     960
tgggggtgtt ctgttttctc caaaaaaaaa aaaaaa                                996

<210> SEQ ID NO 3
<211> LENGTH: 7
<212> TYPE: PRT
<213> ORGANISM: Artificial Sequence
<220> FEATURE:
```

<223> OTHER INFORMATION: ARG2 peptide

<400> SEQUENCE: 3

Leu Pro Gln Thr Leu Ser Arg
1               5

<210> SEQ ID NO 4
<211> LENGTH: 166
<212> TYPE: PRT
<213> ORGANISM: Homo sapiens

<400> SEQUENCE: 4

Met Met Leu His Ser Ala Leu Gly Leu Cys Leu Leu Val Thr Val
1               5                   10                  15

Ser Ser Asn Leu Ala Ile Ala Ile Lys Lys Glu Lys Arg Pro Pro Gln
                20                  25                  30

Thr Leu Ser Arg Gly Trp Gly Asp Ile Thr Trp Val Gln Thr Tyr
            35                  40                  45

Glu Glu Gly Leu Phe Tyr Ala Gln Lys Ser Lys Lys Pro Leu Met Val
        50                  55                  60

Ile His His Leu Glu Asp Cys Gln Tyr Ser Gln Ala Leu Lys Lys Val
65                  70                  75                  80

Phe Ala Gln Asn Glu Glu Ile Gln Glu Met Ala Gln Asn Lys Phe Ile
                85                  90                  95

Met Leu Asn Leu Met His Glu Thr Thr Asp Lys Asn Leu Ser Pro Asp
                100                 105                 110

Gly Gln Tyr Val Pro Arg Ile Met Phe Val Asp Pro Ser Leu Thr Val
            115                 120                 125

Arg Ala Asp Ile Ala Gly Arg Tyr Ser Asn Arg Leu Tyr Thr Tyr Glu
        130                 135                 140

Pro Arg Asp Leu Pro Leu Leu Ile Glu Asn Met Lys Lys Ala Leu Arg
145                 150                 155                 160

Leu Ile Gln Ser Glu Leu
                165

<210> SEQ ID NO 5
<211> LENGTH: 767
<212> TYPE: DNA
<213> ORGANISM: Homo sapiens

<400> SEQUENCE: 5
agaaacatcc agaatacatt tccaacaaga gcactggcca agtcagcttc ttctgagaga      60
gtctctagaa gacatgatgc tacactcagc tttgggtctc tgcctcttac tcgtcacagt     120
ttcttccaac cttgccattg caataaaaaa ggaaaagagg cctcctcaga cactctcaag     180
aggatgggga gatgacatca cttgggtaca aacttatgaa gaaggtctct tttatgctca     240
aaaaagtaag aagccattaa tggttattca tcacctggag gattgtcaat actctcaagc     300
actaaagaaa gtatttgccc aaaatgaaga aatacaagaa atggctcaga taagttcat     360 catgctaaac cttatgcatg aaaccactga taagaattta tcacctgatg ggcaatatgt     420
gcctagaatc atgtttgtag acccttcttt aacagttaga gctgacatag ctggaagata     480
ctctaacaga ttgtacacat atgagcctcg ggatttaccc ctattgatag aaaacatgaa     540
gaaagcatta agacttattc agtcagagct ataagagatg atggaaaaaa gccttcactt     600
caaagaagtc aaatttcatg aagaaaacct ctggcacatt gacaaatact aaatgtgcaa     660
gtatatagat tttgtaatat tactatttag tttttttaat gtgtttgcaa tagtcttatt     720

-continued

```
aaaataaatg tttttaaat ctgagactga aaaaaaaaaa aaaaaaa                    767
```

<210> SEQ ID NO 6
<211> LENGTH: 7
<212> TYPE: PRT
<213> ORGANISM: Artificial Sequence
<220> FEATURE:
<223> OTHER INFORMATION: AGR3 peptides

<400> SEQUENCE: 6

Leu Tyr Thr Tyr Glu Pro Arg
1               5

<210> SEQ ID NO 7
<211> LENGTH: 11
<212> TYPE: PRT
<213> ORGANISM: Artificial Sequence
<220> FEATURE:
<223> OTHER INFORMATION: AGR3 peptide

<400> SEQUENCE: 7

Asn Leu Ser Pro Asp Gly Gln Tyr Val Pro Arg
1               5                   10

<210> SEQ ID NO 8
<211> LENGTH: 15
<212> TYPE: PRT
<213> ORGANISM: Artificial Sequence
<220> FEATURE:
<223> OTHER INFORMATION: AGR3 peptide

<400> SEQUENCE: 8

Val Phe Ala Gln Asn Glu Glu Ile Gln Glu Met Ala Gln Asn Lys
1               5                   10                  15

<210> SEQ ID NO 9
<211> LENGTH: 8
<212> TYPE: PRT
<213> ORGANISM: Artificial Sequence
<220> FEATURE:
<223> OTHER INFORMATION: AGR3 peptide

<400> SEQUENCE: 9

Arg Pro Pro Gln Thr Leu Ser Arg
1               5

<210> SEQ ID NO 10
<211> LENGTH: 227
<212> TYPE: PRT
<213> ORGANISM: Homo sapiens

<400> SEQUENCE: 10

Met Lys Gln Ile Leu His Pro Ala Leu Glu Thr Thr Ala Met Thr Leu
1               5                   10                  15

Phe Pro Val Leu Leu Phe Leu Val Ala Gly Leu Leu Pro Ser Phe Pro
                20                  25                  30

Ala Asn Glu Asp Lys Asp Pro Ala Phe Thr Ala Leu Leu Thr Thr Gln
        35                  40                  45

Thr Gln Val Gln Arg Glu Ile Val Asn Lys His Asn Glu Leu Arg Arg
    50                  55                  60

Ala Val Ser Pro Pro Ala Arg Asn Met Leu Lys Met Glu Trp Asn Lys
65                  70                  75                  80

Glu Ala Ala Ala Asn Ala Gln Lys Trp Ala Asn Gln Cys Asn Tyr Arg

```
                      85                  90                  95
His Ser Asn Pro Lys Asp Arg Met Thr Ser Leu Lys Cys Gly Glu Asn
                100                 105                 110
Leu Tyr Met Ser Ser Ala Pro Ser Ser Trp Ser Gln Ala Ile Gln Ser
            115                 120                 125
Trp Phe Asp Glu Tyr Asn Asp Phe Asp Phe Gly Val Gly Pro Lys Thr
        130                 135                 140
Pro Asn Ser Val Val Gly His Tyr Thr Gln Val Val Trp Tyr Ser Ser
145                 150                 155                 160
Tyr Leu Val Gly Cys Gly Asn Ala Tyr Cys Pro Asn Gln Lys Val Leu
                165                 170                 175
Lys Tyr Tyr Tyr Val Cys Gln Tyr Cys Pro Ala Gly Asn Trp Ala Asn
                180                 185                 190
Arg Leu Tyr Val Pro Tyr Glu Gln Gly Ala Pro Cys Ala Ser Cys Pro
            195                 200                 205
Asp Asn Cys Asp Asp Gly Leu Cys Ser Lys Phe Glu Val Ile Asn Leu
        210                 215                 220
Ile Ile Lys
225

<210> SEQ ID NO 11
<211> LENGTH: 1162
<212> TYPE: DNA
<213> ORGANISM: Homo sapiens

<400> SEQUENCE: 11
ctggaaacca ctgcaatgac attattccca gtgctgttgt tcctggttgc tgggctgctt      60
ccatcttttc cagcaaatga agataaggat cccgctttta ctgctttgtt aaccacccaa     120
acacaagtgc aaagggagat tgtgaataag cacaatgaac tgaggagagc agtatctccc     180
cctgccagaa acatgctgaa gatggaatgg aacaaagagg ctgcagcaaa tgcccaaaag     240
tgggcaaacc agtgcaatta cagacacagt aacccaaagg atcgaatgac aagtctaaaa     300
tgtggtgaga tctctacat gtcaagtgcc tccagctcat ggtcacaagc aatccaaagc     360
tggtttgatg agtacaatga ttttgacttt ggtgtagggc caaagactcc caacgcagtg     420
gttggacatt atacacaggt tgtttggtac tcttcatacc tcgttggatg tggaaatgcc     480
tactgtccca tcaaaaagt tctaaaatac tactatgttt gccaatattg tcctgctggt     540
aattgggcta atagactata tgtcccttat gaacaaggag caccttgtgc cagttgccca     600
gataactgtg acgatggact atgcaccaat ggttgcaagt acgaagatct ctatagtaac     660
tgtaaaagtt tgaagctcac attaacctgt aaacatcagt tggtcaggga cagttgcaag     720
gcctcctgca attgttcaaa cagcatttat taaatacgca ttacacaccg gtagggcta     780 tgtagagagg agtcagatta tctacttaga tttggcatct acttagattt aacatatact     840
agctgagaaa ttgtaggcat gtttgataca catttgattt caaatgtttt tcttctggat     900 ctgctttta ttttacaaaa atatttttca tacaaatggt taaaagaaa caaaatctat      960 aacaacaact ttggattttt atatataaac tttgtgattt aaatttactg aatttaatta    1020
gggtgaaaat tttgaaagtt gtattctcat atgactaagt tcactaaaac cctggattga    1080
aagtgaaaat tatgttccta gaacaaaatg tacaaaaaga acaatataat tttcacatga    1140
acccttggct gtagttgcct tt                                              1162

<210> SEQ ID NO 12
```

```
<211> LENGTH: 8
<212> TYPE: PRT
<213> ORGANISM: Artificial Sequence
<220> FEATURE:
<223> OTHER INFORMATION: CRISP3 peptide

<400> SEQUENCE: 12

Trp Ala Asn Gln Cys Asn Tyr Arg
1               5

<210> SEQ ID NO 13
<211> LENGTH: 9
<212> TYPE: PRT
<213> ORGANISM: Artificial Sequence
<220> FEATURE:
<223> OTHER INFORMATION: CRISP3 peptide

<400> SEQUENCE: 13

Tyr Glu Asp Leu Tyr Ser Asn Cys Lys
1               5

<210> SEQ ID NO 14
<211> LENGTH: 17
<212> TYPE: PRT
<213> ORGANISM: Artificial Sequence
<220> FEATURE:
<223> OTHER INFORMATION: CRISP3 peptide

<400> SEQUENCE: 14

Tyr Tyr Tyr Val Cys Gln Tyr Cys Pro Ala Gly Asn Asn Trp Ala Asn
1               5                   10                  15

Arg

<210> SEQ ID NO 15
<211> LENGTH: 20
<212> TYPE: PRT
<213> ORGANISM: Artificial Sequence
<220> FEATURE:
<223> OTHER INFORMATION: CRISP3 peptide

<400> SEQUENCE: 15

Asn Glu Asp Lys Asp Pro Ala Phe Thr Ala Leu Leu Thr Thr Gln Thr
1               5                   10                  15

Gln Val Gln Arg
            20

<210> SEQ ID NO 16
<211> LENGTH: 92
<212> TYPE: PRT
<213> ORGANISM: Homo sapiens

<400> SEQUENCE: 16

Met Gln Val Ser Thr Ala Ala Leu Ala Val Leu Leu Cys Thr Met Ala
1               5                   10                  15

Leu Cys Asn Gln Phe Ser Ala Ser Leu Ala Ala Asp Thr Pro Thr Ala
                20                  25                  30

Cys Cys Phe Ser Tyr Thr Ser Arg Gln Ile Pro Gln Asn Phe Ile Ala
            35                  40                  45

Asp Tyr Phe Glu Thr Ser Ser Gln Cys Ser Lys Pro Gly Val Ile Phe
        50                  55                  60

Leu Thr Lys Arg Ser Arg Gln Val Cys Ala Asp Pro Ser Glu Glu Trp
65                  70                  75                  80

Val Gln Lys Tyr Val Ser Asp Leu Glu Leu Ser Ala
```

<210> SEQ ID NO 17
<211> LENGTH: 813
<212> TYPE: DNA
<213> ORGANISM: Homo sapiens

<400> SEQUENCE: 17

```
agctggtttc agacttcaga aggacacggg cagcagacag tggtcagtcc tttcttggct      60
ctgctgacac tcgagcccac attccgtcac ctgctcagaa tcatgcaggt ctccactgct     120
gcccttgctg tcctcctctg caccatggct ctctgcaacc agttctctgc atcacttgct     180
gctgacacgc cgaccgcctg ctgcttcagc tacacctccc ggcagattcc acagaatttc     240
atagctgact actttgagac gagcagccag tgctccaagc ccggtgtcat cttcctaacc     300
aagcgaagcc ggcaggtctg tgctgacccc agtgaggagt gggtccagaa atatgtcagc     360
gacctggagc tgagtgcctg aggggtccag aagcttcgag gcccagcgac ctcggtgggc     420
ccagtgggga ggagcaggag cctgagcctt gggaacatgc gtgtgacctc acagctaccc     480
tcttctatgg actggttgtt gccaaacagc cacactgtgg gactcttctt aacttaaatt     540
ttaatttatt tatactattt agtttttgta atttattttc gatttcacag tgtgtttgtg     600
attgtttgct ctgagagttc ccctgtcccc tcccccttcc ctcacaccgc gtctggtgac     660
aaccgagtgg ctgtcatcag cctgtgtagg cagtcatggc accaaagcca ccagactgac     720
aaatgtgtat cggatgcttt tgttcagggc tgtgatcggc ctggggaaat aataaagatg     780
ctcttttaaa aggtaaaaaa aaaaaaaaaa aaa                                  813
```

<210> SEQ ID NO 18
<211> LENGTH: 13
<212> TYPE: PRT
<213> ORGANISM: Artificial Sequence
<220> FEATURE:
<223> OTHER INFORMATION: CCL3 peptide

<400> SEQUENCE: 18

Gln Val Cys Ala Asp Pro Ser Glu Glu Trp Val Gln Lys
1               5                   10

<210> SEQ ID NO 19
<211> LENGTH: 19
<212> TYPE: PRT
<213> ORGANISM: Artificial Sequence
<220> FEATURE:
<223> OTHER INFORMATION: CCL3 peptide

<400> SEQUENCE: 19

Gln Ile Pro Gln Asn Phe Ile Ala Asp Tyr Phe Glu Thr Ser Ser Gln
1               5                   10                  15

Cys Ser Lys

<210> SEQ ID NO 20
<211> LENGTH: 9
<212> TYPE: PRT
<213> ORGANISM: Artificial Sequence
<220> FEATURE:
<223> OTHER INFORMATION: CCL3 peptide

<400> SEQUENCE: 20

Tyr Val Ser Asp Leu Glu Leu Ser Ala
1               5

<210> SEQ ID NO 21
<211> LENGTH: 702
<212> TYPE: PRT
<213> ORGANISM: Homo sapiens

<400> SEQUENCE: 21

```
Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
    50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
    210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Thr Cys Gln Ala His Asn Ser
    290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
            340                 345                 350

Thr Tyr Leu Trp Trp Val Asn Asn Gln Ser Leu Pro Val Ser Pro Arg
        355                 360                 365

Leu Gln Leu Ser Asn Asp Asn Arg Thr Leu Thr Leu Leu Ser Val Thr
    370                 375                 380
```

```
Arg Asn Asp Val Gly Pro Tyr Glu Cys Gly Ile Gln Asn Glu Leu Ser
385                 390                 395                 400

Val Asp His Ser Asp Pro Val Ile Leu Asn Val Leu Tyr Gly Pro Asp
            405                 410                 415

Asp Pro Thr Ile Ser Pro Ser Tyr Thr Tyr Tyr Arg Pro Gly Val Asn
        420                 425                 430

Leu Ser Leu Ser Cys His Ala Ala Ser Asn Pro Pro Ala Gln Tyr Ser
            435                 440                 445

Trp Leu Ile Asp Gly Asn Ile Gln Gln His Thr Gln Glu Leu Phe Ile
        450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
            485                 490                 495

Ser Ala Glu Leu Pro Lys Pro Ser Ile Ser Ser Asn Asn Ser Lys Pro
        500                 505                 510

Val Glu Asp Lys Asp Ala Val Ala Phe Thr Cys Glu Pro Glu Ala Gln
        515                 520                 525

Asn Thr Thr Tyr Leu Trp Trp Val Asn Gly Gln Ser Leu Pro Val Ser
530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
            565                 570                 575

Val Ser Ala Asn Arg Ser Asp Pro Val Thr Leu Asp Val Leu Tyr Gly
            580                 585                 590

Pro Asp Thr Pro Ile Ile Ser Pro Pro Asp Ser Ser Tyr Leu Ser Gly
        595                 600                 605

Ala Asn Leu Asn Leu Ser Cys His Ser Ala Ser Asn Pro Ser Pro Gln
        610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Asn Gly Thr Tyr Ala Cys Phe
            645                 650                 655

Val Ser Asn Leu Ala Thr Gly Arg Asn Asn Ser Ile Val Lys Ser Ile
            660                 665                 670

Thr Val Ser Ala Ser Gly Thr Ser Pro Gly Leu Ser Ala Gly Ala Thr
            675                 680                 685

Val Gly Ile Met Ile Gly Val Leu Val Gly Val Ala Leu Ile
        690                 695                 700

<210> SEQ ID NO 22
<211> LENGTH: 3542
<212> TYPE: DNA
<213> ORGANISM: Homo sapiens

<400> SEQUENCE: 22
gatgctgaga agtactcctg ccctaggaag agactcaggg cagagggagg aaggacagca    60
gaccagacag tcacagcagc cttgacaaaa cgttcctgga actcaagctc ttctccacag   120
aggaggacag agcagacagc agagaccatg agtctccct cggcccctcc ccacagatgg    180
tgcatcccct ggcagaggct cctgctcaca gcctcacttc taaccttctg gaacccgccc   240
accactgcca agctcactat tgaatccacg ccgttcaatg tcgcagaggg gaaggaggtg   300
```

```
cttctacttg tccacaatct gccccagcat ctttttggct acagctggta caaaggtgaa    360
agagtggatg caaccgtca aattatagga tatgtaatag aactcaaca agctacccca     420 gggcccgcat acagtggtcg agagataata taccccaatg catccctgct gatccagaac    480
atcatccaga atgacacagg attctacacc ctacacgtca taaagtcaga tcttgtgaat    540
gaagaagcaa ctggccagtt ccgggtatac ccggagctgc ccaagccctc catctccagc    600
aacaactcca aacccgtgga ggacaaggat gctgtggcct tcacctgtga acctgagact    660
caggacgcaa cctacctgtg gtgggtaaac aatcagagcc tcccggtcag tcccaggctg    720
cagctgtcca atggcaacag gaccctcact ctattcaatg tcacaagaaa tgacacagca    780
agctacaaat gtgaaaccca gaacccagtg agtgccaggc gcagtgattc agtcatcctg    840
aatgtcctct atggcccgga tgcccccacc atttcccctc taaacacatc ttacagatca    900
ggggaaaatc tgaacctctc ctgccacgca gcctctaacc cacctgcaca gtactcttgg    960
tttgtcaatg ggacttttcca gcaatccacc caagagctct ttatcccaa catcactgtg   1020 aataatagtg gatcctatac gtgccaagcc cataactcag acactggcct caataggacc   1080
acagtcacga cgatcacagt ctatgcagag ccacccaaac ccttcatcac cagcaacaac   1140
tccaaccccg tggaggatga ggatgctgta gccttaacct gtgaacctga gattcagaac   1200
acaacctacc tgtggtgggt aaataatcag agcctcccgg tcagtcccag gctgcagctg   1260
tccaatgaca acaggaccct cactctactc agtgtcacaa ggaatgatgt aggaccctat   1320
gagtgtggaa tccagaacga attaagtgtt gaccacagcg acccagtcat cctgaatgtc   1380
ctctatggcc cagacgaccc caccatttcc ccctcataca cctattaccg tccaggggtg   1440
aacctcagcc tctcctgcca tgcagcctct aacccacctg cacagtattc ttggctgatt   1500
gatgggaaca tccagcaaca cacacaagag ctctttatct ccaacatcac tgagaagaac   1560
agcggactct atacctgcca ggccaataac tcagccagtg gccacagcag gactacagtc   1620
aagacaatca cagtctctgc ggagctgccc aagccctcca tctccagcaa caactccaaa   1680
cccgtggagg acaaggatgc tgtggccttc acctgtgaac ctgaggctca gaacacaacc   1740
tacctgtggt gggtaaatgg tcagagcctc ccagtcagtc caggctgca gctgtccaat   1800 ggcaacagga ccctcactct attcaatgtc acaagaaatg acgcaagagc ctatgtatgt   1860
ggaatccaga actcagtgag tgcaaaccgc agtgacccag tcaccctgga tgtcctctat   1920
gggccggaca cccccatcat ttcccccca gactcgtctt acctttcggg agcgaacctc   1980
aacctctcct gccactcggc ctctaaccca tcccgcagt attcttggcg tatcaatggg    2040
ataccgcagc aacacacaca agttctcttt atcgccaaaa tcacgccaaa taataacggg   2100
acctatgcct gttttgtctc taacttggct actggccgca ataattccat agtcaagagc   2160
atcacagtct ctgcatctgg aacttctcct ggtctctcag ctggggccac tgtcggcatc   2220
atgattggag tgctggttgg ggttgctctg atatagcagc cctggtgtag tttcttcatt   2280
tcaggaagac tgacagttgt tttgcttctt ccttaaagca tttgcaacag ctacagtcta   2340
aaattgcttc tttaccaagg atatttacag aaaagactct gaccagagat cgagaccatc   2400
ctagccaaca tcgtgaaacc ccatctctac taaaaataca aaaatgagct gggcttggtg   2460
gcgcacacct gtagtcccag ttactcggga ggctgaggca ggagaatcgc ttgaacccgg   2520
gaggtggaga ttgcagtgag cccagatcgc accactgcac tccagtctgg caacagagca   2580
agactccatc tcaaaaagaa aagaaaagaa gactctgacc tgtactcttg aatcaagttt   2640
tctgatacca ctgcactgtc tgagaatttc caaaactta atgaactaac tgacagcttc   2700
```

```
atgaaactgt ccaccaagat caagcagaga aaataattaa tttcatggga ctaaatgaac    2760
taatgaggat aatattttca aattttttta tttgaaattt tgctgattct ttaaatgtct    2820
tgtttcccag atttcaggaa actttttttc ttttaagcta tccacagctt acagcaattt    2880
gataaaatat acttttgtga acaaaaattg agacatttac attttctccc tatgtggtcg    2940
ctccagactt gggaaactat tcatgaatat ttatattgta tggtaatata gttattgcac    3000
aagttcaata aaaatctgct ctttgtatga cagaatacat ttgaaaacat tggttatatt    3060
accaagactt tgactagaat gtcgtatttg aggatataaa cccataggta ataaacccac    3120
aggtactaca aacaaagtct gaagtcagcc ttggtttggc ttcctagtgt caattaaact    3180
tctaaaagtt taatctgaga ttccttataa aacttccag caaagcaact ttaaaaagt     3240 ctgtgtgggc cgggcgcggt ggctcacgcc tgtaatccca gcactttgat ccgccgaggc    3300
gggcggatca cgaggtcagg agatccagac catcctggct aacacagtga aaccccgtct    3360
ctactaaaaa tacaaaaaaa gttagccggg cgtggtggtg ggggcctgta gtcccagcta    3420
ctcaggaggc tgaggcagga gaacggcatg aacccgggag gcagggcttg cagtgagcca    3480
agatcatgcc gctgcactcc agcctgggag acaaagtgag actccgtcaa aaaaaaaaa    3540 aa                                                                   3542
```

<210> SEQ ID NO 23
<211> LENGTH: 13
<212> TYPE: PRT
<213> ORGANISM: Artificial Sequence
<220> FEATURE:
<223> OTHER INFORMATION: CEACAM5 peptide

<400> SEQUENCE: 23

Ser Asp Leu Val Asn Glu Glu Ala Thr Gly Gln Phe Arg
1               5                   10

<210> SEQ ID NO 24
<211> LENGTH: 16
<212> TYPE: PRT
<213> ORGANISM: Artificial Sequence
<220> FEATURE:
<223> OTHER INFORMATION: CEACAM5 peptide

<400> SEQUENCE: 24

Ile Asn Gly Ile Pro Gln Gln His Thr Gln Val Leu Phe Ile Ala Lys
1               5                   10                  15

<210> SEQ ID NO 25
<211> LENGTH: 10
<212> TYPE: PRT
<213> ORGANISM: Artificial Sequence
<220> FEATURE:
<223> OTHER INFORMATION: CEACAM5 peptide

<400> SEQUENCE: 25

Cys Glu Thr Gln Asn Pro Val Ser Ala Arg
1               5                   10

<210> SEQ ID NO 26
<211> LENGTH: 14
<212> TYPE: PRT
<213> ORGANISM: Artificial Sequence
<220> FEATURE:
<223> OTHER INFORMATION: CEACAM5 peptide

<400> SEQUENCE: 26

Ala Tyr Val Cys Gly Ile Gln Asn Ser Val Ser Ala Asn Arg
1               5                   10

<210> SEQ ID NO 27
<211> LENGTH: 344
<212> TYPE: PRT
<213> ORGANISM: Homo sapiens

<400> SEQUENCE: 27

Met Gly Pro Pro Ser Ala Pro Pro Cys Arg Leu His Val Pro Trp Lys
1               5                   10                  15

Glu Val Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Ala His Asn Leu Pro Gln Asn Arg Ile Gly
    50                  55                  60

Tyr Ser Trp Tyr Lys Gly Glu Arg Val Asp Gly Asn Ser Leu Ile Val
65                  70                  75                  80

Gly Tyr Val Ile Gly Thr Gln Gln Ala Thr Pro Gly Pro Ala Tyr Ser
                85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Val Gln Asn Thr Thr Tyr
                165                 170                 175

Leu Trp Trp Val Asn Gly Gln Ser Leu Pro Val Ser Pro Arg Leu Gln
            180                 185                 190

Leu Ser Asn Gly Asn Met Thr Leu Thr Leu Leu Ser Val Lys Arg Asn
        195                 200                 205

Asp Ala Gly Ser Tyr Glu Cys Glu Ile Gln Asn Pro Ala Ser Ala Asn
    210                 215                 220

Arg Ser Asp Pro Val Thr Leu Asn Val Leu Tyr Gly Pro Asp Val Pro
225                 230                 235                 240

Thr Ile Ser Pro Ser Lys Ala Asn Tyr Arg Pro Gly Glu Asn Leu Asn
                245                 250                 255

Leu Ser Cys His Ala Ala Ser Asn Pro Pro Ala Gln Tyr Ser Trp Phe
            260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Met Cys Gln Ala His Asn Ser
    290                 295                 300

Ala Thr Gly Leu Asn Arg Thr Thr Val Thr Met Ile Thr Val Ser Gly
305                 310                 315                 320

Ser Ala Pro Val Leu Ser Ala Val Ala Thr Val Gly Ile Thr Ile Gly
                325                 330                 335

Val Leu Ala Arg Val Ala Leu Ile
            340

<210> SEQ ID NO 28
<211> LENGTH: 2601
<212> TYPE: DNA
<213> ORGANISM: Homo sapiens

<400> SEQUENCE: 28

| | | | | | | |
|---|---|---|---|---|---|---|
| gaggctcagc | acagaaggag | gaaggacagc | agggccaaca | gtcacagcag | ccctgaccag | 60 |
| agcattcctg | gagctcaagc | tcctctacaa | agaggtggac | agagaagaca | gcagagacca | 120 |
| tgggaccccc | ctcagcccct | ccctgcagat | tgcatgtccc | ctggaaggag | gtcctgctca | 180 |
| cagcctcact | tctaaccttc | tggaacccac | ccaccactgc | caagctcact | attgaatcca | 240 |
| cgccgttcaa | tgtcgcagag | gggaaggagg | ttcttctact | cgcccacaac | ctgccccaga | 300 |
| atcgtattgg | ttacagctgg | tacaaaggcg | aaagagtgga | tggcaacagt | ctaattgtag | 360 |
| gatatgtaat | aggaactcaa | caagctaccc | cagggcccgc | atacagtggt | cgagagacaa | 420 |
| tataccccaa | tgcatccctg | ctgatccaga | acgtcaccca | gaatgacaca | ggattctata | 480 |
| ccctacaagt | cataaagtca | gatcttgtga | atgaagaagc | aaccggacag | ttccatgtat | 540 |
| acccggagct | gcccaagccc | tccatctcca | gcaacaactc | caaccccgtg | gaggacaagg | 600 |
| atgctgtggc | cttcacctgt | gaacctgagg | ttcagaacac | aacctacctg | tggtgggtaa | 660 |
| atggtcagag | cctcccggtc | agtcccaggc | tgcagctgtc | caatggcaac | atgaccctca | 720 |
| ctctactcag | cgtcaaaagg | aacgatgcag | gatcctatga | atgtgaaata | cagaacccag | 780 |
| cgagtgccaa | ccgcagtgac | ccagtcaccc | tgaatgtcct | ctatggccca | gatgtcccca | 840 |
| ccatttcccc | ctcaaaggcc | aattaccgtc | caggggaaaa | tctgaacctc | tcctgccacg | 900 |
| cagcctctaa | cccacctgca | cagtactctt | ggtttatcaa | tgggacgttc | cagcaatcca | 960 |
| cacaagagct | ctttatcccc | aacatcactg | tgaataatag | cggatcctat | atgtgccaag | 1020 |
| cccataactc | agccactggc | ctcaatagga | ccacagtcac | gatgatcaca | gtctctggaa | 1080 |
| gtgctcctgt | cctctcagct | gtggccaccg | tcggcatcac | gattggagtg | ctggccaggg | 1140 |
| tggctctgat | atagcagccc | tggtgtattt | tcgatatttc | aggaagactg | gcagattgga | 1200 |
| ccagaccctg | aattcttcta | gctcctccaa | tcccatttta | tcccatggaa | ccactaaaaa | 1260 |
| caaggtctgc | tctgctcctg | aagccctata | tgctggagat | ggacaactca | atgaaaattt | 1320 |
| aaagggaaaa | ccctcaggcc | tgaggtgtgt | gccactcaga | gacttcacct | aactagagac | 1380 |
| agtcaaactg | caaaccatgg | tgagaaattg | acgacttcac | actatggaca | gcttttccca | 1440 |
| agatgtcaaa | acaagactcc | tcatcatgat | aaggctctta | ccccctttta | atttgtcctt | 1500 |
| gcttatgcct | gcctctttcg | cttggcagga | tgatgctgtc | attagtattt | cacaagaagt | 1560 |
| agcttcagag | ggtaacttaa | cagagtgtca | gatctatctt | gtcaatccca | acgttttaca | 1620 |
| taaaataaga | gatccctttag | tgcacccagt | gactgacatt | agcagcatct | ttaacacagc | 1680 |
| cgtgtgttca | aatgtacagt | ggtccttttc | agagttggac | ttctagactc | acctgttctc | 1740 |
| actccctgtt | ttaattcaac | ccagccatgc | aatgccaaat | aatagaattg | ctccctacca | 1800 |
| gctgaacagg | gaggagtctg | tgcagtttct | gacacttgtt | gttgaacatg | gctaaataca | 1860 |
| atgggtatcg | ctgagactaa | gttgtagaaa | ttaacaaatg | tgctgcttgg | ttaaaatggc | 1920 |
| tacactcatc | tgactcattc | tttattctat | tttagttggt | ttgtatcttg | cctaaggtgc | 1980 |
| gtagtccaac | tcttggtatt | accctcctaa | tagtcatact | agtagtcata | ctccctggtg | 2040 |
| tagtgtattc | tctaaaagct | ttaaatgtct | gcatgcagcc | agccatcaaa | tagtgaatgg | 2100 |
| tctctctttg | gctggaatta | caaaactcag | agaaatgtgt | catcaggaga | acatcataac | 2160 |

```
ccatgaagga taaaagcccc aaatggtggt aactgataat agcactaatg ctttaagatt    2220
tggtcacact ctcacctagg tgagcgcatt gagccagtgg tgctaaatgc tacatactcc    2280
aactgaaatg ttaaggaaga agatagatcc aattaaaaaa aattaaaacc aatttaaaaa    2340
aaaaaagaac acaggagatt ccagtctact tgagttagca taatacagaa gtcccctcta    2400
ctttaacttt tacaaaaaag taacctgaac taatctgatg ttaaccaatg tatttatttc    2460
tgtggttctg tttccttgtt ccaatttgac aaaacccact gttcttgtat tgtattgccc    2520
agggggagct atcactgtac ttgtagagtg gtgctgcttt aattcataaa tcacaaataa    2580
aagccaatta gctctataac t                                              2601
```

<210> SEQ ID NO 29
<211> LENGTH: 13
<212> TYPE: PRT
<213> ORGANISM: Artificial Sequence
<220> FEATURE:
<223> OTHER INFORMATION: CEACAM6 peptide

<400> SEQUENCE: 29

Glu Val Leu Leu Leu Ala His Asn Leu Pro Gln Asn Arg
1               5                   10

<210> SEQ ID NO 30
<211> LENGTH: 21
<212> TYPE: PRT
<213> ORGANISM: Artificial Sequence
<220> FEATURE:
<223> OTHER INFORMATION: CEACAM6 peptide

<400> SEQUENCE: 30

Ser Asp Pro Val Thr Leu Asn Val Leu Tyr Gly Pro Asp Gly Pro Thr
1               5                   10                  15

Ile Ser Pro Ser Lys
            20

<210> SEQ ID NO 31
<211> LENGTH: 18
<212> TYPE: PRT
<213> ORGANISM: Artificial Sequence
<220> FEATURE:
<223> OTHER INFORMATION: CEACAM6 peptide

<400> SEQUENCE: 31

Asn Asp Ala Gly Ser Tyr Glu Cys Glu Ile Gln Asn Pro Ala Ser Ala
1               5                   10                  15

Asn Arg

<210> SEQ ID NO 32
<211> LENGTH: 206
<212> TYPE: PRT
<213> ORGANISM: Homo sapiens

<400> SEQUENCE: 32

Met Asn Phe Gln Gln Arg Leu Gln Ser Leu Trp Thr Leu Ala Arg Pro
1               5                   10                  15

Phe Cys Pro Pro Leu Leu Ala Thr Ala Ser Gln Met Gln Met Val Val
                20                  25                  30

Leu Pro Cys Leu Gly Phe Thr Leu Leu Leu Trp Ser Gln Val Ser Gly
            35                  40                  45

Ala Gln Gly Gln Glu Phe His Phe Gly Pro Cys Gln Val Lys Gly Val
        50                  55                  60

```
Val Pro Gln Lys Leu Trp Glu Ala Phe Trp Ala Val Lys Asp Thr Met
 65                  70                  75                  80

Gln Ala Gln Asp Asn Ile Thr Ser Ala Arg Leu Leu Gln Gln Glu Val
                 85                  90                  95

Leu Gln Asn Val Ser Asp Ala Glu Ser Cys Tyr Leu Val His Thr Leu
            100                 105                 110

Leu Glu Phe Tyr Leu Lys Thr Val Phe Lys Asn Tyr His Asn Arg Thr
        115                 120                 125

Val Glu Val Arg Thr Leu Lys Ser Phe Ser Thr Leu Ala Asn Asn Phe
    130                 135                 140

Val Leu Ile Val Ser Gln Leu Gln Pro Ser Gln Glu Asn Glu Met Phe
145                 150                 155                 160

Ser Ile Arg Asp Ser Ala His Arg Arg Phe Leu Leu Phe Arg Arg Ala
                165                 170                 175

Phe Lys Gln Leu Asp Val Glu Ala Ala Leu Thr Lys Ala Leu Gly Glu
            180                 185                 190

Val Asp Ile Leu Leu Thr Trp Met Gln Lys Phe Tyr Lys Leu
        195                 200                 205

<210> SEQ ID NO 33
<211> LENGTH: 1976
<212> TYPE: DNA
<213> ORGANISM: Homo sapiens

<400> SEQUENCE: 33
gcttgcctgc aaacctttac ttctgaaatg acttccacgg ctgggacggg aaccttccac     60
ccacagctat gcctctgatt ggtgaatggt gaaggtgcct gtctaacttt tctgtaaaaa    120
gaaccagctg cctccaggca gccagccctc aagcatcact tacaggacca gagggacaag    180
acatgactgt gatgaggagc tgctttcgcc aatttaacac caagaagaat tgaggctgct    240
tgggaggaag gccaggagga acacgagact gagagatgaa ttttcaacag aggctgcaaa    300
gcctgtggac tttagccaga cccttctgcc ctcctttgct ggcgacagcc tctcaaatgc    360
agatggttgt gctcccttgc ctgggtttta ccctgcttct ctggagccag gtatcagggg    420
cccagggcca agaattccac tttgggccct gccaagtgaa gggggttgtt ccccagaaac    480
tgtgggaagc cttctgggct gtgaaagaca ctatgcaagc tcaggataac atcacgagtg    540
cccggctgct gcagcaggag gttctgcaga acgtctcgga tgctgagagc tgttaccttg    600
tccacaccct gctggagttc tacttgaaaa ctgttttcaa aaactaccac aatagaacag    660
ttgaagtcag gactctgaag tcattctcta ctctggccaa caactttgtt ctcatcgtgt    720
cacaactgca acccagtcaa gaaaatgaga tgttttccat cagagacagt gcacacaggc    780
ggtttctgct attccggaga gcattcaaac agttggacgt agaagcagct ctgaccaaag    840
cccttgggga gtggacatt cttctgacct ggatgcagaa attctacaag ctctgaatgt    900
ctagaccagg acctccctcc ccctggcact ggtttgttcc ctgtgtcatt tcaaacagtc    960
tcccttccta tgctgttcac tggacacttc acgcccttgg ccatgggtcc cattcttggc   1020
ccaggattat tgtcaaagaa gtcattcttt aagcagcgcc agtgacagtc agggaaggtg   1080
cctctggatg ctgtgaagag tctacagaga agattcttgt atttattaca actctattta   1140
attaatgtca gtatttcaac tgaagttcta tttatttgtg agactgtaag ttacatgaag   1200
gcagcagaat attgtgcccc atgcttcttt accectcaca atccttgcca cagtgtgggg   1260
cagtggatgg gtgcttagta agtacttaat aaactgtggt gcttttttg gcctgtcttt   1320
```

```
ggattgttaa aaaacagaga gggatgcttg gatgtaaaac tgaacttcag agcatgaaaa    1380
tcacactgtc ttctgatatc tgcagggaca gagcattggg gtgggggtaa ggtgcatctg    1440
tttgaaaagt aaacgataaa atgtggatta aagtgcccag cacaaagcag atcctcaata    1500
aacatttcat ttcccaccca cactcgccag ctcaccccat catccctttc ccttggtgcc    1560 ctccttttt ttttatccta gtcattcttc cctaatcttc cacttgagtg tcaagctgac     1620
cttgctgatg gtgacattgc acctggatgt actatccaat ctgtgatgac attccctgct    1680
aataaaagac aacataactc aagtctggca gactttcttc tctatttctg atgaatgcc     1740 cagtgagact gtgttgtaca gctagaaaag gccttcttcc caatagcaag gctgtgcatc    1800
tagcctcaag ctctggctga actttgtggt cgacatcaat ctaaagatac agtgtctgac    1860
tataaccttg ttccaaaaac ctaggcaaag agtatatgta ggaggtggga tatcacttcc    1920
atgacataag tgctattgca gagccgtggc cacccaggaa ctcctgactg ctttcc        1976

<210> SEQ ID NO 34
<211> LENGTH: 9
<212> TYPE: PRT
<213> ORGANISM: Artificial Sequence
<220> FEATURE:
<223> OTHER INFORMATION: IL24 peptide

<400> SEQUENCE: 34

Leu Trp Glu Ala Phe Trp Ala Val Lys
1               5

<210> SEQ ID NO 35
<211> LENGTH: 10
<212> TYPE: PRT
<213> ORGANISM: Artificial Sequence
<220> FEATURE:
<223> OTHER INFORMATION: IL24 peptide

<400> SEQUENCE: 35

Gln Leu Asp Val Glu Ala Ala Leu Thr Lys
1               5                   10

<210> SEQ ID NO 36
<211> LENGTH: 14
<212> TYPE: PRT
<213> ORGANISM: Artificial Sequence
<220> FEATURE:
<223> OTHER INFORMATION: IL24 peptide

<400> SEQUENCE: 36

Ala Leu Gly Glu Val Asp Ile Leu Leu Thr Trp Met Gln Lys
1               5                   10

<210> SEQ ID NO 37
<211> LENGTH: 6
<212> TYPE: PRT
<213> ORGANISM: Artificial Sequence
<220> FEATURE:
<223> OTHER INFORMATION: IL24 peptide

<400> SEQUENCE: 37

Gly Val Val Pro Gln Lys
1               5

<210> SEQ ID NO 38
<211> LENGTH: 707
<212> TYPE: PRT
```

-continued

<213> ORGANISM: Homo sapiens

<400> SEQUENCE: 38

Met Ser Leu Trp Gln Pro Leu Val Leu Val Leu Val Leu Gly Cys Cys
1               5                   10                  15

Phe Ala Ala Pro Arg Gln Arg Gln Ser Thr Leu Val Leu Phe Pro
        20                  25                  30

Gly Asp Leu Arg Thr Asn Leu Thr Asp Arg Gln Leu Ala Glu Glu Tyr
            35                  40                  45

Leu Tyr Arg Tyr Gly Tyr Thr Arg Val Ala Glu Met Arg Gly Glu Ser
    50                  55                  60

Lys Ser Leu Gly Pro Ala Leu Leu Leu Leu Gln Lys Gln Leu Ser Leu
65                  70                  75                  80

Pro Glu Thr Gly Glu Leu Asp Ser Ala Thr Leu Lys Ala Met Arg Thr
                85                  90                  95

Pro Arg Cys Gly Val Pro Asp Leu Gly Arg Phe Gln Thr Phe Glu Gly
            100                 105                 110

Asp Leu Lys Trp His His His Asn Ile Thr Tyr Trp Ile Gln Asn Tyr
        115                 120                 125

Ser Glu Asp Leu Pro Arg Ala Val Ile Asp Asp Ala Phe Ala Arg Ala
    130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
            180                 185                 190

Pro Pro Gly Pro Gly Ile Gln Gly Asp Ala His Phe Asp Asp Asp Glu
        195                 200                 205

Leu Trp Ser Leu Gly Lys Gly Val Val Val Pro Thr Arg Phe Gly Asn
    210                 215                 220

Ala Asp Gly Ala Ala Cys His Phe Pro Phe Ile Phe Glu Gly Arg Ser
225                 230                 235                 240

Tyr Ser Ala Cys Thr Thr Asp Gly Arg Ser Asp Gly Leu Pro Trp Cys
                245                 250                 255

Ser Thr Thr Ala Asn Tyr Asp Thr Asp Asp Arg Phe Gly Phe Cys Pro
            260                 265                 270

Ser Glu Arg Leu Tyr Thr Arg Asp Gly Asn Ala Asp Gly Lys Pro Cys
        275                 280                 285

Gln Phe Pro Phe Ile Phe Gln Gly Gln Ser Tyr Ser Ala Cys Thr Thr
    290                 295                 300

Asp Gly Arg Ser Asp Gly Tyr Arg Trp Cys Ala Thr Thr Ala Asn Tyr
305                 310                 315                 320

Asp Arg Asp Lys Leu Phe Gly Phe Cys Pro Thr Arg Ala Asp Ser Thr
                325                 330                 335

Val Met Gly Gly Asn Ser Ala Gly Glu Leu Cys Val Phe Pro Phe Thr
            340                 345                 350

Phe Leu Gly Lys Glu Tyr Ser Thr Cys Thr Ser Glu Gly Arg Gly Asp
        355                 360                 365

Gly Arg Leu Trp Cys Ala Thr Thr Ser Asn Phe Asp Ser Asp Lys Lys
    370                 375                 380

Trp Gly Phe Cys Pro Asp Gln Gly Tyr Ser Leu Phe Leu Val Ala Ala
385                 390                 395                 400

-continued

```
His Glu Phe Gly His Ala Leu Gly Leu Asp His Ser Val Pro Glu
            405                 410                 415

Ala Leu Met Tyr Pro Met Tyr Arg Phe Thr Glu Gly Pro Pro Leu His
        420                 425                 430

Lys Asp Asp Val Asn Gly Ile Arg His Leu Tyr Gly Pro Arg Pro Glu
    435                 440                 445

Pro Glu Pro Arg Pro Pro Thr Thr Thr Pro Gln Pro Thr Ala Pro
450                 455                 460

Pro Thr Val Cys Pro Thr Gly Pro Pro Thr Val His Pro Ser Glu Arg
465                 470                 475                 480

Pro Thr Ala Gly Pro Thr Gly Pro Pro Ser Ala Gly Pro Thr Gly Pro
                485                 490                 495

Pro Thr Ala Gly Pro Ser Thr Ala Thr Thr Val Pro Leu Ser Pro Val
                500                 505                 510

Asp Asp Ala Cys Asn Val Asn Ile Phe Asp Ala Ile Ala Glu Ile Gly
            515                 520                 525

Asn Gln Leu Tyr Leu Phe Lys Asp Gly Lys Tyr Trp Arg Phe Ser Glu
    530                 535                 540

Gly Arg Gly Ser Arg Pro Gln Gly Pro Phe Leu Ile Ala Asp Lys Trp
545                 550                 555                 560

Pro Ala Leu Pro Arg Lys Leu Asp Ser Val Phe Glu Glu Pro Leu Ser
                565                 570                 575

Lys Lys Leu Phe Phe Ser Gly Arg Gln Val Trp Val Tyr Thr Gly
                580                 585                 590

Ala Ser Val Leu Gly Pro Arg Arg Leu Asp Lys Leu Gly Leu Gly Ala
        595                 600                 605

Asp Val Ala Gln Val Thr Gly Ala Leu Arg Ser Gly Arg Gly Lys Met
    610                 615                 620

Leu Leu Phe Ser Gly Arg Arg Leu Trp Arg Phe Asp Val Lys Ala Gln
625                 630                 635                 640

Met Val Asp Pro Arg Ser Ala Ser Glu Val Asp Arg Met Phe Pro Gly
                645                 650                 655

Val Pro Leu Asp Thr His Asp Val Phe Gln Tyr Arg Glu Lys Ala Tyr
                660                 665                 670

Phe Cys Gln Asp Arg Phe Tyr Trp Arg Val Ser Ser Arg Ser Glu Leu
        675                 680                 685

Asn Gln Val Asp Gln Val Gly Tyr Val Thr Tyr Asp Ile Leu Gln Cys
    690                 695                 700

Pro Glu Asp
705

<210> SEQ ID NO 39
<211> LENGTH: 2387
<212> TYPE: DNA
<213> ORGANISM: Homo sapiens

<400> SEQUENCE: 39
agacacctct gccctcacca tgagcctctg cagcccctg gtcctggtgc tcctggtgct      60
gggctgctgc tttgctgccc ccagacagcg ccagtccacc cttgtgctct cccctggaga     120
cctgagaacc aatctcaccg acaggcagct ggcagaggaa tacctgtacc gctatggtta     180
cactcgggtg gcagagatgc gtggagagtc gaaatctctg gggcctgcgc tgctgcttct     240
ccagaagcaa ctgtccctgc ccgagaccgg tgagctggat agcgccacgc tgaaggccat     300 gcgaaccca cggtgcgggg tcccagacct gggcagattc caaacctttg agggcgacct     360
```

```
caagtggcac caccacaaca tcacctattg gatccaaaac tactcggaag acttgccgcg    420
ggcggtgatt gacgacgcct tgcccgcgc cttcgcactg tggagcgcgg tgacgccgct    480
caccttcact cgcgtgtaca gccgggacgc agacatcgtc atccagtttg gtgtcgcgga    540
gcacggagac gggtatccct tcgacgggaa ggacgggctc ctggcacacg cctttcctcc    600
tggccccggc attcagggag acgcccattt cgacgatgac gagttgtggt ccctgggcaa    660
gggcgtcgtg gttccaactc ggtttggaaa cgcagatggc gcggcctgcc acttccccct    720
catcttcgag ggccgctcct actctgcctg caccaccgac ggtcgctccg acggcttgcc    780
ctggtgcagt accacggcca actacgcacc cgacgaccgg tttggcttct gccccagcga    840
gagactctac acccaggacg gcaatgctga tgggaaaccc tgccagtttc cattcatctt    900
ccaaggccaa tcctactccg cctgcaccac ggacggtcgc tccgacggct accgctggtg    960
cgccaccacc gccaactacg accgggacaa gctcttcggc ttctgcccga cccgagctga   1020
ctcgacggtg atgggggggca actcggcggg ggagctgtgc gtcttcccct tcactttcct   1080
gggtaaggag tactcgacct gtaccagcga gggccgcgga gatgggcgcc tctggtgcgc   1140
taccacctcg aactttgaca gcgacaagaa gtggggcttc tgcccggacc aaggatacag   1200
tttgttcctc gtggcggcgc atgagttcgg ccacgcgctg gcttagatc attcctcagt   1260 gccgaggcg ctcatgtacc ctatgtaccg cttcactgag gggcccccct tgcataagga   1320
cgacgtgaat ggcatccggc acctctatgg tcctcgccct gaacctgagc cacggcctcc   1380
aaccaccacc acaccgcagc ccacggctcc cccgacggtc tgccccaccg accccccac    1440 tgtccacccc tcagagcgcc ccacagctgg ccccacaggt ccccctcag ctggccccac    1500 aggtcccccc actgctggcc cttctacggc cactactgtg cctttgagtc cggtggacga   1560
tgcctgcaac gtgaacatct tcgacgccat cgcggagatt gggaaccagc tgtatttgtt   1620
caaggatggg aagtactggc gattctctga gggcaggggg agccggccgc agggcccctt   1680
ccttatcgcc gacaagtggc ccgcgctgcc ccgcaagctg gactcggtct ttgaggagcg   1740
gctctccaag aagctttct tcttctctgg gcgccaggtg tgggtgtaca caggcgcgtc   1800
ggtgctgggc ccgaggcgtc tggacaagct gggcctggga gccgacgtgg cccaggtgac   1860
cggggccctc cggagtggca gggggaagat gctgctgttc agcgggcggc gcctctggag   1920
gttcgacgtg aaggcgcaga tggtggatcc ccggagcgcc agcgaggtgg accggatgtt   1980
ccccggggtg cctttggaca cgcacgacgt cttccagtac cgagagaaag cctatttctg   2040
ccaggaccgc ttctactggc gcgtgagttc ccggagtgag ttgaaccagg tggaccaagt   2100
gggctacgtg acctatgaca tcctgcagtg ccctgaggac tagggctccc gtcctgcttt   2160
ggcagtgcca tgtaaatccc cactgggacc aaccctgggg aaggagccag tttgccggat   2220
acaaactggt attctgttct ggaggaaagg gaggagtgga ggtgggctgg ccctctctt   2280 ctcacctttg ttttttgttg gagtgtttct aataaacttg gattctctaa cctttaaaaa   2340
aaaaaaaaaa aaaaaaaaaa aaaaaaaaaa aaaaaaaaaa aaaaaa               2387
```

<210> SEQ ID NO 40
<211> LENGTH: 9
<212> TYPE: PRT
<213> ORGANISM: Artificial Sequence
<220> FEATURE:
<223> OTHER INFORMATION: MMP9 peptide

<400> SEQUENCE: 40

Ala Val Ile Asp Asp Ala Phe Ala Arg
1               5

<210> SEQ ID NO 41
<211> LENGTH: 9
<212> TYPE: PRT
<213> ORGANISM: Artificial Sequence
<220> FEATURE:
<223> OTHER INFORMATION: MMP9 peptide

<400> SEQUENCE: 41

Phe Gln Thr Phe Glu Gly Asp Leu Lys
1               5

<210> SEQ ID NO 42
<211> LENGTH: 15
<212> TYPE: PRT
<213> ORGANISM: Artificial Sequence
<220> FEATURE:
<223> OTHER INFORMATION: MMP9 peptide

<400> SEQUENCE: 42

Leu Gly Leu Gly Ala Asp Val Ala Gln Val Thr Gly Ala Leu Arg
1               5                   10                  15

<210> SEQ ID NO 43
<211> LENGTH: 11
<212> TYPE: PRT
<213> ORGANISM: Artificial Sequence
<220> FEATURE:
<223> OTHER INFORMATION: MMP9 peptide

<400> SEQUENCE: 43

Ser Leu Gly Pro Ala Leu Leu Leu Leu Gln Lys
1               5                   10

<210> SEQ ID NO 44
<211> LENGTH: 15
<212> TYPE: PRT
<213> ORGANISM: Artificial Sequence
<220> FEATURE:
<223> OTHER INFORMATION: MMP9 peptide

<400> SEQUENCE: 44

Ala Phe Ala Leu Trp Ser Ala Val Thr Pro Leu Thr Phe Thr Arg
1               5                   10                  15

<210> SEQ ID NO 45
<211> LENGTH: 111
<212> TYPE: PRT
<213> ORGANISM: Homo sapiens

<400> SEQUENCE: 45

Met Ser Leu Leu Pro Arg Arg Ala Pro Pro Val Ser Met Arg Leu Leu
1               5                   10                  15

Ala Ala Ala Leu Leu Leu Leu Leu Ala Leu Tyr Thr Ala Arg Val
            20                  25                  30

Asp Gly Ser Lys Cys Lys Cys Ser Arg Lys Gly Pro Lys Ile Arg Tyr
        35                  40                  45

Ser Asp Val Lys Lys Leu Glu Met Lys Pro Lys Tyr Pro His Cys Glu
        50                  55                  60

Glu Lys Met Val Ile Ile Thr Thr Lys Ser Val Ser Arg Tyr Arg Gly
65                  70                  75                  80

Gln Glu His Cys Leu His Pro Lys Leu Gln Ser Thr Lys Arg Phe Ile 85                  90                  95
Lys Trp Tyr Asn Ala Trp Asn Glu Lys Arg Arg Val Tyr Glu Glu
                100                 105                 110

<210> SEQ ID NO 46
<211> LENGTH: 1989
<212> TYPE: DNA
<213> ORGANISM: Homo sapiens

<400> SEQUENCE: 46

```
aatgtgtgcg cgctgtggta tgggtgtgca agtgtgcgaa ggcggcgtgt tgtgtgagcg      60
agagggtagc ggatgtgtgt gtgcgtgtgc gcgcgtggct ccgggtgtgc gccgctgcga     120
tagcgggtcc tttcccgggg cgggcgacgg gcgggctggg aaggtctcct cccctcacca     180
cattgagaaa tctcagtgag tcaccgagtg gttctgcata ttaatgagct cgctcgctgc     240
gagggcagga gcggatttaa agaggccagg gcgggcgga gggaggctgt ggagagagcg      300
cggagacaag cgcagagcgc agcgcacggc cacagacagc cctgggcatc caccgacggc     360
gcagccggag ccagcagagc cggaaggcgc gccccgggca gagaaagccg agcagagctg     420
ggtggcgtct ccgggccgcc gctccgacgg gccagcgccc tccccatgtc cctgctccca     480
cgccgcgccc ctccggtcag catgaggctc ctggcggccg cgctgctcct gctgctgctg     540
gcgctgtaca ccgcgcgtgt ggacgggtcc aaatgcaagt gctcccggaa gggacccaag     600
atccgctaca gcgacgtgaa gaagctggaa atgaagccaa gtacccgca ctgcgaggag      660
aagatggtta tcatcaccac caagagcgtg tccaggtacc gaggtcagga gcactgcctg     720
caccccaagc tgcagagcac caagcgcttc atcaagtggt acaacgcctg gaacgagaag     780
cgcagggtct acgaagaata gggtgaaaaa cctcagaagg aaaactcca aaccagttgg      840
gagacttgtg caaaggactt tgcagattaa aaaaaaaaaa aaaaaaaaa aaaaaaaaaa      900
aaaaaaaaaa agcctttctt tctcacaggc ataagacaca aattatatat tgttatgaag     960
cactttttac caacggtcag tttttacatt ttatagctgc gtgcgaaagg cttccagatg    1020
ggagacccat ctctcttgtg ctccagactt catcacaggc tgcttttat caaaaagggg     1080
aaaactcatg cctttccttt ttaaaaaatg cttttttgta tttgtccata cgtcactata    1140
catctgagct ttataagcgc ccgggaggaa caatgagctt ggtggacaca tttcattgca    1200
gtgttgctcc attcctagct tgggaagctt ccgcttagag gtcctggcgc tcggcacag     1260
ctgccacggg ctctcctggg cttatggccg gtcacagcct cagtgtgact ccacagtggc    1320
ccctgtagcc gggcaagcag gagcaggtct ctctgcatct gttctctgag gaactcaagt    1380
ttggttgcca gaaaaatgtg cttcattccc cctggttaa ttttacaca ccctaggaaa     1440
catttccaag atcctgtgat ggcgagacaa atgatcctta agaaggtgt ggggtctttc     1500
ccaacctgag gatttctgaa aggttcacag gttcaatatt taatgcttca gaagcatgtg    1560
aggttcccaa cactgtcagc aaaaacctta ggagaaaact taaaaatata tgaatacatg    1620
cgcaatacac agctacagac acacattctg ttgacaaggg aaaaccttca aagcatgttt    1680
ctttccctca ccacaacaga acatgcagta ctaaagcaat atatttgtga ttccccatgt    1740
aattcttcaa tgttaaacag tgcagtcctc tttcgaaagc taagatgacc atgcgccctt    1800
tcctctgtac atatacccctt aagaacgccc cctccacaca ctgcccccca gtatatgccg    1860
cattgtactg ctgtgttata tgctatgtac atgtcagaaa ccattagcat tgcatgcagg    1920
tttcatattc tttctaagat ggaaagtaat aaaatatatt tgaaatgtac caaaaaaaaa    1980
``` aaaaaaaaa                                                          1989

<210> SEQ ID NO 47
<211> LENGTH: 7
<212> TYPE: PRT
<213> ORGANISM: Artificial Sequence
<220> FEATURE:
<223> OTHER INFORMATION: CXCL14 peptide

<400> SEQUENCE: 47

Met Val Ile Ile Thr Thr Lys
1               5

<210> SEQ ID NO 48
<211> LENGTH: 8
<212> TYPE: PRT
<213> ORGANISM: Artificial Sequence
<220> FEATURE:
<223> OTHER INFORMATION: CXCL14 peptide

<400> SEQUENCE: 48

Trp Tyr Asn Ala Trp Asn Glu Lys
1               5

<210> SEQ ID NO 49
<211> LENGTH: 9
<212> TYPE: PRT
<213> ORGANISM: Artificial Sequence
<220> FEATURE:
<223> OTHER INFORMATION: CXCL14 peptide

<400> SEQUENCE: 49

Gly Gln Glu His Cys Leu His Pro Lys
1               5

<210> SEQ ID NO 50
<211> LENGTH: 7
<212> TYPE: PRT
<213> ORGANISM: Artificial Sequence
<220> FEATURE:
<223> OTHER INFORMATION: CXCL14 peptide

<400> SEQUENCE: 50

Tyr Pro His Cys Glu Glu Lys
1               5

<210> SEQ ID NO 51
<211> LENGTH: 161
<212> TYPE: PRT
<213> ORGANISM: Homo sapiens

<400> SEQUENCE: 51

Met Asn Leu Ala Ile Ser Ile Ala Leu Leu Leu Thr Val Leu Gln Val
1               5                   10                  15

Ser Arg Gly Gln Lys Val Thr Ser Leu Thr Ala Cys Leu Val Asp Gln
            20                  25                  30

Ser Leu Arg Leu Asp Cys Arg His Glu Asn Thr Ser Ser Ser Pro Ile
        35                  40                  45

Gln Tyr Glu Phe Ser Leu Thr Arg Glu Thr Lys Lys His Val Leu Phe
    50                  55                  60

Gly Thr Val Gly Val Pro Glu His Thr Tyr Arg Ser Arg Thr Asn Phe
65                  70                  75                  80

Thr Ser Lys Tyr Asn Met Lys Val Leu Tyr Leu Ser Ala Phe Thr Ser
                85                  90                  95

Lys Asp Glu Gly Thr Tyr Thr Cys Ala Leu His His Ser Gly His Ser
            100                 105                 110

Pro Pro Ile Ser Ser Gln Asn Val Thr Val Leu Arg Asp Lys Leu Val
            115                 120                 125

Lys Cys Glu Gly Ile Ser Leu Leu Ala Gln Asn Thr Ser Trp Leu Leu
130                 135                 140

Leu Leu Leu Leu Ser Leu Ser Leu Leu Gln Ala Thr Asp Phe Met Ser
145                 150                 155                 160

Leu

<210> SEQ ID NO 52
<211> LENGTH: 1145
<212> TYPE: DNA
<213> ORGANISM: Homo sapiens

<400> SEQUENCE: 52
ggaggctgca gcagcggaag accccagtcc agatccagga ctgagatccc agaaccatga     60
acctggccat cagcatcgct ctcctgctaa cagtcttgca ggtctcccga gggcagaagg    120
tgaccagcct aacggcctgc ctagtggacc agagccttcg tctggactgc cgccatgaga    180
ataccagcag ttcacccatc cagtacgagt tcagcctgac ccgtgagaca agaagcacg    240 tgctctttgg cactgtgggg gtgcctgagc acacataccg ctcccgaacc aacttcacca    300
gcaaatacaa catgaaggtc ctctacttat ccgccttcac tagcaaggac gagggcacct    360
acacgtgtgc actccaccac tctggccatt cccacccat ctcctcccag aacgtcacag    420
tgctcagaga caaactggtc aagtgtgagg gcatcagcct gctggctcag aacacctcgt    480
ggctgctgct gctcctgctc tccctctccc tcctccaggc cacggatttc atgtccctgt    540
gactggtggg gcccatggag gagacaggaa gcctcaagtt ccagtgcaga gatcctactt    600
ctctgagtca gctgaccccc tccccccaat ccctcaaacc ttgaggagaa gtggggaccc    660 caccctcat caggagttcc agtgctgcat gcgattatct acccacgtcc acgcggccac    720
ctcaccctct ccgcacacct ctggctgtct ttttgtactt tttgttccag agctgcttct    780
gtctggttta tttaggtttt atccttcctt ttctttgaga gttcgtgaag agggaagcca    840
ggattgggga cctgatggag agtgagagca tgtgaggggt agtgggatgg tggggtacca    900
gccactggag gggtcatcct tgcccatcgg gaccagaaac ctgggagaga cttggatgag    960
gagtggttgg gctgtgcctg ggcctagcac ggacatggtc tgtcctgaca gcactcctcg   1020
gcaggcatgg ctggtgcctg aagaccccag atgtgagggc accaccaaga atttgtggcc   1080
taccttgtga gggagagaac tgagcatctc cagcattctc agccacaacc aaaaaaaaaa   1140
aaaaa                                                               1145

<210> SEQ ID NO 53
<211> LENGTH: 10
<212> TYPE: PRT
<213> ORGANISM: Artificial Sequence
<220> FEATURE:
<223> OTHER INFORMATION: CD90 peptide

<400> SEQUENCE: 53

Val Leu Tyr Leu Ser Ala Phe Thr Ser Lys
1               5                   10

<210> SEQ ID NO 54
<211> LENGTH: 14

```
<212> TYPE: PRT
<213> ORGANISM: Artificial Sequence
<220> FEATURE:
<223> OTHER INFORMATION: CD90 peptide

<400> SEQUENCE: 54

Val Thr Ser Leu Thr Ala Cys Leu Val Asp Gln Ser Leu Arg
1               5                   10

<210> SEQ ID NO 55
<211> LENGTH: 15
<212> TYPE: PRT
<213> ORGANISM: Artificial Sequence
<220> FEATURE:
<223> OTHER INFORMATION: CD90 peptide

<400> SEQUENCE: 55

His Val Leu Phe Gly Thr Val Gly Val Pro Glu His Thr Tyr Arg
1               5                   10                  15

<210> SEQ ID NO 56
<211> LENGTH: 779
<212> TYPE: PRT
<213> ORGANISM: Homo sapiens

<400> SEQUENCE: 56

Met Ile Pro Phe Leu Pro Met Phe Ser Leu Leu Leu Leu Leu Ile Val
1               5                   10                  15

Asn Pro Ile Asn Ala Asn Asn His Tyr Asp Lys Ile Leu Ala His Ser
                20                  25                  30

Arg Ile Arg Gly Arg Asp Gln Gly Pro Asn Val Cys Ala Leu Gln Gln
            35                  40                  45

Ile Leu Gly Thr Lys Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255
```

```
Ser Asp Ile Leu Glu Ala Leu Gly Arg Asp Gly His Phe Thr Leu Phe
        260                 265                 270

Ala Pro Thr Asn Glu Ala Phe Glu Lys Leu Pro Arg Gly Val Leu Glu
            275                 280                 285

Arg Ile Met Gly Asp Lys Val Ala Ser Glu Ala Leu Met Lys Tyr His
        290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Asp Ile Val
        340                 345                 350

Thr Asn Asn Gly Val Ile His Leu Ile Asp Gln Val Leu Ile Pro Asp
            355                 360                 365

Ser Ala Lys Gln Val Ile Glu Leu Ala Gly Lys Gln Gln Thr Thr Phe
        370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
            420                 425                 430

Ile Leu Lys Val Lys Val Gly Leu Asn Glu Leu Tyr Asn Gly Gln Ile
        435                 440                 445

Leu Glu Thr Ile Gly Gly Lys Gln Leu Arg Val Phe Val Tyr Arg Thr
        450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
        515                 520                 525

Gly Asp Trp Thr Leu Phe Val Pro Thr Asn Asp Ala Phe Lys Gly Met
        530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
        595                 600                 605

Ser Lys Glu Ser Asp Ile Met Thr Thr Asn Gly Val Ile His Val Val
        610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Lys Pro Ile
            660                 665                 670

Ile Lys Lys Tyr Thr Lys Ile Ile Asp Gly Val Pro Val Glu Ile Thr
```

```
                675                 680                 685
Glu Lys Glu Thr Arg Glu Arg Ile Ile Thr Gly Pro Glu Ile Lys
            690                 695                 700
Tyr Thr Arg Ile Ser Thr Gly Gly Glu Thr Glu Thr Leu Lys
705                 710                 715                 720
Lys Leu Leu Gln Glu Glu Val Thr Lys Val Thr Lys Phe Ile Glu Gly
                725                 730                 735
Gly Asp Gly His Leu Phe Glu Asp Glu Ile Lys Arg Leu Leu Gln
            740                 745                 750
Gly Asp Thr Pro Val Arg Lys Leu Gln Ala Asn Lys Lys Val Gln Gly
            755                 760                 765
Ser Arg Arg Arg Leu Arg Glu Gly Arg Ser Gln
770                 775
```

<210> SEQ ID NO 57
<211> LENGTH: 2455
<212> TYPE: DNA
<213> ORGANISM: Homo sapiens

<400> SEQUENCE: 57

| | | | | | |
|---|---|---|---|---|---|
| agagactcaa | gatgattccc | tttttaccca | tgttttctct | actattgctg | cttattgtta | 60 |
| accctataaa | cgccaacaat | cattatgaca | agatcttggc | tcatagtcgt | atcaggggtc | 120 |
| gggaccaagg | cccaaatgtc | tgtgcccttc | aacagatttt | gggcaccaaa | aagaaatact | 180 |
| tcagcacttg | taagaactgg | tataaaaagt | ccatctgtgg | acagaaaacg | actgtgttat | 240 |
| atgaatgttg | ccctggttat | atgagaatgg | aaggaatgaa | aggctgccca | gcagttttgc | 300 |
| ccattgacca | tgtttatggc | actctgggca | tcgtgggagc | caccacaacg | cagcgctatt | 360 |
| ctgacgcctc | aaaactgagg | gaggagatcg | agggaaaggg | atccttcact | tactttgcac | 420 |
| cgagtaatga | ggcttgggac | aacttggatt | ctgatatccg | tagaggtttg | gagagcaacg | 480 |
| tgaatgttga | attactgaat | gctttacata | gtcacatgat | taataagaga | atgttgacca | 540 |
| aggacttaaa | aaatggcatg | attattcctt | caatgtataa | caatttgggg | cttttcatta | 600 |
| accattatcc | taatggggtt | gtcactgtta | attgtgctcg | aatcatccat | gggaaccaga | 660 |
| ttgcaacaaa | tggtgttgtc | catgtcattg | accgtgtgct | tacacaaatt | ggtacctcaa | 720 |
| ttcaagactt | cattgaagca | gaagatgacc | tttcatcttt | tagagcagct | gccatcacat | 780 |
| cggacatatt | ggaggccctt | ggaagagacg | gtcacttcac | actcttgct | cccaccaatg | 840 |
| aggcttttga | gaacttcca | cgaggtgtcc | tagaaaggat | catgggagac | aaagtggctt | 900 |
| ccgaagctct | tatgaagtac | cacatcttaa | atactctcca | gtgttctgag | tctattatgg | 960 |
| gaggagcagt | ctttgagacg | ctggaaggaa | atacaattga | gataggatgt | gacggtgaca | 1020 |
| gtataacagt | aaatggaatc | aaaatggtga | acaaaaagga | tattgtgaca | aataatggtg | 1080 |
| tgatccattt | gattgatcag | gtcctaattc | ctgattctgc | caaacaagtt | attgagctgg | 1140 |
| ctggaaaaca | gcaaaccacc | ttcacggatc | ttgtggccca | attaggcttg | gcatctgctc | 1200 |
| tgaggccaga | tggagaatac | actttgctgg | cacctgtgaa | taatgcattt | tctgatgata | 1260 |
| ctctcagcat | ggatcagcgc | ctccttaaat | taattctgca | gaatcacata | ttgaaagtaa | 1320 |
| aagttggcct | taatgagctt | tacaacgggc | aaatactgga | aaccatcgga | ggcaaacagc | 1380 |
| tcagagtctt | cgtatatcgt | acagctgtct | gcattgaaaa | ttcatgcatg | gagaagggga | 1440 |
| gtaagcaagg | gagaaacggt | gcgattcaca | tattccgcga | gatcatcaag | ccagcagaga | 1500 |
| aatcccctcca | tgaaaagtta | aaacaagata | agcgctttag | caccttcctc | agcctacttg | 1560 |

-continued

```
aagctgcaga cttgaaagag ctcctgacac aacctggaga ctggacatta tttgtgccaa   1620
ccaatgatgc ttttaaggga atgactagtg aagaaaaaga aattctgata cgggacaaaa   1680
atgctcttca aaacatcatt ctttatcacc tgacaccagg agttttcatt ggaaaaggat   1740
ttgaacctgg tgttactaac attttaaaga ccacacaagg aagcaaaatc tttctgaaag   1800
aagtaaatga tacacttctg gtgaatgaat tgaaatcaaa agaatctgac atcatgacaa   1860
caaatggtgt aattcatgtt gtagataaac tcctctatcc agcagacaca cctgttggaa   1920
atgatcaact gctggaaata cttaataaat taatcaaata catccaaatt aagtttgttc   1980
gtggtagcac cttcaaagaa atccccgtga ctgtctataa gccaattatt aaaaaataca   2040
ccaaaatcat tgatggagtg cctgtggaaa taactgaaaa agagacacga gaagaacgaa   2100
tcattacagg tcctgaaata aaatacacta ggatttctac tggaggtgga gaaacagaag   2160
aaactctgaa gaaattgtta caagaagagg tcaccaaggt caccaaattc attgaaggtg   2220
gtgatggtca tttatttgaa gatgaagaaa ttaaaagact gcttcaggga gacacacccg   2280
tgaggaagtt gcaagccaac aaaaaagttc aaggatctag aagacgatta agggaaggtc   2340
gttctcagtg aaaatccaaa aaccagaaaa aaatgtttat acaaccctaa gtcaataacc   2400
tgaccttaga aaattgtgag agccaagttg acttcaggaa ctgaaacatc agcac        2455
```

<210> SEQ ID NO 58
<211> LENGTH: 14
<212> TYPE: PRT
<213> ORGANISM: Artificial Sequence
<220> FEATURE:
<223> OTHER INFORMATION: POSTN peptide

<400> SEQUENCE: 58

Ala Ala Ala Ile Thr Ser Asp Ile Leu Glu Ala Leu Gly Arg
1               5                   10

<210> SEQ ID NO 59
<211> LENGTH: 18
<212> TYPE: PRT
<213> ORGANISM: Artificial Sequence
<220> FEATURE:
<223> OTHER INFORMATION: POSTN peptide

<400> SEQUENCE: 59

Val Gly Leu Asn Glu Leu Tyr Asn Gly Gln Ile Leu Glu Thr Ile Gly
1               5                   10                  15

Gly Lys

<210> SEQ ID NO 60
<211> LENGTH: 8
<212> TYPE: PRT
<213> ORGANISM: Artificial Sequence
<220> FEATURE:
<223> OTHER INFORMATION: POSTN peptide

<400> SEQUENCE: 60

Asn Gly Ala Ile His Ile Phe Arg
1               5

<210> SEQ ID NO 61
<211> LENGTH: 9
<212> TYPE: PRT
<213> ORGANISM: Artificial Sequence
<220> FEATURE:
<223> OTHER INFORMATION: POSTN peptide

<400> SEQUENCE: 61

Leu Ile Leu Gln Asn His Ile Leu Lys
1               5

<210> SEQ ID NO 62
<211> LENGTH: 346
<212> TYPE: PRT
<213> ORGANISM: Homo sapiens

<400> SEQUENCE: 62

Met Phe Leu Ser Ile Leu Val Ala Leu Cys Leu Trp Leu His Leu Ala
1               5                   10                  15

Leu Gly Met Arg Gly Ala Pro Cys Glu Ala Val Arg Ile Pro Met Cys
            20                  25                  30

Arg His Met Pro Trp Asn Ile Thr Arg Met Pro Asn His Leu His His
        35                  40                  45

Ser Thr Gln Glu Asn Ala Ile Leu Ala Ile Glu Gln Tyr Glu Glu Leu
    50                  55                  60

Val Asp Val Asn Cys Ser Ala Val Leu Arg Phe Phe Leu Cys Ala Met
65                  70                  75                  80

Tyr Ala Pro Ile Cys Thr Leu Glu Phe Leu His Asp Pro Ile Lys Pro
                85                  90                  95

Cys Lys Ser Val Cys Gln Arg Ala Arg Asp Asp Cys Glu Pro Leu Met
            100                 105                 110

Lys Met Tyr Asn His Ser Trp Pro Glu Ser Leu Ala Cys Asp Glu Leu
        115                 120                 125

Pro Val Tyr Asp Arg Gly Val Cys Ile Ser Pro Glu Ala Ile Val Thr
    130                 135                 140

Asp Leu Pro Glu Asp Val Lys Trp Ile Asp Ile Thr Pro Asp Met Met
145                 150                 155                 160

Val Gln Glu Arg Pro Leu Asp Val Asp Cys Lys Arg Leu Ser Pro Asp
                165                 170                 175

Arg Cys Lys Cys Lys Lys Val Lys Pro Thr Leu Ala Thr Tyr Leu Ser
            180                 185                 190

Lys Asn Tyr Ser Tyr Val Ile His Ala Lys Ile Lys Ala Val Gln Arg
        195                 200                 205

Ser Gly Cys Asn Glu Val Thr Thr Val Val Asp Val Lys Glu Ile Phe
    210                 215                 220

Lys Ser Ser Ser Pro Ile Pro Arg Thr Gln Val Pro Leu Ile Thr Asn
225                 230                 235                 240

Ser Ser Cys Gln Cys Pro His Ile Leu Pro His Gln Asp Val Leu Ile
                245                 250                 255

Met Cys Tyr Glu Trp Arg Ser Arg Met Met Leu Leu Glu Asn Cys Leu
            260                 265                 270

Val Glu Lys Trp Arg Asp Gln Leu Ser Lys Arg Ser Ile Gln Trp Glu
        275                 280                 285

Glu Arg Leu Gln Glu Gln Arg Arg Thr Val Gln Asp Lys Lys Lys Thr
    290                 295                 300

Ala Gly Arg Thr Ser Arg Ser Asn Pro Pro Lys Pro Lys Gly Lys Pro
305                 310                 315                 320

Pro Ala Pro Lys Pro Ala Ser Pro Lys Lys Asn Ile Lys Thr Arg Ser
                325                 330                 335

Ala Gln Lys Arg Thr Asn Pro Lys Arg Val
        340                 345

<210> SEQ ID NO 63
<211> LENGTH: 2974
<212> TYPE: DNA
<213> ORGANISM: Homo sapiens

<400> SEQUENCE: 63

| | | | | | | |
|---|---|---|---|---|---|---|
| gcggccgagg | gggagcccgc | gccgcggctg | cagctgccaa | gggagcgttc | cgagcccacg | 60 |
| tcagggagg | tgtcgggata | aatagggtcc | cgcaatggcc | gtggctggct | gcgctccgag | 120 |
| ctgcggagtc | cgggactgga | gctgcccggg | cgggttcgcg | ccccgaaggc | tgagagctgg | 180 |
| cgctgctcgt | gccctgtgtg | ccagacggcg | gagctccgcg | gccggacccc | gcggcccgc | 240 |
| tttgctgccg | actggagttt | gggggaagaa | actctcctgc | gccccagagg | atttcttcct | 300 |
| cggcgaaggg | acagcgaaag | atgagggtgg | caggaagaga | agggcgcttt | ctgtctgccg | 360 |
| gggtcgcagc | gcgagagggc | agtgccatgt | tcctctccat | cctagtggcg | ctgtgcctgt | 420 |
| ggctgcacct | ggcgctgggc | gtgcgcggcg | cgccctgcga | ggcggtgcgc | atccctatgt | 480 |
| gccggcacat | gccctggaac | atcacgcgga | tgcccaacca | cctgcaccac | agcacgcagg | 540 |
| agaacgccat | cctggccatc | gagcagtacg | aggagctggt | ggacgtgaac | tgcagcgccg | 600 |
| tgctgcgctt | cttcctctgt | gccatgtacg | cgcccatttg | caccctggag | ttcctgcacg | 660 |
| accctatcaa | gccgtgcaag | tcggtgtgcc | aacgcgcgcg | cgacgactgc | gagcccctca | 720 |
| tgaagatgta | caaccacagc | tggcccgaaa | gcctggcctg | cgacgagctg | cctgtctatg | 780 |
| accgtggcgt | gtgcatctcg | cctgaagcca | tcgtcacgga | cctcccggag | gatgttaagt | 840 |
| ggatagacat | cacaccagac | atgatggtac | aggaaaggcc | tcttgatgtt | gactgtaaac | 900 |
| gcctaagccc | cgatcggtgc | aagtgtaaaa | aggtgaagcc | aactttggca | acgtatctca | 960 |
| gcaaaaacta | cagctatgtt | attcatgcca | aaataaaagc | tgtgcagagg | agtggctgca | 1020 |
| atgaggtcac | aacggtggtg | gatgtaaaag | agatcttcaa | gtcctcatca | cccatccctc | 1080 |
| gaactcaagt | cccgctcatt | acaaattctt | cttgccagtg | tccacacatc | ctgccccatc | 1140 |
| aagatgttct | catcatgtgt | tacgagtggc | gctcaaggat | gatgcttctt | gaaaattgct | 1200 |
| tagttgaaaa | atggagagat | cagcttagta | aaagatccat | acagtgggaa | gagaggctgc | 1260 |
| aggaacagcg | gagaacagtt | caggacaaga | agaaaacagc | cgggcgcacc | agtcgtagta | 1320 |
| atcccccaa | accaaaggga | aagcctcctg | ctcccaaacc | agccagtccc | aagaagaaca | 1380 |
| ttaaaactag | gagtgcccag | aagagaacaa | acccgaaaag | agtgtgagct | aactagtttc | 1440 |
| caaagcggag | acttccgact | tccttacagg | atgaggctgg | gcattgcctg | ggacagccta | 1500 |
| tgtaaggcca | tgtgccccct | gccctaacaa | ctcactgcag | tgctcttcat | agacacatct | 1560 |
| tgcagcattt | tcttaaggc | tatgcttcag | ttttctttg | taagccatca | caagccatag | 1620 |
| tggtaggttt | gcccttggt | acagaaggtg | agttaaagct | ggtggaaaag | gcttattgca | 1680 |
| ttgcattcag | agtaacctgt | gtgcatactc | tagaagagta | gggaaaataa | tgcttgttac | 1740 |
| aattcgacct | aatatgtgca | ttgtaaaata | aatgccatat | ttcaaacaaa | acacgtaatt | 1800 |
| tttttacagt | atgttttatt | accttttgat | atctgttgtt | gcaatgttag | tgatgtttta | 1860 |
| aaatgtgatc | gaaatataa | tgcttctaag | aaggaacagt | agtggaatga | atgtctaaaa | 1920 |
| gatctttatg | tgtttatggt | ctgcagaagg | attttttgtga | tgaaggggga | ttttttgaaa | 1980 |
| aatctagaga | agtagcatat | ggaaaactat | aatgtgtctt | ttttacaatg | acttcagctc | 2040 |
| tgtttttagc | tagaaactct | aaaaacaaaa | ataataataa | agaaaaataa | ataaaaagga | 2100 |

```
gaggcagaca atgtctggat tcctgttttt tggttacctg atttcatgat catgatgctt    2160
cttgtcaaca ccctcttaag cagcaccaga aacagtgagt ttgtctgtac cattaggagt    2220
taggtactaa ttagttggct aatgctcaag tattttatac ccacaagaga ggtatgtcac    2280
tcatcttact tcccaggaca tccaccctga gaataatttg acaagcttaa aaatggcctt    2340
catgtgagtg ccaaattttg ttttcttcat ttaaatattt tctttgccta aatacatgtg    2400
agaggagtta aatataaatg tacagagagg aaagttgagg ttccacctct gaaatgagaa    2460
ttacttgaca gttgggatac tttaatcaga aaaaagaac ttatcttgca gcattttatc     2520
aacaaatttc ataattgtgg acaattggag gcatttattt taaaaaacaa ttttattggc    2580
cttttgctaa cacagtaagc atgtattctc tataaggcat tcaataaatg cacaacgccc    2640
aaaggaaata aaatcctatc taatcctact ctccactaca cagaggtaat cactattagt    2700
attttggcat attattctcc aggtgtttct tatgcactta taaaatgatt tgaacaaata    2760
aaactaggaa cctgctatac atgtgtttca taacctgcct cctttgcttg gccctttatt    2820
gagataagtt ttcctgtcaa gaaagcagaa accatctcat ttctaacagc tgtgttatat    2880
tccatagtat gcattactca acaaactgtt gtgctattgg atacttaggt ggtttcttca    2940 ctgacaaatac tgaataaaca tctcaatagt caaa                               2974
```

<210> SEQ ID NO 64
<211> LENGTH: 18
<212> TYPE: PRT
<213> ORGANISM: Artificial Sequence
<220> FEATURE:
<223> OTHER INFORMATION: SFRP4 peptide

<400> SEQUENCE: 64

Gly Val Cys Ile Ser Pro Glu Ala Ile Val Thr Asp Leu Pro Glu Asp
1               5                   10                  15

Val Lys

<210> SEQ ID NO 65
<211> LENGTH: 13
<212> TYPE: PRT
<213> ORGANISM: Artificial Sequence
<220> FEATURE:
<223> OTHER INFORMATION: SFRP4 peptide

<400> SEQUENCE: 65

Ser Gly Cys Asn Glu Val Thr Thr Val Val Asp Val Lys
1               5                   10

<210> SEQ ID NO 66
<211> LENGTH: 11
<212> TYPE: PRT
<213> ORGANISM: Artificial Sequence
<220> FEATURE:
<223> OTHER INFORMATION: SFRP4 peptide

<400> SEQUENCE: 66

Val Lys Pro Thr Leu Ala Thr Tyr Leu Ser Lys
1               5                   10

<210> SEQ ID NO 67
<211> LENGTH: 9
<212> TYPE: PRT
<213> ORGANISM: Artificial Sequence
<220> FEATURE:
<223> OTHER INFORMATION: SFRP4 peptide

<400> SEQUENCE: 67

Asn Tyr Ser Tyr Val Ile His Ala Lys
1               5

<210> SEQ ID NO 68
<211> LENGTH: 227
<212> TYPE: PRT
<213> ORGANISM: Homo sapiens

<400> SEQUENCE: 68

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
        195                 200                 205

Cys Ser Val Ser His Pro Tyr Ser Gln Asp Leu Glu Gly Lys Gly Glu
    210                 215                 220

Trp Gly Pro
225

<210> SEQ ID NO 69
<211> LENGTH: 1464
<212> TYPE: DNA
<213> ORGANISM: Homo sapiens

<400> SEQUENCE: 69
agccccaagc ttaccacctg cacccggaga gctgtgtcac catgtgggtc ccggttgtct      60
tcctcaccct gtccgtgacg tggattggtg ctgcacccct catcctgtct cggattgtgg     120
gaggctggga gtgcgagaag cattcccaac cctggcaggt gcttgtggcc tctcgtggca     180
gggcagtctg cggcggtgtt ctggtgcacc ccagtgggt cctcacagct gcccactgca     240
tcaggaacaa aagcgtgatc ttgctgggtc ggcacagcct gtttcatcct gaagacacag     300
gccaggtatt tcaggtcagc cacagcttcc cacacccgct ctacgatatg agcctcctga     360
agaatcgatt cctcaggcca ggtgatgact ccagccacga cctcatgctg ctccgcctgt     420

-continued

```
cagagcctgc cgagctcacg gatgctgtga aggtcatgga cctgcccacc caggagccag    480
cactggggac cacctgctac gcctcaggct ggggcagcat tgaaccagag gagttcttga    540
ccccaaagaa acttcagtgt gtggacctcc atgttatttc caatgacgtg tgtgcgcaag    600
ttcaccctca gaaggtgacc aagttcatgc tgtgtgctgg acgctggaca gggggcaaaa    660
gcacctgctc gggtgattct gggggcccac ttgtctgtaa tggtgtgctt caaggtatca    720
cgtcatgggg cagtgaacca tgtgccctgc ccgaaaggcc ttccctgtac accaaggtgg    780
tgcattaccg gaagtggatc aaggacacca tcgtggccaa ccccctgagca ccctatcaa    840 cccctattg tagtaaactt ggaaccttgg aaatgaccag gccaagactc aagcctcccc    900
agttctactg acctttgtcc ttaggtgtga ggtccagggt tgctaggaaa agaaatcagc    960
agacacaggt gtagaccaga gtgtttctta aatggtgtaa ttttgtcctc tctgtgtcct   1020
ggggaatact ggccatgcct ggagacatat cactcaattt ctctgaggac acagatagga   1080
tggggtgtct gtgttatttg tggggtacag agatgaaaga ggggtgggat ccacactgag   1140
agagtggaga gtgacatgtg ctggacactg tccatgaagc actgagcaga agctggaggc   1200
acaacgcacc agacactcac agcaaggatg gagctgaaaa cataacccac tctgtcctgg   1260
aggcactggg aagcctagag aaggctgtga gccaaggagg gagggtcttc ctttggcatg   1320
ggatggggat gaagtaagga gagggactgg accccctgga agctgattca ctatgggggg   1380
aggtgtattg aagtcctcca gacaaccctc agatttgatg atttcctagt agaactcaca   1440
gaaataaaga gctgttatac tgtg                                          1464
```

<210> SEQ ID NO 70
<211> LENGTH: 9
<212> TYPE: PRT
<213> ORGANISM: Artificial Sequence
<220> FEATURE:
<223> OTHER INFORMATION: PSA peptide

<400> SEQUENCE: 70

Ile Val Gly Gly Trp Glu Cys Glu Lys
1               5

<210> SEQ ID NO 71
<211> LENGTH: 12
<212> TYPE: PRT
<213> ORGANISM: Artificial Sequence
<220> FEATURE:
<223> OTHER INFORMATION: PSA peptide

<400> SEQUENCE: 71

Leu Ser Glu Pro Ala Glu Leu Thr Asp Ala Val Lys
1               5                   10

<210> SEQ ID NO 72
<211> LENGTH: 23
<212> TYPE: PRT
<213> ORGANISM: Artificial Sequence
<220> FEATURE:
<223> OTHER INFORMATION: CCL4 peptide

<400> SEQUENCE: 72

Asn Phe Val Val Asp Tyr Tyr Glu Thr Ser Ser Leu Cys Ser Gln Pro
1               5                   10                  15

Ala Val Val Phe Gln Thr Lys
            20

<210> SEQ ID NO 73
<211> LENGTH: 18
<212> TYPE: PRT
<213> ORGANISM: Artificial Sequence
<220> FEATURE:
<223> OTHER INFORMATION: CCL4 peptide

<400> SEQUENCE: 73

Ala Pro Met Gly Ser Asp Pro Pro Thr Ala Cys Cys Phe Ser Tyr Thr
1               5                   10                  15

Ala Arg

<210> SEQ ID NO 74
<211> LENGTH: 21
<212> TYPE: PRT
<213> ORGANISM: Artificial Sequence
<220> FEATURE:
<223> OTHER INFORMATION: CCL4 peptide

<400> SEQUENCE: 74

Gln Val Cys Ala Asp Pro Ser Glu Ser Trp Val Gln Glu Tyr Val Tyr
1               5                   10                  15

Asp Leu Glu Leu Asn
            20

<210> SEQ ID NO 75
<211> LENGTH: 16
<212> TYPE: PRT
<213> ORGANISM: Artificial Sequence
<220> FEATURE:
<223> OTHER INFORMATION: WISP peptide

<400> SEQUENCE: 75

Thr Ile Asp Val Ser Phe Gln Cys Pro Asp Gly Leu Gly Phe Ser Arg
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: WISP peptide

<400> SEQUENCE: 76

Ile Ser Asn Val Asn Ala Gln Cys Trp Pro Glu Gln Glu Ser Arg
1               5                   10                  15

<210> SEQ ID NO 77
<211> LENGTH: 16
<212> TYPE: PRT
<213> ORGANISM: Artificial Sequence
<220> FEATURE:
<223> OTHER INFORMATION: WISP peptide

<400> SEQUENCE: 77

Asp Thr Gly Ala Phe Asp Ala Val Gly Glu Val Glu Ala Trp His Arg
1               5                   10                  15

<210> SEQ ID NO 78
<211> LENGTH: 12
<212> TYPE: PRT
<213> ORGANISM: Artificial Sequence
<220> FEATURE:
<223> OTHER INFORMATION: WISP peptide

```
<400> SEQUENCE: 78

Tyr Asn Asn Gly Gln Ser Phe Gln Pro Asn Cys Lys
1               5                   10
```

PROSTATE CANCER-ASSOCIATED SECRETED PROTEINS

CROSS REFERENCE TO RELATED APPLICATION

This application claims the benefit of the earlier filing date of U.S. Provisional Application No. 62/432,946, filed Dec. 12, 2016, which is incorporated by reference in its entirety.

ACKNOWLEDGMENT OF GOVERNMENT SUPPORT

This invention was made with government support under the following contract numbers awarded by the National Institute of Health in its various agencies and programs: U01-CA111244; PC150752; CA86402; GM103493; this invention also arose under DEAC05-76RL01830 awarded by the Department of Energy. The government has certain rights in the invention.

FIELD

This application provides methods of diagnosing and/or treating prostate cancer, following determining expression levels of several prostate cancer-related secretory molecules, such as AGR2, AGR3, CRISP3, CCL3, CEACAM5, CEACAM6, IL24, MMP9, CXCL14, CD90, POSTN, and SFRP4, for example in a urine sample.

PARTIES TO JOINT RESEARCH AGREEMENT

This application describes and claims certain subject matter that was developed under a written joint research agreement between Battelle Memorial Institute and the University of Washington.

BACKGROUND

Prostate cancer is the one of the most common cancers diagnosed in the United States. A prostate cancer diagnosis can vary from a low- or intermediate-risk to a high-risk diagnosis, which means that the patient has a low-, intermediate-, or high-risk of pathological and biochemical outcomes after treatment (e.g., by radical prostatectomy); metastasis; prostate cancer-specific mortality; and all-cause mortality. A diagnosis of a particular risk category can determine the course of treatment, which can, for example, range from monitoring, in the case of low-risk cancers, to radiation or surgical procedures for higher risk cancers.

Common methods of screening for prostate cancer include a digital rectal exam (DRE) and serum prostate-specific antigen (sPSA) screening, which can be administered alone or in combination. The use of DRE is not favored by patients, and sPSA testing is controversial. One prostate cancer urine test measures the cancer-specific non-coding transcript PCA3 from released prostate cancer cells, but only has a sensitivity of 65% and a specificity of 66%.

Thus, while screening men for prostate cancer decreases mortality from the disease, a need remains for a more accurate and non-invasive means of screening for prostate cancer. There is also a need for an accurate, non-invasive means of distinguishing prostate cancer in different risk categories with the concern of overtreatment. For example, low-risk prostate cancer patients can remain healthy for a long time without undergoing invasive and painful surgery with potentially harmful side effects, and, thus, are considered ideal candidates for observation-based therapies, such as watchful waiting and active surveillance.

SUMMARY

It is shown herein that a combination of prostate cancer-related molecules, such as two or more of AGR2, AGR3, CRISP3, CCL3, CEACAM5, CEACAM6, IL24, MMP9, CXCL14, CD90, POSTN, and SFRP4, can be detected in patient urine samples (such as urine from a human subject) and can be used as biomarkers to diagnose and/or treat a patient with or at risk for prostate cancer. Further, it is demonstrated that biomarker MMP9 can distinguish with significant accuracy subjects with low-risk prostate cancer from subjects with intermediate- or high-risk prostate cancer.

Methods are provided for treating a subject with prostate cancer. Such methods can include measuring expression of at least two prostate cancer-related molecules in a sample obtained from a subject, including at least two of (such as 2, 3, 4, 5, 6, 7, 8, 9, 10, 11 or 12 of) the prostate cancer-related molecules AGR2, AGR3, CRISP3, CCL3, CEACAM5, CEACAM6, IL24, MMP9, CXCL14, CD90, POSTN, and SFRP4. In some examples, expression levels are normalized to PSA levels detected in urine. The methods can further include measuring increased expression of the at least two prostate cancer-related molecules, for example as compared to a control or reference value representing expression for each of the at least two prostate cancer-related molecules expected in a sample from a subject who does not have prostate cancer (e.g., as compared to a threshold of expression of any of these molecules established from a subject or subjects, such as a cohort of control subjects). In addition, the methods can include administering at least one of watchful waiting, active surveillance, surgery, radiation, hormone therapy, chemotherapy, brachytherapy, cryotherapy, ultrasound, bisphosphate therapy, biologic therapy, or vaccine therapy to the subject with prostate cancer, thereby treating the subject.

Methods are provided for diagnosing prostate cancer in a subject. The methods can include detecting the expression of at least two prostate cancer-related molecules in a sample obtained from a subject, including at least two of (such as 2, 3, 4, 5, 6, 7, 8, 9, 10, 11 or 12 of) the prostate cancer-related molecules AGR2, AGR3, CRISP3, CCL3, CEACAM5, CEACAM6, IL24, MMP9, CXCL14, CD90, POSTN, and SFRP4. In some examples, expression levels are normalized to PSA levels detected in urine. The methods can further include comparing the expression of the at least two prostate cancer-related molecules in the sample obtained from the subject to at least one control or reference value representing expression for each of the at least two prostate cancer-related molecules expected in a sample from a subject who does not have prostate cancer (e.g., as compared to a threshold of expression of any of these molecules established from a subject or subjects, such as a cohort of control subjects). In addition, the methods can include determining that the subject has prostate cancer when increased expression of the at least two prostate cancer-related molecules between the sample and the control is detected.

In some examples, the at least two prostate cancer-related molecules can include all of AGR2, AGR3, CRISP3, CCL3, CEACAM5, CEACAM6, IL24, MMP9, CXCL14, CD90, POSTN, and SFRP4; the combinations of prostate cancer-related molecules listed in FIG. 15; low-abundance molecules, such as AGR2, AGR3, CCL3, CEACAM5, and CEACAM6; or moderate-to-low-abundance molecules, such as CRISP3, IL24, MMP9, CXCL14, CD90, POSTN, and SFRP4.

Methods are provided for treating a subject with intermediate- or high-risk prostate cancer. The methods can include measuring expression of MMP9 in a sample obtained from a subject, which can be determined based on MMP9 protein concentration using at least one surrogate peptide of MMP9, and the surrogate peptide can be at least one of FQTFEGDLK (SEQ ID NO: 41) or LGLGADVAQVTGALR (SEQ ID NO: 42). In some examples, the MMP9 expression level is normalized to PSA levels detected in urine. The methods further include measuring increased expression of MMP9 in the sample obtained from the subject as compared to a control or reference value representing expression of MMP9 expected in a sample from a subject who has low-risk prostate cancer (e.g., as compared to a threshold of expression of MMP9 established from a subject or subjects, such as a cohort of control subjects). In addition, the methods can include administering treatment for intermediate- or high-risk prostate cancer, thereby treating the subject.

Methods are provided for diagnosing intermediate- or high-risk prostate cancer. The methods can include detecting expression of MMP9 in a sample obtained from a subject, which can be determined based on MMP9 protein concentration using at least one surrogate peptide of MMP9, and the surrogate peptide can be at least one of FQTFEGDLK (SEQ ID NO: 41) or LGLGADVAQVTGALR (SEQ ID NO: 42). In some examples, expression levels are normalized to PSA levels detected in urine. In further examples, the methods can include comparing MMP9 expression in the sample obtained from the subject to MMP9 expression expected in a sample from a subject who has low-risk prostate cancer (e.g., a reference value representing MMP9 expression expected in a subject with low-risk prostate cancer, such as a threshold of expression of MMP9 established from a subject or subjects, such as a cohort of control subjects). In addition, the methods can include determining that the subject has intermediate- or high-risk prostate cancer when increased expression of MMP9 between the sample and the control is detected.

In some examples, the methods can include determining expression based on protein concentration, which can be determined using the concentration of at least one surrogate peptide of the protein, such as a peptide listed in FIG. 4. In other examples, the methods can include determining the protein concentration using an immunoassay, such as an ELISA. In additional examples, the protein concentration can be determined using mass spectrometry, for example, using LC-SRM, LG-SRM, or PRISM-SRM.

In some other examples, the methods include normalizing expression of the at least two prostate cancer-related molecules to the amount of a prostate protein, such as PSA, which can be determined using, for example, at least one surrogate peptide of PSA, such as IVGGWECEK (SEQ ID NO: 70) or LSEPAELTDAVK (SEQ ID NO: 71).

In additional examples, the sample can be a urine sample, and, in further examples, the subject can be a human subject. In particular examples, the expression detected can have an AUC value of greater than 0.8, such as at least 0.85, at least 0.9, or at least 0.95. In particular examples, the disclosed methods have a sensitivity of at least 78 to 86% and specificity of at least 100%.

Also provided are methods that include treating a sample (e.g., urine sample) obtained from a subject (such as one known or suspected to have prostate cancer) with a protease and measuring expression of AGR2, AGR3, CEACAM5, CD90, and SFRP4, for example using mass spectrometry. In some examples, the methods also includes measuring expression of CRISPS, CCL3, CEACAM6, IL24, MMP9, CXCL14, and POSTN, for example using mass spectrometry. In some examples, one or more of the surrogate peptides disclosed herein (e.g., those in FIGS. 2, 4 and 15) are used to measure expression of these proteins, for example using mass spectrometry.

The foregoing and other objects and feature of the disclosure will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows a panel that lists the query result from the database UrinePA. The parameter "observed" indicates abundance.

FIG. 2 shows thirteen prostate cancer-associated secreted proteins and their surrogate peptides. For each surrogate peptide, the three best transitions without co-eluting interference were monitored. The "a" indicates that endogenous light peptides were detected in the pooled urine sample. The "b" indicates that cysteine was synthesized as carbamidomethyl cysteine. Peptides shown from top to bottom are SEQ ID NOS: 6-9, 18-20, 72-74, 23-26, 29-31, 12-15, 47-50, 34-37, 40-44, 58-61, 64-67, 53-55, and 75-78.

FIG. 4 shows prostate cancer-associated secreted proteins and their surrogate peptides. The "a" indicates that these surrogate peptides were confidently detected in the pooled urine sample. The "b" indicates that the cysteine was synthesized as carbamidomethyl cysteine. Peptides shown from top to bottom are SEQ ID NOS: 3, 6, 18, 23-25, 29-30, 12-13, 47-48, 34, 40-43, 58, 64, and 53-55.

FIGS. 5A-5F show correlation plots between any two MMP9 surrogate peptides in 20 urine samples. FIG. 5A shows a relative abundance correlation between FQTFEGDLK (y-axis; SEQ ID NO: 41) and AVIDDAFAR (x-axis; SEQ ID NO: 40); FIG. 5B shows a relative abundance correlation between LGLGADVAQVTGALR (y-axis; SEQ ID NO: 42) and AVIDDAFAR (x-axis; SEQ ID NO: 40); FIG. 5C shows a relative abundance correlation between SLGPALLLLQK (SEQ ID NO: 43) and AVIDDAFAR (SEQ ID NO: 40); FIG. 5D shows a relative abundance correlation between SLGPALLLLQK (y-axis; SEQ ID NO: 43) and LGLGADVAQVTGALR (x-axis; SEQ ID NO: 42); FIG. 5E shows a relative abundance correlation between LGLGADVAQVTGALR (y-axis; SEQ ID NO: 42) and FQTFEGDLK (x-axis; SEQ ID NO: 41); FIG. 5F shows a relative abundance correlation between SLGPALLLLQK (y-axis; SEQ ID NO: 43) and FQTFEGDLK (y-axis; SEQ ID NO: 41). L/H=the ratio of SRM signal from endogenous peptide over heavy-labeled internal standard. $R^2$ values range from 0.59 to 0.93.

FIG. 6A shows CD90 (with the removal of the point with the red circle, the correlation coefficient of $R^2$ significantly decreased from 0.70 to 0.21); FIG. 6B shows CRISP3 (with the removal of the point with the red circle, the correlation coefficient of $R^2$ significantly decreased from 0.65 to 0.14).

FIG. 7A shows the entire range of relative abundance of the peptides; FIG. 7B shows a small range of relative abundance. Data points with the blue dash circle significantly deviated from the correlation curve.

FIG. 8 shows a summary of SRM measurements of PSA protein in 27 clinical urine samples including 7 post-op subjects (two purified PSA internal standards, IVGGWECcamEK (SEQ ID NO: 70) and LSEPAELTDAVK (SEQ ID NO: 71), were spiked at 1 fmol/μL and 10 fmol/μL respectively). The "a" indicates that the L/H ratios were corrected according to the correlation curve of the two PSA surrogate peptides as well as the experimental observation (P06017Pre: the measured value of 0.828 was changed into 1.656; P07040Pre: the measured value of 0.261 was changed into 0.366; P08015Pre: the measured value of 3.240 was changed into 4.739).

FIG. 10 shows an estimation of the percentage of PSA from the post-op urine over PSA from the non-cancer urine (the surrogate peptide IVGGWEC$_{cam}$EK was used; SEQ ID NO: 70). The "a" indicates that the L/H ratios were corrected according to the correlation curve of the two PSA surrogate peptides (P07040Pre: the measured value of 0.261 was changed into 0.366; P08015Pre: the measured value of 3.240 was changed into 4.739).

FIGS. 11A-11B show a summary of multiplex SRM measurements of prostate cancer-associated secreted proteins in 20 clinical urine samples.

FIG. 12 shows the performance of surrogate peptide markers derived from 10 prostate cancer-associated secreted proteins in 20 urine samples (14 cancer and 6 non-cancer samples). The "a" indicates that P values were obtained from the Mann-Whitney U test. The "b" indicates that these are the sensitivity and specificity at the optimal cutoff point (i.e., the best sum of the sensitivity and specificity). The "c" indicates that the cysteine was synthesized as carbamidomethyl cysteine. Peptides shown from top to bottom are SEQ ID NOS: 3, 6, 12-13, 53-55, 47, 34, 40-43, and 64.

FIGS. 13A-13B show the SRM signal ratio of urinary secreted protein/PSA, i.e., (L/H)$_{peptide\ marker}$/(L/H)PSA from SRM measurements in 20 clinical urine samples (crude internal standards for prostate cancer-associated secreted proteins and purified internal standard for PSA surrogate peptide IVGGWECcamEK were spiked at 10 fmol/μL and 1 fmol/μL, respectively; SEQ ID NO: 70). The "a" indicates that the L/H ratios were corrected according to the correlation curve of the two PSA surrogate peptides (P07040Pre: the measured value of 0.261 was changed into 0.366; P08015Pre: the measured value of 3.240 was changed into 4.739). Peptides shown from left to right in FIG. 13A are SEQ ID NOS: 3, 6, 24, 29, 12-13, and 53-54. Peptides shown from left to right in FIG. 13B are SEQ ID NOS: 47, 34, 40-43, and 64.

FIG. 14A shows the CEACAM5 relative abundance between non-cancer (n=6) and cancer urine (n=14; P=0.322); FIG. 14B shows an ROC curve analysis of the relative abundance of CEACAM5 in the measured 20 urine samples; FIG. 14C shows CEACAM5/PSA concentration ratios between non-cancer and cancer (P=0.012); FIG. 14D shows an ROC curve analysis of the CEACAM5/PSA concentration ratios; FIG. 14E shows significant differentiation between non-cancer and cancer (P=0.0034) with the use of the best peptide combination; FIG. 14F shows an ROC curve analysis of the best peptide combination. The relative abundances of CEACAM5 and PSA were derived from their surrogate peptides, SDLVNEEATGQFR (SEQ ID NO: 23) and IVGGWECcamEK (SEQ ID NO: 70), respectively. The best peptide combination: LPQTLSR/AGR2 (SEQ ID NO: 3), LYTYEPR/AGR3 (SEQ ID NO: 6), SDLVNEEATGQFR/CEACAM5 (SEQ ID NO: 23), VTSLTACLVDQSLR/CD90 (SEQ ID NO: 54), and GVCISPEAIVTDLPEDVK/SFRP4 (SEQ ID NO: 64).

FIG. 15 shows selected combinations of multiple markers for achieving better discrimination than individual markers between cancer and non-cancer. The "a" indicates that the P values were obtained from the Mann-Whitney U test. The "b" indicates that these are the sensitivity and specificity at the optimal cutoff point (i.e., the best sum of the sensitivity and specificity). The "c" indicates that the cysteine was synthesized as carbamidomethyl cysteine. Peptides shown from top to bottom are SEQ ID NOS: 3, 6, 12-13, 23, 29, 34, 40-42, 54-55, and 64.

FIG. 16A shows an ROC plot for urinary AGR2 determined by ELISA. The P value obtained for this cohort was 0.01. FIG. 16B shows the urinary levels of AGR2 in a non-cancer healthy male (P16-050A-J), which were measured by ELISA using samples donated within a period of 14 days. Buffer was the negative control, and PC3 was the positive control. In bar 4, alcohol was added to P16-050A urine before the ELISA was performed.

FIG. 17 shows PSA concentrations in urine and serum for 20 measured subjects (urinary PSA and serum PSA concentrations were obtained from SRM measurements and ELISA measurements, respectively). The "a" indicates that the L/H ratios were corrected according to the correlation curve of the two PSA surrogate peptides (P07040Pre: the measured value of 0.261 was changed into 0.366; P08015Pre: the measured value of 3.240 was changed into 4.739).

FIGS. 18A-18B show the ratios of secreted protein over PSA concentrations, urinary PSA (uPSA) and serum PSA (sPSA) between low volume/low grade cancer (n=6) and significant cancer (n=5). The low volume/low grade cancer: Gleason score≤6 and tumor volume≤0.5 cc; the significant cancer: Gleason score>6 and tumor volume>0.5 cc. Peptides shown from left to right in FIG. 18A are SEQ ID NOS: 3, 6, 24, 29, and 12-13. Peptides shown from left to right in FIG. 18B are SEQ ID NOS: 53-55, 47, 34, 40-43, and 64.

FIG. 19A shows the relative abundance ratios of FQTFEGDLK/MMP9 over IVGGWECcamEK/PSA (SEQ ID NO: 41 and SEQ ID NO: 70) between low volume/low grade cancer (n=6) and significant cancer (n=5), P=0.022; FIG. 19B shows uPSA between low volume/low grade cancer and significant cancer (P=0.93); FIG. 19C shows a comparison of sPSA between low volume/low grade cancer and significant cancer (P=0.32).

SEQUENCE LISTING

Figure 3A:
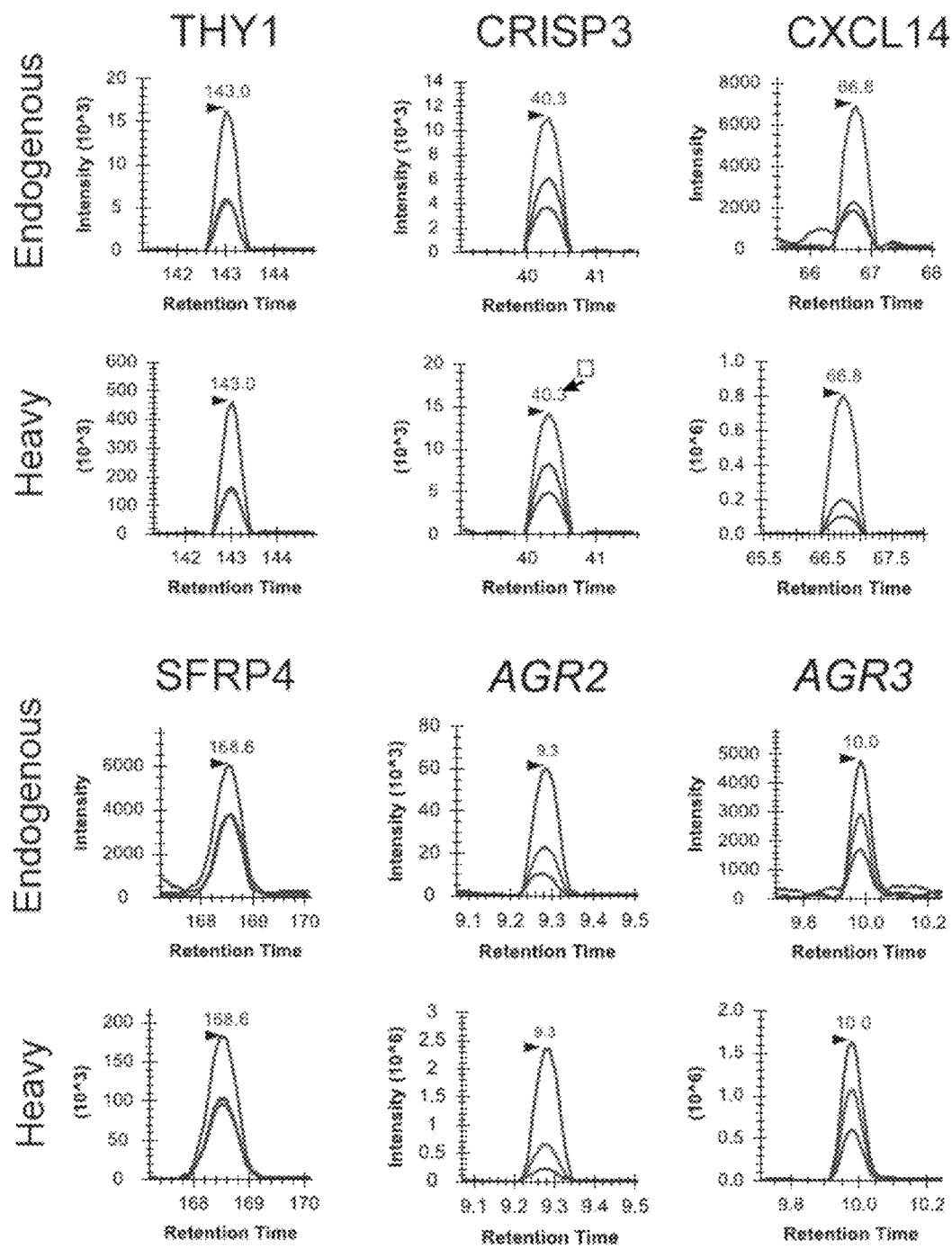
FIGS. 3A-3B show extracted ion chromatograms (XICs) of detected proteins in a single urine sample, P07-031C. Seven proteins (CD90, CRISP3, CXCL14, IL24, MMP9, POSTN, and SFRP4) were detected by LG-SRM, and the other five (AGR2, AGR3, CCL3, CEACAM5, and CEACAM6) were in extremely low abundance and were detected by PRISM-SRM. The monitored transitions for the surrogate peptides of each protein are THY1/CD90: VLYLSAFTSK (SEQ ID NO: 53), 564.8/916.5 (blue), 564.8/640.3 (chestnut), and 564.8/753.4 (purple); CRISP3: WANQCcamNYR (SEQ ID NO: 12), 556.2/854.3 (purple), 556.2/925.4 (blue), and 556.2/612.3 (chestnut); CXCL14: MVIITTK (SEQ ID NO: 47), 403.2/575.4 (purple), 403.2/674.4 (blue), and 403.2/462.3 (chestnut); IL24: LWEAFWAVK (SEQ ID NO: 34), 575.3/850.4 (blue), 575.3/721.4 (purple), and 575.3/650.4 (chestnut); MMP9: AVIDDAFAR (SEQ ID NO: 40), 489.3/807.4 (blue), 489.3/694.3 (purple), and 489.3/579.3 (chestnut); POSTN: AAAITSDILEALGR (SEQ ID NO: 58), 700.9/1074.8 (blue), 700.9/973.5 (purple), and 700.9/771.5 (chestnut); SFRP4: GVCcamISPEAIVTDLPEDVK (SEQ ID NO: 64), 971.5/587.3 (chestnut), 971.5/916.5 (blue), and 971.5/1425.7 (purple); AGR2: LPQTLSR (SEQ ID NO: 3), 407.7/351.2 (chestnut), 407.7/476.2 (purple), and 407.7/604.3 (blue); AGR3: LYTYEPR (SEQ ID NO: 6), 471.2/665.3 (blue), 471.2/272.2 (purple), and 471.2/277.2 (chestnut); CCL3: QVCcamADPSEEWVQK (SEQ ID NO: 16), 788.4/1002.5 (chestnut), 788.4/1117.5 (purple), and 788.4/1188.6 (blue); CEACAM5: SDLVNEEATGQFR (SEQ ID NO: 23), 733.3/679.4 (blue), 733.3/1051.5 (chestnut), and 733.3/937.4 (purple); CEACAM6: SDPVTLNVLYGPDGPTISPSK (SEQ ID NO: 30), 1079.1/1055.5 (blue), 1079.1/331.2 (chestnut), and 1079.1/998.5 (purple).

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Dec. 6, 2017, 80 KB, which is incorporated by reference herein. In the accompanying sequence listing:

SEQ ID NOS: 1 and 2 are exemplary AGR2 amino acid and nucleic acid sequences, respectively.

SEQ ID NO: 3 is an amino acid sequence of an AGR2 peptide.

SEQ ID NO: 4 and 5 are exemplary AGR2 amino acid and nucleic acid sequences, respectively.

SEQ ID NOS: 6-9 are exemplary ARG3 peptide sequences.

SEQ ID NOS: 10 and 11 are exemplary CRISP3 amino acid and nucleic acid sequences, respectively.

SEQ ID NOS: 12-15 are exemplary CRISP3 peptide sequences.

SEQ ID NOS: 16 and 17 are exemplary CCL3 amino acid and nucleic acid sequences, respectively.

SEQ ID NOS: 18-20 are exemplary CCL3 peptide sequences.

SEQ ID NOS: 21-22 are exemplary CEACAM5 amino acid and nucleic acid sequences, respectively.

SEQ ID NOS: 23-26 are exemplary CEACAM5 peptide sequences.

SEQ ID NO: 27 are exemplary CEACAM6 amino acid and nucleic acid sequences, respectively.

SEQ ID NOS: 29-31 are exemplary CEACAM6 peptide sequences.

SEQ ID NOS: 32-33 are exemplary IL24 amino acid and nucleic acid sequences, respectively.

SEQ ID NOS: 34-37 are exemplary IL24 peptide sequences.

SEQ ID NOS: 38-39 are exemplary MMP9 amino acid and nucleic acid sequences, respectively.

SEQ ID NOS: 40-44 are exemplary MMP9 peptide sequences.

SEQ ID NOS: 45-46 are exemplary CXCL14 amino acid and nucleic acid sequences, respectively.

SEQ ID NOS: 47-50 are exemplary CXCL14 peptide sequences.

SEQ ID NOS: 51-52 are exemplary CD90 amino acid and nucleic acid sequences, respectively.

SEQ ID NOS: 53-55 are exemplary CD90 peptide sequences.

SEQ ID NOS: 56-57 are exemplary POSTN amino acid and nucleic acid sequences, respectively.

SEQ ID NOS: 58-61 are exemplary POSTN peptide sequences.

SEQ ID NOS: 62-63 are exemplary SFRP4 amino acid and nucleic acid sequences, respectively.

SEQ ID NOS: 64-67 are exemplary SFRP4 peptide sequences.

SEQ ID NOS: 68-69 are exemplary PSA amino acid and nucleic acid sequences, respectively.

SEQ ID NOS: 70-71 are exemplary PSA peptide sequences.

SEQ ID NOS: 72-74 are exemplary CCL4 peptide sequences.

SEQ ID NOS: 75-78 are exemplary WISP peptide sequences.

DETAILED DESCRIPTION

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a protein" includes single or plural cells and is considered equivalent to the phrase "comprising at least one protein." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. Dates of GenBank® Accession Nos. referred to herein are the sequences available at least as early as Dec. 12, 2016. All references and GenBank® Accession numbers cited herein are incorporated by reference in their entirety.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

In order to facilitate review of the various embodiments of the disclosure, the following explanations of specific terms are provided:

Administration: To provide or give a subject a therapeutic intervention, such as a therapeutic drug, procedure, or protocol (e.g., for a subject with prostate cancer, docetaxel, prostatectomy, and active surveillance, respectively). Exemplary routes of administration for drug therapy include, but are not limited to, oral, injection (such as subcutaneous, intramuscular, intradermal, intraperitoneal, intratumoral, intraprostatic, and intravenous), sublingual, rectal, transdermal, intranasal, and inhalation routes.

Anterior gradient 2 (AGR2): Also known as AG2 (e.g., OMIM 606358); protein disulfide isomerase family A, member 17 (PD1A17 or member 17); or secreted cement gland protein XAG-2 homolog, AGR2 belongs to the protein disulfide isomerase (PDI) family. AGR2 plays a role in regulating the response to DNA damage as well as cell migration, growth, proliferation, and transformation. AGR2 overexpression plays a role in cancer and metastasis.

Includes AGR2 nucleic acid molecules and proteins. AGR2 sequences are publicly available. For example, GenBank® Accession Nos. NM_006408.3, NM_001106725.1, and NM_011783.2 disclose exemplary human, rat, and mouse AGR2 nucleotide sequences, respectively, and GenBank® Accession Nos. NP_006399.1, NP_001100195.1, and NP_035913.1 disclose exemplary human, rat, and mouse AGR2 protein sequences, respectively. One of ordinary skill in the art can identify additional AGR2 nucleic acid and protein sequences, including AGR2 variants that retain AGR2 biological activity (such as having increased levels in urine from a subject with prostate cancer).

Anterior gradient 3 (AGR3): Also known as AG3 (e.g., OMIM 609482); protein disulfide isomerase family A, member 18 (PD1A18 or member 18); or breast cancer membrane protein 11 (BCMP11), AGR3 belongs to the protein disulfide isomerase (PDI) family. AGR3 is expressed in certain epithelial and cancerous cells, such as breast and prostate cancer cells as well as cancerous epithelial cells, but exhibits restricted expression in most normal cells.

Includes AGR3 nucleic acid molecules and proteins. AGR3 sequences are publicly available. For example, GenBank® Accession Nos. NM_176813.4, NM_001106724.1, and NM_207531.3, disclose exemplary human, rat, and mouse AGR3 nucleotide sequences, respectively, and GenBank® Accession Nos. NP_789783.1, NP_001100194.1, and NP_997414.2 disclose exemplary human, rat, and mouse AGR3 protein sequences, respectively. One of ordinary skill in the art can identify additional AGR3 nucleic acid and protein sequences, including AGR3 variants that retain AGR3 biological activity (such as having increased levels in urine from a subject with prostate cancer).

Cluster Designation 90 (CD90): Also known as THY-1 T-cell antigen (THY1; e.g., OMIM 188230), CD90 is a cell surface glycoprotein in the immunoglobulin superfamily. CD90 is expressed by multiple cell types, including endothelial, smooth muscle, bone marrow, umbilical cord blood, fibroblasts and hemopoietic cells, and in tissues such as nervous and lymphoid tissues. Further, CD90 functions as a tumor suppressor and plays a role in cell adhesion and communication as well as immunity.

Includes CD90 nucleic acid molecules and proteins. CD90 sequences are publicly available. For example, GenBank® Accession Nos. BC065559.1, NM_012673.2, and NM_009382.3 disclose exemplary human, rat, and mouse CD90 nucleotide sequences, respectively, and GenBank® Accession Nos. NP_001298091.1, NP_036805.1, and NP_033408.1 disclose exemplary human, rat, and mouse CD90 protein sequences, respectively. One of ordinary skill in the art can identify additional CD90 nucleic acid and protein sequences, including CD90 variants that retain CD90 biological activity (such as having increased levels in urine from a subject with prostate cancer).

Carcinoembryonic antigen-related cell adhesion molecule 5 (CEACAM5): Also known as cluster of differentiation 66e (CD66e; e.g., OMIM 114890), CEACAM5 is an immunoreactive glycoprotein in the CEA (carcinoembryonic antigen) family. Many CEACAM family proteins are expressed in hematopoietic cells, and CEACAM5 plays a role in cell signaling, adhesion, differentiation, apoptosis, and polarity. Further, elevated levels of CEA proteins have been found in colorectal and other cancers as well as in patients with benign liver disease.

Includes CEACAM5 nucleic acid molecules and proteins. CEACAM5 sequences are publicly available. For example, GenBank® Accession Nos. NM_004363.5 and NM_028480.2 disclose exemplary human and mouse CEACAM5 nucleotide sequences, respectively, and GenBank® Accession Nos. NP_001278413.1 and NP_082756.1 disclose exemplary human and mouse CEACAM5 protein sequences, respectively. One of ordinary skill in the art can identify additional CEACAM5 nucleic acid and protein sequences, including CEACAM5 variants that retain CEACAM5 biological activity (such as having increased levels in urine from a subject with prostate cancer).

Carcinoembryonic antigen-related cell adhesion molecule 6 (CEACAM6): Also known as non-specific cross-reacting antigen (NCA; e.g., OMIM 163980), normal cross-reacting antigen CEA-like protein (CEAL), and cluster designation 66c (CD66c), CEACAM6 is a cell surface glycoprotein in the CEA family. CEACAM6 is expressed in neutrophils, affects tumor cell sensitivity to adenovirus infection, and is a receptor for *E. coli* adhesion to epithelial cells in patients with Crohn's disease. Further, CEACAM6 plays a role in platelet activation, signaling, and aggregation as well as cell surface interactions at the walls of blood vessels.

Includes CEACAM6 nucleic acid molecules and proteins. CEACAM6 sequences are publicly available. For example, GenBank® Accession Nos. NM_002483.6 and BC078962.1 disclose exemplary human and rat CEACAM6 nucleotide sequences, respectively, and GenBank® Accession Nos. NP_002474.4 and AAH78962.1 disclose exemplary human and rat CEACAM6 protein sequences, respectively. One of ordinary skill in the art can identify additional CEACAM6 nucleic acid and protein sequences, including CEACAM6 variants that retain CEACAM6 biological activity (such as having increased levels in urine from a subject with prostate cancer).

Chemokine (C—C Motif) ligand 3 (CCL3): Also known as small inducible cytokine A3 (SCYA3; e.g., OMIM 182283), macrophage inflammatory protein 1-α (MIP1α), and tonsillar lymphocyte LD78 α protein (LD78-α), CCL3 is a monokine involved in the acute inflammatory state of polymorphonuclear leukocyte recruitment and activation. CCL3 is expressed in many cell types, but most notably macrophages, dendritic cells, and lymphocytes. Further, CCL3 plays a key role in inflammation and the immune response to infection and can promote homeostasis.

Includes CCL3 nucleic acid molecules and proteins. CCL3 sequences are publicly available. For example, GenBank® Accession Nos. NM_002983.2, NM_013025.2, and NM_011337.2, disclose exemplary human, rat, and mouse CCL3 nucleotide sequences, respectively, and GenBank® Accession Nos. NP_002974.1, EDM05492.1, and NP_035467.1 disclose exemplary human, rat, and mouse CCL3 protein sequences, respectively. One of ordinary skill in the art can identify additional CCL3 nucleic acid and protein sequences, including CCL3 variants that retain CCL3 biological activity (such as having increased levels in urine from a subject with prostate cancer).

Control: A reference standard. In some embodiments, the control is a sample obtained from one or more subjects without prostate cancer (e.g., a urine sample from one or more subjects without prostate cancer). In other embodiments, the control is a sample obtained from one or more subjects without intermediate- or high-risk prostate cancer (e.g., a urine sample from one or more subjects with low-risk prostate cancer). In some embodiments, the control includes more than one subject, such as a cohort of control subjects. In still further embodiments, the control is a reference value, range of values, or threshold of values, such as from one or more subjects (e.g., a cohort). The historical control or standard (e.g., a previously tested control sample with a known prognosis or outcome or group of samples that represent baseline or normal values).

Cysteine-rich secretory protein 3 (CRISP3): Also known as CRSS and Aeg2, CRISP3 is in the cysteine-rich secretory protein subgroup of the CAP protein superfamily, the subgroup members of which are implicated in mammalian reproductive system function. CRISP3 is expressed in neutrophils, reproductive organs and glands, and the thymus and colon. CRISP3 plays a role in endometrial remodeling and repair (e.g., during the menstrual cycle and pregnancy), in prostate cancer, and immunity (e.g., in hepatitis C and Sjögren's syndrome).

Includes CRISP3 nucleic acid molecules and proteins. CRISP3 sequences are publicly available. For example, GenBank® Accession Nos. BC069602.1 and NM_009639.2 disclose exemplary human and mouse CRISP3 nucleotide sequences, respectively, and GenBank® Accession Nos. EAX04348.1 and AAI32539.1 disclose exemplary human and mouse CRISP3 protein sequences, respectively. One of ordinary skill in the art can identify additional CRISP3 nucleic acid and protein sequences, including CRISP3 variants that retain CRISP3 biological activity (such as having increased levels in urine from a subject with prostate cancer).

CXC motif, ligand 14 (CXCL14): Also known as small inducible cytokine subfamily B, member 14 (SCYB14; e.g., OMIM 604186), CXC chemokine in breast and kidney (BRAK), and MIP-2g, CXCL14 is a small cytokine in the CXC family. CXCL14 is expressed at high levels in many normal tissues, but is notably absent in many cancerous tissues. Further, CXCL14 plays a role in chemotaxis, homing, and activation for cells involved in the immune response and has been shown to inhibit angiogenesis.

Includes CXCL14 nucleic acid molecules and proteins. CXCL14 sequences are publicly available. For example, GenBank® Accession Nos. NM_004887.4, NM_001013137.2, and NM_019568.2 disclose exemplary human, rat, and mouse CXCL14 nucleotide sequences, respectively, and GenBank® Accession Nos. AAH03513.1, AAI01897.1, and AAH79661.1 disclose exemplary human, rat, and mouse CXCL14 protein sequences, respectively. One of ordinary skill in the art can identify additional CRISPS nucleic acid and protein sequences, including CXCL14 variants that retain CXCL14 biological activity (such as having increased levels in urine from a subject with prostate cancer).

Differential expression or altered expression: A difference, such as an increase or decrease, in the conversion of the information encoded in a gene (such as a prostate cancer-related gene) into messenger RNA, the conversion of mRNA to a protein, or both. In some examples, the difference is relative to a control or reference value, such as a threshold value of expression for each marker, for example from one or more subjects (e.g., a cohort of control subjects).

Detecting differential expression can include measuring a change in gene or protein expression, such as a change in expression of one or more prostate cancer-related genes or proteins disclosed herein.

Interleukin 24 (IL24): Also known as suppression of tumorigenicity 16 (ST16; e.g., OMIM 604136), melanoma differentiation-associated gene 7 (MDA7), ML-1, and IL-17F, IL24 is a cytokine and tumor-suppressing protein in the IL-10 family of cytokines. IL24 plays a role in cell survival and proliferation as well as wound healing, psoriasis, and cancer. Further, LI24 is expressed by cells involved in the immune response and can then act in skin, lung, and reproductive tissues.

Includes IL24 nucleic acid molecules and proteins. IL24 sequences are publicly available. For example, GenBank® Accession Nos. NM_006850.3, NM_133311.1, and NM_053095.2 disclose exemplary human, rat, and mouse IL24 nucleotide sequences, respectively, and GenBank® Accession Nos. NP_006841.1, NP_579845.1, and NP_444325.2 disclose exemplary human, rat, and mouse IL24 protein sequences, respectively. One of ordinary skill in the art can identify additional IL24 nucleic acid and protein sequences, including IL24 variants that retain IL24 biological activity (such as having increased levels in urine from a subject with prostate cancer).

Isolated: An "isolated" biological component (such as a nucleic acid molecule, protein, or cell) has been substantially separated or purified away from other biological components in the cell of the organism, or the organism itself, in which the component naturally occurs, such as other chromosomal and extra-chromosomal DNA and RNA, proteins and cells. Nucleic acid molecules and proteins that have been "isolated" include prostate cancer-related molecules (such as DNA or RNA) and proteins purified by standard purification methods. The term also embraces nucleic acid molecules, proteins and peptides prepared by recombinant expression in a host cell as well as chemically synthesized nucleic acid molecules and proteins. For example, an isolated protein, such as a prostate cancer-related protein, is one that is substantially separated from other types of proteins in a cell.

Label: An agent capable of detection, for example by mass spectrometry, ELISA, spectrophotometry, flow cytometry, or microscopy. For example, a label can be attached to a nucleic acid molecule or protein, thereby permitting detection of the nucleic acid molecule or protein. For example, a protein or peptide can be produced as a heavy, stable isotope, but as a protein or peptide with $^{13}C$ or $^{15}N$ incorporated as a heavy, stable isotope. Examples of labels include, but are not limited to, radioactive or heavy, stable isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Matrix metalloproteinase 9 (MMP9): Also known as collagenase type IV B (CLG4B; e.g., OMIM 120361), gelatinase B (GELB), collagenase type V, and 92-KD gelatinase, MMP9 is a 92-kD type IV collagenase and a member of the zinc metalloproteinase family. MMP9 is expressed in cells involved in the immune response and has been found in skin, lung, and synovial tissues. Further, as a matrix metalloproteinase, MMP9 aids in breaking down the extracellular matrix for normal physiological processes; MMP9 is involved in the immune response, angiogenesis, and wound repair and is associated with autoimmune diseases, cancer, and cardiovascular disease.

Includes MMP9 nucleic acid molecules and proteins. MMP9 sequences are publicly available. For example, GenBank® Accession Nos. NM_004994.2, NM_031055.1, and NM_013599.4 disclose exemplary human, rat, and mouse MMP9 nucleotide sequences, respectively, and GenBank® Accession Nos. EAW75776.1, EDL96479.1, and EDL06438.1 disclose exemplary human, rat, and mouse MMP9 protein sequences, respectively. One of ordinary skill in the art can identify additional MMP9 nucleic acid and protein sequences, including MMP9 variants that retain MMP9 biological activity (such as being increased in the urine of prostate cancer patients, particularly intermediate- to high-risk prostate cancer).

Periostin (POSTN): Also known as PN (e.g., OMIM 608777) and osteoblast-specific factor 2 (OSF2), POSTN is an extracellular matrix protein. POSTN is expressed in many normal tissues, including aortis, stomach, lower gastrointestinal tract, placental, uterine, and breast tissues. Further, POSTN plays a role in tissue development and regeneration as well as epithelial cell adhesion and migration; POSTN is involved in cancer stem cell maintenance and metastasis.

Includes POSTN nucleic acid molecules and proteins. POSTN sequences are publicly available. Nucleic acid and protein sequences for POSTN are publicly available. For example, GenBank® Accession Nos. BC106709.1, NM_001108550.1, and BC031449.1 disclose exemplary human, rat, and mouse POSTN nucleotide sequences, respectively, and GenBank® Accession Nos. AAI06710.1, NP_001102020.1, and AAH31449.1 disclose exemplary human, rat, and mouse POSTN protein sequences, respectively. One of ordinary skill in the art can identify additional POSTN nucleic acid and protein sequences, including POSTN variants that retain POSTN biological activity (such as being increased in the urine of prostate cancer patients).

Prostate-specific antigen (PSA): Also known as kallikrein-related peptidase 3 (kallikrein 3, KLK3; e.g., OMIM 176820); antigen, prostate-specific (APS); and gamma-seminoprotein, PSA is a glycoprotein and member of the kallikrein-related peptidase family. PSA is predominantly secreted by epithelial cells in the prostate gland and functions to dissolve cervical mucus to facilitate sperm entry into the uterus. PSA has been used to diagnose prostate cancer, as increased PSA levels in blood may suggest the presence of prostate cancer.

Includes PSA nucleic acid molecules and proteins. PSA sequences are publicly available. Nucleic acid and protein sequences for PSA are publicly available. For example, GenBank® Accession Nos. NM_001648.2, NM_012725.2, and NM_008455.3 discloses exemplary human PSA nucleotide sequences, respectively, and GenBank® Accession Nos. CAD54617.1, AAH89815.1, and NP_001639.1 discloses exemplary human PSA protein sequences. One of ordinary skill in the art can identify additional PSA nucleic acid and protein sequences, including PSA variants that retain PSA biological activity (such as being secreted by the prostate gland).

Prostate cancer: Also known as carcinoma of the prostate, prostate cancer is the development of cancer in the prostate, a gland in the male reproductive system. Prostate cancer is classified into different risk categories, including low-, intermediate-, and high-risk prostate cancer, which means that a patient has a low-, intermediate-, and high-risk, respectively, of pathological and biochemical outcomes after radical prostatectomy; metastasis; prostate cancer-specific mortality; and all-cause mortality (Cooperberg et al., J Cancer Inst., 101(12):878-887, 2009). One means of assessing the risk is using Gleason scoring: low-risk prostate cancer, Gleason score sum less than or equal to 6; intermediate-risk prostate cancer, Gleason score sum at 7; and high-risk prostate cancer, Gleason score sum greater than 7. Most prostate cancers are slow growing; however, some grow relatively quickly. The cancer cells may spread from the prostate to other parts of the body, particularly the bones and lymph nodes. It may initially cause no symptoms. In later stages, it can lead to difficulty urinating, blood in the urine, or pain in the pelvis, back or when urinating or to feeling tired due to low levels of red blood cells.

Prostate cancer can be diagnosed by biopsy. Medical imaging may then be done to determine if the cancer has spread to other parts of the body. Prostate cancer screening is controversial. Prostate-specific antigen (PSA) testing increases cancer detection but does not decrease mortality. The United States Preventive Services Task Force recommends against screening using the PSA test, due to the risk of overdiagnosis and overtreatment, as most cancer diagnosed would remain asymptomatic, and concludes that the potential benefits of testing do not outweigh the expected harms.

Many cases can be safely followed with active surveillance or watchful waiting. Other treatments may include a combination of surgery (such as cryotherapy), radiation therapy, hormone therapy, and chemotherapy. When it only occurs inside the prostate it may be curable. In those in whom the disease has spread to the bones, pain medications, bisphosphonates and targeted therapy, among others, may be useful. Outcomes depend on a person's age and other health problems as well as how aggressive and extensive the cancer is. Most people with prostate cancer do not die from the disease. The 5-year survival rate in the United States is 99%. Globally, it is the second most common type of cancer and the fifth leading cause of cancer-related death in men. Studies of males who died from unrelated causes have found prostate cancer in 30% to 70% of those over age 60.

Sample: A biological specimen containing genomic DNA, RNA (e.g., mRNA), protein, or combinations thereof, obtained from a subject. Examples include, but are not limited to, peripheral blood, serum, plasma, urine, ejaculate, saliva, tissue biopsy, fine needle aspirate, surgical specimen, and autopsy material. In one example, a sample is a urine sample from a subject with or at risk for prostate cancer, such as low-, intermediate-, or high-risk prostate cancer. In some examples, samples are used directly in the methods provided herein. In some examples, samples are manipulated prior to analysis using the disclosed methods, such as through concentrating, filtering, centrifuging, diluting, desalting, denaturing, reducing, alkylating, proteolyzing, or combinations thereof. In some examples, components of the samples are isolated or purified prior to analysis using the disclosed methods, such as isolating cells, proteins, and/or nucleic acid molecules from the samples.

Secreted frizzled-related protein 4 (SFRP4): Also known as frizzled-related protein (e.g., OMIM 606570) and human endometrium (FRPHE), SFRP4 is in the SFRP family, the members of which regulate Wnt signaling. SFRP4 is expressed in the endometrium, myocardium, breast tissue, and islets. Further, SFRP4 plays a role in regulating apoptosis, insulin secretion, and in regulating uterine morphology and function. SFRP4 is associated with bone diseases, such as rickets and bone cancers.

Includes SFRP4 nucleic acid molecules and proteins. SFRP4 sequences are publicly available. For example, GenBank® Accession Nos. NM_003014.3, NM_053544.1, and NM_016687.3 disclose exemplary human, rat, and mouse SFRP4 nucleotide sequences, respectively, and GenBank® Accession Nos. CAG46532.1, NP_445996.1, and AAH34853.1 disclose exemplary human, rat, and mouse SFRP4 protein sequences, respectively. One of ordinary skill in the art can identify additional SFRP4 nucleic acid and protein sequences, including SFRP4 variants that retain SFRP4 biological activity (such as being increased in the urine of prostate cancer patients).

Subject: Living multi-cellular vertebrate organisms, a category that includes mammals, such as human and non-human mammals, such as veterinary subjects (for example cats, dogs, cows, sheep, horses, pigs, and mice). In a particular example, a subject is one who has or is at risk for prostate cancer, such as low-, intermediate-, or high-risk prostate cancer. In a particular example, a subject is one who is suspected of having prostate cancer.

Therapeutically effective amount: An amount of a pharmaceutical preparation that alone, or together with a pharmaceutically acceptable carrier or one or more additional therapeutic agents, induces the desired response. A therapeutic agent, such as an anti-neoplastic chemotherapeutic agent, radiotherapeutic agent, or biologic agent, is administered in therapeutically effective amounts.

Therapeutic agents can be administered in a single dose, or in several doses, for example daily, during a course of treatment. However, the effective amount can be dependent on the source applied, the subject being treated, the severity and type of the condition being treated, and the manner of administration. Effective amounts of a therapeutic agent can be determined in many different ways, such as assaying for a sign or a symptom of an adenocarcinoma. Effective amounts also can be determined through various in vitro, in vivo or in situ assays. For example, a pharmaceutical preparation can decrease one or more symptoms of a prostate cancer, for example a decrease in the size of the prostate cancer, the number of tumors, the number of metastases, or other symptoms (or combinations thereof) by at least 20%, at least 50%, at least 70%, at least 90%, at least 98%, or even 100%, as compared to an amount in the absence of the pharmaceutical preparation.

Treating a disease: "Treatment" refers to a therapeutic intervention that ameliorates a sign or symptom of a disease or pathological condition, such a sign or symptom of prostate cancer. Treatment can also induce remission or cure of a condition, or can reduce the pathological condition, such as a reduction in tumor size, a reduction in tumor burden, a reduction in a sign or a symptom of a tumor (such as cachexia), a reduction in metastasis, or combinations thereof. In particular examples, treatment includes preventing a disease, for example by inhibiting the full development of a disease, such as decreasing the ability of a tumor to metastasize. Prevention of a disease does not require a total absence of disease.

Upregulated or activation: When used in reference to the expression of a nucleic acid molecule, such as a gene, refers to any process which results in an increase in the production of a gene product. A gene product can be RNA (such as mRNA, rRNA, tRNA, and structural RNA) or protein. Therefore, gene upregulation or activation includes processes that increase transcription of a gene or translation of mRNA, such as AGR2, AGR3, CRISP3, CCL3, CEACAM5, CEACAM6, IL24, MMP9, CXCL14, CD90, POSTN, and SFRP4.

Examples of processes that increase transcription include those that facilitate formation of a transcription initiation complex, those that increase transcription initiation rate, those that increase transcription elongation rate, those that increase processivity of transcription, and those that relieve transcriptional repression (for example, by blocking the binding of a transcriptional repressor). Gene upregulation can include inhibition of repression as well as stimulation of expression above an existing level. Examples of processes that increase translation include those that increase translational initiation, those that increase translational elongation and those that increase mRNA stability.

Gene upregulation includes any detectable increase in the production of a gene product, such as a protein. In certain examples, production of a gene product increases by at least 2-fold, at least 3-fold, at least 4-fold, or at least 5-fold, as compared to a control (e.g., as compared to a threshold of expression of any of these molecules established from a subject or subjects, such as a cohort of control subjects).

Overview

Provided herein are prostate cancer-associated secreted proteins that are found in increased levels in the urine of patients with prostate cancer, as compared to levels in urine from patients without prostate cancer. Sensitive multiplexed assays were developed for reliable simultaneous quantification of 12 detectable secreted proteins in urine. Except for CCL3 and POSTN, the other 10 proteins were reproducibly detected and quantified in all the urine samples analyzed with at least one surrogate peptide. The peptide signatures from AGR2, AGR3, CEACAM5, CD90 and SFRP4, in particular, produced an area-under-the curve (AUC) of 0.95. It was also observed that urinary MMP9 levels increased with higher risk cancer, which correlated with increase in MMP9 gene expression in Gleason pattern≥7 vs. Gleason≤6 prostate cancer subjects.

Samples of voided urine (≤100 ml) were collected without DRE from non-cancer controls, pre-op(erative), and post-op patients; post-pellet urine supernatant was spin concentrated (to <1 ml); urinary proteins were simultaneously measured by sensitive multiplex targeted proteomics. The quantification accuracy of each surrogate peptide assay was evaluated by correlation analysis of relative protein abundance between surrogate peptides from the same protein. The ability of measured markers to distinguish cancer from non-cancer was assessed by AUC values.

The secreted protein cancer-related biomarkers disclosed herein can generate an AUC over 0.9 for detecting prostate cancer. These markers were identified from their elevated expression in cell types of prostate tumors. Multimarker measurement can be accurately obtained, for example by using proteomics tools.

Accuracy in SRM assays depends on the surrogate peptides selected for each biomarker; the measured concentrations are directly proportional to the cognate protein analytes. As shown by the PSA surrogate peptides examined herein, unknown modifications on the analyte peptide sequences produce lower levels of measured concentrations compared with the true concentrations. Without modifications, the abundance ratio for any two or more surrogate peptides is constant across multiple samples analyzed, and a good correlation curve with no significant data point deviation is produced. Based on the correlation coefficients, the quantification accuracy of individual selected surrogate peptides of the secreted protein markers was assured, and the surrogate peptides were selected for SRM assay configuration for all subsequent testing. In studies involving human cell lines, most surrogate peptides (453/466) generated a high correlation coefficient ($R^2>0.8$) with no significant data point deviation (Worboys et al., Nat Methods 11:1041-4, 2014). Many surrogate peptides used in the urine analysis generated lower correlation coefficients (the median $R^2=0.70$) with data point deviations. This shows that the targeted protein molecules in urine of multiple patient samples are more varied, such as due to allelic differences or cancer-associated isoforms, than those in single cell lines. PSA measurement in urine, for example, was shown to be dependent on the peptide chosen. A single PSA peptide could not accurately quantify PSA in three of the urine samples (FIG. 8, urine IDs. P06017Pre, P07040Pre, and P08015Pre). A specific PSA proteoform encoded by SNP-L132I (rs2003783) is located within the LSEPAE(L/I)TDAVK (SEQ ID NO: 71) surrogate peptide. This newly identified PSA proteoform was observed in 9 out of 72 clinical serum samples (Végvári et al., Mol Cell Proteomics 12:2761-73, 2013) and in the P06017Pre urine. Abundance recalculations based on this information improved the correlation for this urine sample.

In addition to surrogate peptide selection, PSA normalization was used to account for the contribution of protein markers from sources other than the prostate. Without PSA normalization, the median values of the marker protein L/H ratios were lower in the non-cancer urine than the cancer urine, while, for CRISP3 and SFRP4, the median values in the non-cancer urine were higher than the cancer urine. For example, the L/H ratio for WANQCNYR (SEQ ID NO: 12) from CRISP3 in cancer was 0.29, and 0.38 in non-cancer. Given that CRISP3 and SFRP4 are produced by other sources in the urinary tract, this confounding result was not unexpected. Expression of CRISP3 and the non-secreted prostate cancer marker AMACR is localized to other tissues in the urinary tract. A similar finding for AGR2 in urine was obtained, even though a database query showed no detectable AGR2 in normal urine. One set of urine samples produced a 0.002 L/H ratio in cancer compared to 0.005 in non-cancer (Shi et al., J Proteome Res 13:875-82, 2014). AGR2 can originate from several other sources, such as the bladder and kidney. Although normal AGR2-expressing bladder urothelial cells do not secrete AGR2, unknown physiological factors could produce detectable levels of AGR2 in urine. While urinary CRISP3 and SFRP4 are constitutively produced by non-prostate sources, urinary AGR2 is transiently produced from non-prostate sources. Urinary PSA, on the other hand, is exclusively produced by the prostate. The significantly higher concentrations of urinary PSA found in some non-cancer samples could be due to donors with an enlarged prostate from benign hyperplasia. For example, prostate cancer patients with a prostate volume of 35 $cm^3$ (n=29) and benign prostatic hyperplasia patients prostate volume of 45 $cm^3$ (n=35) were measured to have median urinary PSA levels of 52.6 ng/mL and 123.2 ng/mL, respectively (Bolduc et al., Can Urol Assoc J 1:377-81, 2007). With PSA normalization, the performance of the disclosed prostate cancer protein biomarkers showed a near perfect AUC.

The use of the disclosed prostate cancer-related biomarkers reduces the need for prostate biopsy. In one example, prostate cancer diagnosis includes the use of the disclosed prostate cancer-related markers before or following an abnormal serum PSA result. Urine donation is convenient and does not require a DRE. With regard to the possibility that DRE might enhance marker signals, the levels of two post-DRE urine, P08-032C and P08-036N, were obtained. The signals from P08-032C (Gleason 4+3, tumor volume 1 cc) were not higher than those from others obtained without a DRE. DRE did not produce any increased signals in non-cancer P08-036N. With regard to possible age-related increases in marker levels, samples from a 76-year-old man (P08-018N) and a 53-year-old man (P08-022N) were analyzed. There was no detected increase in the background urinary levels of these proteins. It is possible that the baseline level of these markers may remain more or less constant with age. In contrast, an increase in serum PSA with age is known. In one example, if the prostate cancer-related protein panel result is negative (e.g., the analyzed proteins are not increased in the urine), no biopsy would be necessary if the negative predictive value is sufficiently high. Furthermore, the ratio of MMP9/PSA concentrations can be used to distinguish low volume/low grade prostate cancer from significant cancer. Therefore, effectively integrating the results from analyzing expression of the disclosed prostate cancer-related molecules will lead to greater detection of significant cancer with fewer biopsies performed in patients without cancer.

For AGR2 quantification, both mass spectrometry proteomics and ELISAs were used with good correlation, $R^2=0.91$, and similar AUC values (0.75). Thus, the disclosed prostate cancer-related biomarkers can be used for a multiplex ELISA to measure all these proteins simultaneously in a clinical setting. The equivalency in urinary AGR2 quantification by PRISM-SRM and ELISA shows that a multiplex ELISA can replicate the proteomics results, and clinical proteomics can make large-scale testing feasible.

Evaluating Expression in a Subject with a Risk of Prostate Cancer

Provided herein are methods of diagnosing a subject with a risk of prostate cancer and methods of treating a subject with prostate cancer (such as a human or veterinary subject). In particular examples, the methods can determine with high specificity, sensitivity, and accuracy (such as having an AUC of greater than 0.8, including, for example, at least 0.85, at least 0.9, at least 0.95, at least 0.96, at least 0.97, at least 0.98, or at least 0.99) whether a subject is likely to have prostate cancer. The prostate cancer can be any risk category of interest, including low- (Gleason score sum is 6 or lower), intermediate- (Gleason score sum is 7), and high-risk (Gleason score sum is above 7) prostate cancer. It is helpful to be able to determine whether or not a subject has prostate cancer because there are a variety of protocols for diagnosing prostate cancer but not all are specific, sensitive, and accurate. Hence, using the results of the disclosed assays to help distinguish subjects that are likely to have prostate cancer versus those not likely to have prostate cancer offers a substantial clinical benefit and allows subjects to be accurately diagnosed and, if a subject has prostate cancer, to be accurately treated.

In additional examples, the methods are utilized to determine whether or not to provide the subject with therapeutic intervention. In one example, a therapeutic intervention is administered. Thus, if the subject has prostate cancer, a therapeutic intervention, such as watchful waiting, active surveillance, surgery, radiation, hormone therapy, chemotherapy, brachytherapy, cryotherapy, ultrasound, bisphosphate therapy, biologic therapy, or vaccine therapy can be utilized. Using the results of the disclosed assays to help distinguish subjects that are likely to have prostate cancer versus those not likely to have prostate cancer offers a substantial clinical benefit because, where the subject has prostate cancer, the methods disclosed herein allow the subject to be selected for therapeutic intervention.

Methods of diagnosing a subject with a risk of prostate cancer and methods of treating a subject with prostate cancer, such as low-, intermediate-, or high-risk prostate cancer, are provided. Such methods can include measuring or detecting absolute or relative amounts of prostate cancer-related markers present in a sample (such as a urine sample) obtained from the subject, for example, using surrogate peptides of the marker proteins (e.g., as shown in FIGS. 4, 12 and 15) and/or antibodies, nucleic acid probes, and/or nucleic acid primers specific for each marker. In some examples, the prostate cancer-related markers can include at least 3, at least 4, at least 5, at least 6, at least 7, at least 8, at least 9, at least 10, at least 11 or all 12 of (such as 3, 4, 5, 6, 7, 8, 9, 10, 11 or 12 of) AGR2, AGR3, CRISP3, CCL3, CEACAM5, CEACAM6, IL24, MMP9, CXCL14, CD90, POSTN, and/or SFRP4. The expression levels of these markers can be measured. If increased protein and/or nucleic acid expression of the prostate cancer-related markers, for example, expression of AGR2, AGR3, CRISP3, CCL3, CEACAM5, CEACAM6, IL24, MMP9, CXCL14, CD90, POSTN, and/or SFRP4, in the sample is measured, the method can include administering therapeutic intervention to the subject, thereby treating the subject.

In some examples, measuring expression of prostate cancer-related markers, such as AGR2, AGR3, CRISP3, CCL3, CEACAM5, CEACAM6, IL24, MMP9, CXCL14, CD90, POSTN, and/or SFRP4, can include quantitating protein and/or nucleic acid expression of these markers in a sample obtained from the subject. In particular examples, these markers are first analyzed for measurement accuracy, such as correlating the amounts of different surrogate peptides from the same prostate cancer-related marker protein where the protein expression is measured.

In other examples, measuring increased protein or nucleic acid expression of the markers AGR2, AGR3, CRISP3, CCL3, CEACAM5, CEACAM6, IL24, MMP9, CXCL14, CD90, POSTN, and/or SFRP4 is relative to an amount of AGR2, AGR3, CRISP3, CCL3, CEACAM5, CEACAM6, IL24, MMP9, CXCL14, CD90, POSTN, and/or SFRP4 median protein or nucleic acid expression, respectively, for example a median value of protein or nucleic acid expression for each marker expected in a subject with no prostate cancer (e.g., as compared to a threshold of expression of any of these molecules established from a subject or subjects, such as a cohort of control subjects).

In some examples, measuring protein and/or nucleic acid expression of the markers AGR2, AGR3, CRISP3, CCL3, CEACAM5, CEACAM6, IL24, MMP9, CXCL14, CD90, POSTN, and/or SFRP4 can include measuring more than one marker, such as 2, 3, 4, 5, 6, 7, 8, 9, 10, 11, or all 12 of the markers. In other examples, any combination of these markers can be measured. In particular examples, any of the combinations of markers listed in FIG. 15 can be measured.

In some examples, measuring expression of prostate cancer-related markers, such as AGR2, AGR3, CRISP3, CCL3, CEACAM5, CEACAM6, IL24, MMP9, CXCL14, CD90, POSTN, and/or SFRP4, can include measuring the amount of protein expressed. For example, measuring the amount of protein expressed can include measuring a surrogate peptide from the protein. More than one surrogate peptide can be measured for a marker (e.g., see FIG. 2, FIG. 4, FIGS. 11A-B, FIGS. 13A-B, and FIGS. 18A-B), such as at least 2, at least 3, at least 4, at least 5, at least 6, at least 7, at least 8, at least 9, at least 10, at least 11, at least 12, at least 13, at least 14, at least 15, or at least 20 (such as 2, 3, 4, 5, 6, 7, 8, 9, 10, 11, 12, 13, 14, 15 or 20) surrogate peptides for a single marker. In some specific examples, surrogate peptides can be generated through contacting the protein (such as a sample containing the protein) with a protease, such a trypsin. Thus, in some examples, the methods includes treating a sample to be analyzed with a protease, such as trypsin. In some particular examples, surrogate peptides for the prostate cancer-related markers AGR2, AGR3, CRISP3, CCL3, CEACAM5, CEACAM6, IL24, MMP9, CXCL14, CD90, POSTN, and/or SFRP4 include the surrogate peptides listed in FIG. 4. In other particular examples, combinations of surrogate peptides for prostate cancer-related markers can be used, such as the combinations listed in FIG. 15.

In some examples, measuring the amount of protein expressed for prostate cancer-related markers, such as AGR2, AGR3, CRISP3, CCL3, CEACAM5, CEACAM6, IL24, MMP9, CXCL14, CD90, POSTN, and/or SFRP4, can include using mass spectroscopy and/or an immunoassay.

In particular examples, measuring the amount of protein expressed can include measuring the protein concentration using an immunoassay, such as an ELISA.

In some examples, measuring expression of prostate cancer-related markers, such as AGR2, AGR3, CRISP3, CCL3, CEACAM5, CEACAM6, IL24, MMP9, CXCL14, CD90, POSTN, and/or SFRP4, using the amount of protein expressed can include measuring the protein concentration using mass spectrometry. In some examples, mass spectrometry can be used to determine the protein concentration of the full-length protein and/or surrogate peptide(s) for the protein. In particular examples, mass spectrometry can be used to determine the protein concentration of prostate cancer-related markers, such as AGR2, AGR3, CRISP3, CCL3, CEACAM5, CEACAM6, IL24, MMP9, CXCL14, CD90, POSTN, and/or SFRP4, using surrogate peptides, such as the peptides listed in FIG. 4.

In particular examples, measuring expression of prostate cancer-related markers by using mass spectrometry can include using mass spectrometry assays such as LC-SRM, LG-SRM, and/or PRISM-SRM. In some examples, measuring expression of prostate cancer-related markers (such as in a serum sample) can include using an LC-SRM assay, for example, where the serum protein levels are least at a moderate abundance, such as about low μg/mL (e.g., 1-10, 10-50, 50-100, or 100-500 μg/mL).

In other examples, the measuring increased protein or nucleic acid expression of the markers AGR2, AGR3, CRISP3, CCL3, CEACAM5, CEACAM6, IL24, MMP9, CXCL14, CD90, POSTN, and/or SFRP4 includes measuring some markers that are at low-to-moderate abundance, for example, in the range of about low μg/mL to high ng/mL (e.g., 1-10 μg/mL, 500 ng/mL-1 μg/mL, or 100-500 ng/mL), in the sample obtained from the subject. In particular examples, the low-to-moderate-abundance markers in the sample can include CRISP3, IL24, MMP9, CXCL14, CD90, POSTN, and SFRP4. In some examples, these low-abundance markers can be accurately measured by using assays with sufficient sensitivity, such as an LG-SRM assay, a PRISM-SRM assay, and/or an ELISA.

In certain examples, measuring increased protein or nucleic acid expression of the markers AGR2, AGR3, CRISP3, CCL3, CEACAM5, CEACAM6, IL24, MMP9, CXCL14, CD90, POSTN, and/or SFRP4 includes measuring some markers that are at low abundance, for example, in the range of about low ng/mL to high pg/mL (e.g., 500-100 ng/mL, 100-50 ng/mL, 50-10 ng/mL, 10-1 ng/mL, 500 pg/mL-1 ng/mL, 500-100 pg/mL, or 100-50 pg/mL) in the sample obtained from the subject. In particular examples, the low-abundance markers in the sample can include AGR2, AGR3, CCL3, CEACAM5, and CEACAM6. In some examples, these low-abundance markers can be accurately measured by using assays with sufficient sensitivity, such as a PRISM-SRM assay and/or an ELISA.

In other examples, measuring increased protein or nucleic acid expression of prostate cancer-related markers, such as 2, 3, 4, 5, 6, 7, 8, 9, 10, 11, or 12 of AGR2, AGR3, CRISP3, CCL3, CEACAM5, CEACAM6, IL24, MMP9, CXCL14, CD90, POSTN, and/or SFRP4, includes normalizing expression of the prostate cancer-related molecules (such as surrogate peptides provided herein, such as those shown in FIG. 4 or 15) to the expression of a prostate molecule. In particular examples, the prostate molecule used for normalization can be PSA. In specific examples, normalizing to the PSA concentration can include normalizing the protein expression of a prostate cancer-related marker to the amount of PSA protein. In other examples, normalizing to the amount of PSA can include normalizing the protein expression of a prostate cancer-related marker to the amount of at least one surrogate peptide from the PSA protein. In certain examples, the PSA protein surrogate peptide(s) can include IVGGWECEK, LSEPAELTDAVK, or both.

In some examples, the methods can include measuring increased expression of two or more prostate cancer-related markers, such as AGR2, AGR3, CRISP3, CCL3, CEACAM5, CEACAM6, IL24, MMP9, CXCL14, CD90, POSTN, and/or SFRP4, which can include the combinations of markers listed in FIG. 15. In particular examples, the protein expression of the markers can be measured, for example, by using surrogate peptides of the markers, such as the surrogate peptides listed in FIG. 4. More than one surrogate peptide can be used for a marker (e.g., FIG. 2, FIG. 4, FIGS. 11A-B, FIGS. 13A-B, and FIGS. 18A-B), such as at least 2, at least 3, at least 4, at least 5, at least 6, at least 7, at least 8, at least 9, at least 10, at least 11, at least 12, at least 13, at least 14, at least 15, or at least 20 (such as 2, 3, 4, 5, 6, 7, 8, 9, 10, 11, 12, 13, 14, 15 or 20) surrogate peptides for a single protein marker. In specific examples, the amounts of surrogate peptides can be measured using mass spectrometry, such as LC-SRM, LG-SRM, and/or PRISM-SRM. In another example, the amounts of surrogate peptides are normalized to a prostate molecule, such as PSA, for example, by using one or more surrogate peptides of PSA (e.g., IVGGWECEK, SEQ ID NO: 70, LSEPAELTDAVK, SEQ ID NO: 71, or both). In specific examples, the increased expression measured for the at least two prostate cancer-related markers (such as 3, 4 5, 6, 7, 8, 9, 10, 11 or all 12 of AGR2, AGR3, CRISP3, CCL3, CEACAM5, CEACAM6, IL24, MMP9, CXCL14, CD90, POSTN, and SFRP4) has an AUC value greater than 0.80, such as an AUC value of 0.81, 0.82, 0.83, 0.84, 0.85, 0.86, 0.87, 0.88, or 0.89. In other specific examples, the increased expression measured for the at least two prostate cancer-related markers (such as 3, 4 5, 6, 7, 8, 9, 10, 11 or all 12 of AGR2, AGR3, CRISP3, CCL3, CEACAM5, CEACAM6, IL24, MMP9, CXCL14, CD90, POSTN, and SFRP4) has an AUC value greater than 0.90, such as an AUC value of 0.91, 0.92, 0.93, 0.94, 0.95, 0.96, 0.97, 0.98, or 0.99.

Methods of diagnosing intermediate- or high-risk prostate cancer and treating a subject with intermediate- or high-risk prostate cancer are provided. In particular examples, the methods can determine with significant accuracy whether a subject is likely to have prostate cancer associated with a specific risk category, such as low-, intermediate-, and high-risk prostate cancer. In particular examples, the methods can distinguish with significant accuracy between subjects that have low-risk prostate cancer and subjects that have intermediate-to-high-risk prostate cancer. It is helpful to be able to determine whether or not a subject has intermediate-to-high-risk prostate cancer because there are a variety of protocols for treating prostate cancer. Hence, using the results of the disclosed assays to help distinguish subjects that are likely to have prostate cancer associated with a specific risk category offers a substantial clinical benefit and allows subjects to be accurately diagnosed and, if a subject has prostate cancer associated with a specific risk category, to be accurately treated.

In some examples, methods of diagnosing intermediate- or high-risk prostate cancer and treating a subject with intermediate- or high-risk prostate cancer can include measuring a sample (such as a urine sample) obtained from the subject for example, using surrogate peptides of the marker proteins and/or antibodies, nucleic acid probes, and/or nucleic acid primers specific for the markers. In some examples, the prostate cancer-related markers can include MMP9. The expression levels of the markers can be measured. If increased protein and/or nucleic acid expression of one or more prostate cancer-related markers, for example, expression of MMP9, in the sample is measured, the method can include administering therapeutic intervention for intermediate- or high-risk prostate cancer to the subject, thereby treating the subject.

In particular examples, expression of MMP9 in a sample obtained from a subject is measured. In one example, the expression of MMP9 can be determined based on MMP9 protein concentration. In some examples, the expression of MMP9 protein can be measured using at least one surrogate peptide of MMP9. In specific examples, the surrogate peptide can be FQTFEGDLK (SEQ ID NO: 41), LGLGADVAQVTGALR (SEQ ID NO: 42), or both.

In further examples, measuring increased expression of MMP9 in the sample obtained from the subject can include comparing the expression of MMP9, such as by using the concentration of the MMP9 surrogate peptide(s) FQTFEGDLK (SEQ ID NO: 41) and/or LGLGADVAQVTGALR (SEQ ID NO: 42), to the amounts of MMP9 expression expected in a sample from a subject who has low-risk prostate cancer. In some specific examples, the surrogate peptides FQTFEGDLK (SEQ ID NO: 41) and LGLGADVAQVTGALR (SEQ ID NO: 42) for MMP9 protein can be used to measure expression of MMP9 with significant accuracy. In certain examples, the expression of MMP9 is increased compared to a sample from one or more subjects (such as a cohort of control subjects) who has low-risk prostate cancer, such as where the expression of MMP9 is increased compared with a sample from a subject who has low-risk prostate cancer with a P value of less than 0.05, such as a P value of 0.022 or a range of P values between 0.01-0.02, 0.02-0.03, 0.03-0.04, or 0.05.

In some examples, where an increase in the expression of MMP9 is measured in the sample obtained from the subject compared with the expression of MMP9 expected in a sample from a subject who has low-risk prostate cancer, the methods include administering treatment for intermediate- or high-risk prostate cancer, thereby treating the subject. For example, a patient with low-risk prostate cancer may not exhibit increased expression of MMP9 that exceeds the expression expected from a patient with low-risk prostate cancer and, therefore, may not necessarily be a good candidate for invasive treatments and/or treatments with potentially harmful side effects but, rather, may be a good candidate for watchful waiting or active surveillance. In another example, a patient with intermediate-to-high-risk prostate cancer may exhibit increased levels of MMP9 compared with the expression expected from a patient with low-risk prostate cancer and, therefore, may be better candidate for treatments such as surgery, radiation therapy, and hormone therapy but may not be a good candidate for observation-based treatments, such as watchful waiting or active surveillance.

Evaluating Nucleic Acid Expression

In some examples, expression of nucleic acids (e.g., RNA, mRNA, cDNA, genomic DNA) of prostate cancer-related markers, such as the markers AGR2, AGR3, CRISP3, CCL3, CEACAM5, CEACAM6, IL24, MMP9, CXCL14, CD90, POSTN, and/or SFRP4, are analyzed and, in some examples, quantified. Suitable biological samples can include urine, blood, plasma, or serum samples obtained from a subject having or a subject at risk for prostate cancer (such as intermediate- or high-risk prostate cancer). An increase in the amount of nucleic acid molecules for the prostate cancer-related markers, such as AGR2, AGR3, CRISP3, CCL3, CEACAM5, CEACAM6, IL24, MMP9, CXCL14, CD90, POSTN, and/or SFRP4, in the sample indicates that the subject has prostate cancer and/or has intermediate- or high-risk prostate cancer, as described herein. In some examples, expression of the prostate cancer-related nucleic acid molecule is normalized to PSA expression in the sample (such as by measuring PSA cDNA, genomic DNA, or mRNA in the urine sample). In some examples, the assay is multiplexed, in that expression of several nucleic acids are detected simultaneously or contemporaneously (Quek et al., *Prostate* 75:1886-95, 2015).

Nucleic acid molecules can be isolated from a sample from a subject having or a subject at risk for prostate cancer or for intermediate- or high-risk prostate cancer, such as a urine, blood, plasma, or serum sample. In one example, RNA isolation is performed using a purification kit, buffer set, and protease from commercial manufacturers, such as QIAGEN®, according to the manufacturer's instructions. RNA prepared from a biological sample can be isolated, for example, by guanidinium thiocyanate-phenol-chloroform extraction, and oligp(dT)-cellulose chromatography (e.g., Tan et al., *J Biomed Biotechnol.*, 2009: 574398, 10 pages, incorporated herein by reference in its entirety).

Methods of gene expression profiling include methods based on hybridization analysis of polynucleotides, methods based on sequencing of polynucleotides, and other methods in the art. In some examples, mRNA expression is quantified using northern blotting or in situ hybridization; RNAse protection assays, or PCR-based methods, such as reverse transcription polymerase chain reaction (RT-PCR) or real time quantitative RT-PCR. Alternatively, antibodies can be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE) and gene expression analysis by massively parallel signature sequencing (MPSS).

Evaluating Protein Expression

In some examples, protein expression of prostate cancer-related markers, such as AGR2, AGR3, CRISP3, CCL3, CEACAM5, CEACAM6, IL24, MMP9, CXCL14, CD90, POSTN, and/or SFRP4, is analyzed and, in some examples, quantified. Suitable biological samples include urine, ejaculate, blood, plasma, and/or serum samples obtained from a subject having or a subject at risk for prostate cancer, such as for intermediate- or high-risk prostate cancer. An increase in the amount of prostate cancer-related marker proteins, such as AGR2, AGR3, CRISP3, CCL3, CEACAM5, CEACAM6, IL24, MMP9, CXCL14, CD90, POSTN, and/or SFRP4 proteins, in the sample indicates that the subject has prostate cancer and/or has intermediate- or high-risk prostate cancer, as described herein. In some examples, expression of the prostate cancer-related protein is normalized to PSA expression in the sample (such as by measuring a surrogate peptide(s) for PSA in the urine sample). In some examples, the assay is multiplexed, in that expression of several proteins is detected simultaneously or contemporaneously.

The expression of prostate cancer-related markers, such as 2, 3, 4, 5, 6, 7, 8, 9, 10, 11 or 12 of AGR2, AGR3, CRISP3, CCL3, CEACAM5, CEACAM6, IL24, MMP9, CXCL14, CD90, POSTN, and/or SFRP4, can be measured using any of a number of techniques, such as direct physical measurements (e.g., mass spectrometry) or binding assays (e.g., immunoassays, agglutination assays, and immunochromatographic assays, such as ELISA, Western blot, or RIA assay). Immunohistochemical techniques can also be utilized for protein detection and quantification.

The method can include measuring or detecting a signal that results from a chemical reaction, e.g., a change in optical absorbance, a change in fluorescence, the generation of chemiluminescence or electrochemiluminescence, a change in reflectivity, refractive index or light scattering, the accumulation or release of detectable labels from the surface, the oxidation or reduction or redox species, an electrical current or potential, changes in magnetic fields, etc. Suitable detection techniques can detect binding events by measuring the participation of labeled binding reagents through the measurement of the labels via their photoluminescence (e.g., via measurement of fluorescence, time-resolved fluorescence, evanescent wave fluorescence, up-converting phosphors, multi-photon fluorescence, etc.), chemiluminescence, electrochemiluminescence, light scattering, optical absorbance, radioactivity, magnetic fields, enzymatic activity (e.g., by measuring enzyme activity through enzymatic reactions that cause changes in optical absorbance or fluorescence or cause the emission of chemiluminescence). In some examples, detection techniques are used that do not require the use of labels, e.g., techniques based on measuring mass (e.g., surface acoustic wave measurements), refractive index (e.g., surface plasmon resonance measurements), or the inherent luminescence of an analyte, such as a prostate cancer-related marker, for example, AGR2, AGR3, CRISP3, CCL3, CEACAM5, CEACAM6, IL24, MMP9, CXCL14, CD90, POSTN, and/or SFRP4.

For the purposes of quantitating proteins, a biological sample of the subject that includes cellular proteins (such as urine) can be used. Quantitation of prostate cancer-related marker proteins, such as AGR2, AGR3, CRISP3, CCL3, CEACAM5, CEACAM6, IL24, MMP9, CXCL14, CD90, POSTN, and/or SFRP4 proteins, can be achieved by immunoassay. The amount of prostate cancer-related marker proteins, such as AGR2, AGR3, CRISP3, CCL3, CEACAM5, CEACAM6, IL24, MMP9, CXCL14, CD90, POSTN, and/or SFRP4 proteins, can be assessed in the sample, for example by contacting the sample with appropriate antibodies (or antibody fragments) specific for each protein, and then detecting a signal (for example present directly or indirectly on the antibody, for example by the use of a labeled secondary antibody).

In one example, an electrochemiluminescence immunoassay is used, such as the V-PLEX™ system (Meso Scale Diagnostics, Rockville, Md.). In such assays, the primary antibodies for prostate cancer-related marker proteins, such as AGR2, AGR3, CRISP3, CCL3, CEACAM5, CEACAM6, IL24, MMP9, CXCL14, CD90, POSTN, and/or SFRP4 proteins, (or the corresponding secondary antibodies) are labeled with an electrochemiluminescent label.

Quantitative spectroscopic approaches methods, such as LC-SRM, LG-SRM, PRISM-SRM, and surface-enhanced laser desorption-ionization (SELDI), can be used to analyze expression of prostate cancer-related marker proteins, such as AGR2, AGR3, CRISP3, CCL3, CEACAM5, CEACAM6, IL24, MMP9, CXCL14, CD90, POSTN, and/or SFRP4 proteins, in, for example, a urine sample obtained from a subject having or a subject at risk for prostate cancer, such as for intermediate- or high-risk prostate cancer. In some such spectroscopy methods, at least one surrogate peptide for each prostate cancer-related marker protein is measured or detected in the sample (e.g., see FIGS. 4 and 15).

In one example, LC-SRM (liquid chromatography-selected reaction monitoring) may be used to detect protein expression for example by using a triple quadrupole spectrometer (see, e.g., U.S. Pub. No. 2013/0203096). LC-SRM is a liquid chromatography method that can be used for high-throughput selective and sensitive detection of molecules, such as prostate cancer-related proteins, for example, AGR2, AGR3, CRISP3, CCL3, CEACAM5, CEACAM6, IL24, MMP9, CXCL14, CD90, POSTN, and/or SFRP4. It can quantify moderately abundant analytes (low μg/mL) in limited sample volumes.

Therefore, in a particular example, the analytes can include prostate cancer-related marker proteins and/or surrogate peptides thereof, such as AGR2, AGR3, CRISP3, CCL3, CEACAM5, CEACAM6, IL24, MMP9, CXCL14, CD90, POSTN, and/or SFRP4 proteins and/or surrogate peptides thereof. In other examples, the fractionated and pooled analytes consist essentially of or consist of AGR2, AGR3, CRISP3, CCL3, CEACAM5, CEACAM6, IL24, MMP9, CXCL14, CD90, POSTN, and SFRP4 proteins or surrogate peptides thereof or of the combinations of proteins or surrogate peptides listed in FIG. 15. In this context, "consists essentially of" indicates that the fractionated and pooled analytes do not include other prostate cancer-related marker proteins that can be used to accurately predict prostate cancer, but can include other prostate molecules, such as prostate protein expression controls (e.g., PSA protein or surrogate peptides thereof).

In another example, LG-SRM (long gradient-selected reaction monitoring) can be used to detect protein expression, for example by using a reversed-phase C18 column and triple quadrupole spectrometer (see, e.g., Shi et al., Anal Chem., 85(19):9196-9203). LG-SRM is a liquid chromatography method for sensitive quantitation of analytes, such as prostate cancer-related proteins, and can even be used to accurately quantitate low-to-moderately abundant analytes (low μg/mL to high ng/mL), such as CRISP3, IL24, MMP9, CXCL14, CD90, POSTN, and SFRP4.

In LG-SRM, a long, shallow LC gradient (e.g., 5 hours compared with a conventional LC protocol that can be about 45 min) using a long LC column is followed by SRM as a second step. The eluting LC peaks containing the target analyte, such as prostate cancer-related proteins or surrogate peptides thereof, for example, AGR2, AGR3, CRISP3, CCL3, CEACAM5, CEACAM6, IL24, MMP9, CXCL14, CD90, POSTN, and/or SFRP4 proteins or surrogate peptides thereof, are, thus, sufficiently separated and resolved for accurate quantitation via SRM.

Therefore, in a particular example, the target analytes include prostate cancer-related marker proteins and/or surrogate peptides thereof, such as AGR2, AGR3, CRISP3, CCL3, CEACAM5, CEACAM6, IL24, MMP9, CXCL14, CD90, POSTN, and/or SFRP4 proteins and/or surrogate peptides thereof. In other examples, the target analytes consist essentially of or consist of AGR2, AGR3, CRISP3, CCL3, CEACAM5, CEACAM6, IL24, MMP9, CXCL14, CD90, POSTN, and SFRP4 proteins or surrogate peptides thereof; of the combinations of proteins or surrogate peptides listed in FIG. 15; or of moderate-to-low-abundance proteins or surrogate peptides thereof, such as CRISP3, IL24, MMP9, CXCL14, CD90, POSTN, and SFRP4. In this context "consists essentially of" indicates that the target analytes do not include other prostate cancer-related marker proteins that can be used to accurately predict prostate cancer, but can include other prostate molecules, such as prostate protein expression controls (e.g., PSA protein or surrogate peptides thereof).

In an additional example, PRISM-SRM (high-pressure, high-resolution separations, intelligent selection, multiplexing-selected reaction monitoring) is used to detect protein expression, for example, by using an ultra-pressure LC (UPLC) system and a triple quadrupole spectrometer (see, e.g., U.S. Pub. No. 2014/0194304; Shi et al., PNAS, 109 (38):15395-15400 (2012); and Shi et al., J Proteome Res., 13(2):875-882 (2014)). PRISM-SRM is a liquid chromatography method for quantitating analyes, such as prostate cancer-related proteins, and can even be used to accurately quantitate low-abundance (low ng/mL to high pg/mL) analytes, such as AGR2, AGR3, CCL3, CEACAM5, and CEACAM6.

In PRISM-SRM, LC-SRM is used as a second step after the target analyte is enriched through a liquid chromatography pre-fractionation step, such as using reverse-phase chromatography. The fractions containing the target analyte, such as prostate cancer-related proteins or surrogate peptides thereof, for example, AGR2, AGR3, CRISP3, CCL3, CEACAM5, CEACAM6, IL24, MMP9, CXCL14, CD90, POSTN, and/or SFRP4 proteins or surrogate peptides thereof, can then be pooled. The pooled fractions are enriched in the target analyte(s) and can then undergo a second LC separation step followed by SRM analysis.

Therefore, in a particular example, the fractionated and pooled analytes include prostate cancer-related marker proteins and/or surrogate peptides thereof, such as AGR2, AGR3, CRISP3, CCL3, CEACAM5, CEACAM6, IL24, MMP9, CXCL14, CD90, POSTN, and/or SFRP4 proteins and/or surrogate peptides thereof. In other examples, the fractionated and pooled analytes consist essentially of or consist of AGR2, AGR3, CRISP3, CCL3, CEACAM5, CEACAM6, IL24, MMP9, CXCL14, CD90, POSTN, and SFRP4 proteins or surrogate peptides thereof; of the combinations of proteins or surrogate peptides listed in FIG. 15; or of low-abundance proteins or surrogate peptides thereof, such as AGR2, AGR3, CCL3, CEACAM5, and CEACAM6. In this context "consists essentially of" indicates that the fractionated and pooled analytes do not include other prostate cancer-related marker proteins that can be used to accurately predict prostate cancer, but can include other prostate molecules, such as prostate protein expression controls (e.g., PSA protein or surrogate peptides thereof).

In a further example, surface-enhanced laser desorption-ionization time-of-flight (SELDI-TOF) mass spectrometry is used to detect protein expression, for example by using the ProteinChip™ (Ciphergen Biosystems, Palo Alto, Calif.).

Prostate Cancer-Related Molecules

The disclosed prostate cancer-related molecules include AGR2, AGR3, CRISP3, CCL3, CEACAM5, CEACAM6, IL24, MMP9, CXCL14, CD90, POSTN, SFRP4, and PSA. One or more of the disclosed prostate cancer-related molecules can be used alone or in any combination. The molecules can include proteins, peptides (e.g., surrogate peptides, see FIGS. 2, 4, and 15 for example), and nucleic acids.

In some embodiments, one of the disclosed prostate cancer-related molecules can include AGR2 (e.g., SEQ ID NOS: 1-3). In some embodiments, one of the disclosed prostate cancer-related molecules can include AGR3 (e.g., SEQ ID NOS: 4-9). In some embodiments, one of the disclosed prostate cancer-related molecules can include CRISP3 (e.g., SEQ ID NOS: 10-15). In some embodiments, one of the disclosed prostate cancer-related molecules can include CCL3 (e.g., SEQ ID NOS: 16-20). In some embodiments, one of the disclosed prostate cancer-related molecules can include CEACAM5 (e.g., SEQ ID NOS: 21-26). In some embodiments, one of the disclosed prostate cancer-related molecules can include CEACAM6 (e.g., SEQ ID NOS: 27-31). In some embodiments, one of the disclosed prostate cancer-related molecules can include IL24 (e.g., SEQ ID NOS: 32-37). In some embodiments, one of the disclosed prostate cancer-related molecules can include MMP9 (e.g., SEQ ID NOS: 38-44). In some embodiments, one of the disclosed prostate cancer-related molecules can include CXCL14 (e.g., SEQ ID NOS: 45-50). In some embodiments, one of the disclosed prostate cancer-related molecules can include CD90 (e.g., SEQ ID NOS: 51-55). In some embodiments, one of the disclosed prostate cancer-related molecules can include POSTN (e.g., SEQ ID NOS: 56-61). In some embodiments, one of the disclosed prostate cancer-related molecules can include SFRP4 (e.g., SEQ ID NOS: 62-67). In some embodiments, one of the disclosed prostate cancer-related molecules can include PSA (e.g., SEQ ID NOS: 68-71). In some examples, combinations of these prostate cancer-related molecules are used, such as 2, 3, 4, 5, 6, 7, 8, 9, 10, 11, 12, or 13 of these.

Molecules that are similar to the prostate cancer-related molecules disclosed above can be used as well as fragments thereof that retain biological activity. These molecules may contain variations, substitutions, deletions, or additions (e.g., the variation carbamidomethyl cysteine may be used instead of cysteine). The differences can be in regions not significantly conserved among different species. Such regions can be identified by aligning the amino acid sequences of related proteins from various animal species. Generally, the biological effects of a molecule are retained. For example, a molecule at least 75%, 80%, 85%, 90%, 95%, 96%, 97%, 98% or 99% identical to one of these molecules can be utilized. Molecules are of use that include at most 1, 2, 3, 4, 5, 6, 7, 8, 9, or 10 conservative amino acid substitutions. Generally, molecules are of use provided they retain at least 75%, 80%, 85%, 90%, 95%, 96%, 97%, 98% or 99% of the biological function of the native molecule, or have increased biological function as compared to the native molecule.

Administration of Therapy

Subjects analyzed with the disclosed methods and who are found to have prostate cancer can be selected for treatment. For example, subjects with prostate cancer or with intermediate-to-high-risk prostate cancer found to have increased expression of AGR2, AGR3, CRISP3, CCL3, CEACAM5, CEACAM6, IL24, MMP9, CXCL14, CD90, POSTN, and SFRP4 can be administered therapy for prostate cancer. Currently, the standard of care for prostate cancer can vary, but level of risk can be a factor. For example, a subject may be found to have low-risk prostate cancer, such as a patient with increased levels of AGR2, AGR3, CRISP3, CCL3, CEACAM5, CEACAM6, IL24, MMP9, CXCL14, CD90, POSTN, and SFRP4 but with MMP9 levels expected from a patient with low-risk prostate cancer. In some examples, subjects with low-risk prostate cancer may be treated using watchful waiting or active surveillance, both of which entail monitoring the cancer for changes and the subject for symptoms. Given that more invasive treatments entail a greater potential for side effects, studies suggest that active surveillance is the best choice for patients with low-risk prostate cancer.

In other examples, surgical removal of the prostate can be a treatment for low-risk prostate cancer or prostate cancers that do not respond to radiation therapy. In additional examples, subjects with any stage of prostate cancer, such as subjects with increased expression of AGR2, AGR3, CRISP3, CCL3, CEACAM5, CEACAM6, IL24, MMP9, CXCL14, CD90, POSTN, and SFRP4 can be treated with radiation therapy, such as using ionizing radiation to kill prostate cancer cells. In some other examples, subjects with either low- or intermediate-risk prostate cancer can be treated using brachytherapy, for example, where small radioactive particles, such as iodine-125 or palladium-103, are directly injected into the tumor, providing localized X-rays at the site of the tumor. In additional examples, ultrasound, such as high-intensity focused ultrasound (HIFU) is used where a subject has a recurrent case of prostate cancer, such as where a subject was successfully treated for prostate cancer but subsequently had increased expression of AGR2, AGR3, CRISP3, CCL3, CEACAM5, CEACAM6, IL24, MMP9, CXCL14, CD90, POSTN, and SFRP4.

In further examples, a subject can be treated with hormone therapy, such as by modulating the levels of testosterone in the body, where the subject has either recurrent prostate cancer, for example, a subject that was successfully treated for prostate cancer but subsequently had increased expression of AGR2, AGR3, CRISP3, CCL3, CEACAM5, CEACAM6, IL24, MMP9, CXCL14, CD90, POSTN, and SFRP4, or a subject that has high-risk prostate cancer, for example, a subject that has increased expression of AGR2, AGR3, CRISP3, CCL3, CEACAM5, CEACAM6, IL24, MMP9, CXCL14, CD90, POSTN, and SFRP4 and increased expression of MMP9 compared with the expression expected from a patient with low-risk prostate cancer (e.g., as compared to a threshold of expression of any of these molecules established from one or more subjects, such as a cohort of control subjects).

In some examples, at least a portion of the prostate cancer is surgically removed (for example via cryotherapy), irradiated, chemically treated (for example via chemoembolization), or combinations thereof, as part of the therapy. For example, a subject having prostate cancer can have all or part of the tumor surgically excised prior to administration of additional therapy.

Exemplary agents that can be used include one or more anti-neoplastic agents, such as radiation therapy, chemotherapeutic, biologic (e.g., immunotherapy), and anti-angiogenic agents or therapies. Methods and therapeutic dosages of such agents are known to those skilled in the art, and can be determined by a skilled clinician. These therapeutic agents (which are administered in therapeutically effective amounts) and treatments can be used alone or in combination. In some examples, 1, 2, 3, 4 or 5 different antineoplastic agents are used as part of the therapy.

In one example the therapy includes administration of one or more chemotherapy immunosuppressants (such as Rituximab, steroids) or cytokines (such as GM-CSF). Chemotherapeutic agents are known (see for example, Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2nd ed., 2000 Churchill Livingstone, Inc; Baltzer and Berkery. (eds): Oncology Pocket Guide to Chemotherapy, 2nd ed. St. Louis, Mosby-Year Book, 1995; Fischer Knobf, and Durivage (eds): The Cancer Chemotherapy Handbook, 4th ed. St. Louis, Mosby-Year Book, 1993). Exemplary chemotherapeutic agents that can be used with the therapy include but are not limited to, carboplatin, cisplatin, paclitaxel, docetaxel, doxorubicin, epirubicin, cabaziatxel, estramustine, vinblastine, topotecan, irinotecan, gemcitabine, iazofurine, etoposide, vinorelbine, tamoxifen, valspodar, cyclophosphamide, methotrexate, fluorouracil, mitoxantrone, and Doxil® (liposome encapsulated doxiorubicine). In one example the therapy includes docetaxel and prednisone. In one example the therapy includes cabaziatxel.

In one example, the therapy includes administering one or more of a microtubule binding agent, DNA intercalator or cross-linker, DNA synthesis inhibitor, DNA and/or RNA transcription inhibitor, antibodies, enzymes, enzyme inhibitors, and gene regulators.

Microtubule binding agents interact with tubulin to stabilize or destabilize microtubule formation thereby inhibiting cell division. Examples of microtubule binding agents that can be used as part of the therapy include, without limitation, paclitaxel, docetaxel, vinblastine, vindesine, vinorelbine (navelbine), the epothilones, colchicine, dolastatin 10, nocodazole, and rhizoxin. Analogs and derivatives of such compounds also can be used. For example, suitable epothilones and epothilone analogs are described in International Publication No. WO 2004/018478. Taxoids, such as paclitaxel and docetaxel, as well as the analogs of paclitaxel taught by U.S. Pat. Nos. 6,610,860; 5,530,020; and 5,912,264 can be used.

The following classes of compounds can be used as part of the therapy: suitable DNA and/or RNA transcription regulators, including, without limitation, anthracycline family members (for example, daunorubicin, doxorubicin, epirubicin, idarubicin, mitoxantrone, and valrubicin) and actinomycin D, as well as derivatives and analogs thereof. DNA intercalators and cross-linking agents that can be administered to a subject include, without limitation, platinum compounds (for example, carboplatin, cisplatin, oxaliplatin, and BBR3464), mitomycins, such as mitomycin C, bleomycin, chlorambucil, cyclophosphamide, as well as busulfan, dacarbazine, estramustine, and temozolomide and derivatives and analogs thereof. DNA synthesis inhibitors suitable for use as therapeutic agents include, without limitation, methotrexate, 5-fluoro-5'-deoxyuridine, 5-fluorouracil and analogs thereof. Examples of suitable enzyme inhibitors include, without limitation, camptothecin, etoposide, exemestane, trichostatin and derivatives and analogs thereof. Suitable compounds that affect gene regulation include agents that result in increased or decreased expression of one or more genes, such as raloxifene, 5-azacytidine, 5-aza-2'-deoxycytidine, tamoxifen, 4-hydroxytamoxifen, mifepristone, and derivatives and analogs thereof. Kinase inhibitors include imatinib, gefitinib, and erolitinib that prevent phosphorylation and activation of growth factors.

In one example, the therapy includes folic acid (for example, methotrexate and pemetrexed), purine (for example, cladribine, clofarabine, and fludarabine), pyrimidine (for example, capecitabine), cytarabine, fluorouracil, gemcitabine, and derivatives and analogs thereof. In one example, the therapy includes a plant alkaloid, such as podophyllum (for example, etoposide) and derivatives and analogs thereof. In one example, the therapy includes an antimetabolite, such as cytotoxic/antitumor antibiotics, bleomycin, hydroxyurea, mitomycin, and derivatives and analogs thereof. In one example, the therapy includes a topoisomerase inhibitor, such as a topoisomerase I inhibitor (e.g., topotecan, irinotecan, indotecan, indimitecan, camptothecin and lamellarin D) or a topoisomerase II inhibitor (e.g., etoposide, doxorubicin, daunorubicin, mitoxantrone, amsacrine, ellipticines, aurintricarboxylic acid, ICRF-193, genistein, and HU-331), and derivatives and analogs thereof. In one example, the therapy includes a photosensitizer, such as aminolevulinic acid, methyl aminolevulinate, porfimer sodium, verteporfin, and derivatives and analogs thereof. In one example, the therapy includes a nitrogen mustard (for example, chlorambucil, estramustine, cyclophosphamide, ifosfamide, and melphalan) or nitrosourea (for example, carmustine, lomustine, and streptozocin), and derivatives and analogs thereof.

Other therapeutic agents, for example anti-tumor agents, that may or may not fall under one or more of the classifications above, also are suitable for therapy. By way of example, such agents include adriamycin, apigenin, rapamycin, zebularine, cimetidine, amsacrine, anagrelide, arsenic trioxide, axitinib, bexarotene, bevacizumab, bortezomib, celecoxib, estramustine, hydroxycarbamide, lapatinib, pazopanib, masoprocol, mitotane, tamoxifen, sorafenib, sunitinib, vandetanib, tretinoin, and derivatives and analogs thereof.

In one example, the therapy includes one or more biologics, such as a therapeutic antibody, such as monoclonal antibodies. Examples of such biologics that can be used include one or more of bevacizumab, cetuximab, panitumumab, pertuzumab, trastuzumab, bevacizumab (Avastin®), ramucirumab, and the like. In specific examples, the antibody or small molecules used as part of the therapy include one or more of the monoclonal antibodies cetuximab, panitumumab, pertuzumab, trastuzumab, bevacizumab (Avastin®), ramucirumab, or a small molecule inhibitor such as gefitinib, erlotinib, and lapatinib.

In some examples the therapy includes administration of one or more immunotherapies, which may include the biologics listed herein. In specific examples, the immunotherapy includes therapeutic cancer vaccines, such as those that target PSA (e.g., ADXS31-142), prostatic acid phosphatase (PAP) antigen, TARP, telomerase (e.g., GX301) or that deliver 5T4 (e.g., ChAdOx1 and MVA); antigens NY-ESO-1 and MUC1; antigens hTERT and survivin; prostate-specific antigen (PSA) and costimulatory molecules (e.g., LFA-3, ICAM-1, and B7.1) directly to cancer cells, such as rilimogene galvacirepvac. Other examples of therapeutic vaccines include DCVAC, sipuleucel-T, pTVG-HP DNA vaccine, pTVG-HP, JNJ-64041809, PF-06755992, PF-06755990, and pTVG-AR. In other examples, the immunotherapy includes oncolytic virus therapy, such as aglatimagene besadenovec, HSV-tk, and valacyclovir. In additional examples, the immunotherapy can include checkpoint inhibitors, such as those that target PD-1 (e.g., nivolumab, pembrolizumab, durvalumab, and atezolizumab), CTLA-4

(e.g., tremelimumab and ipilimumab), B7-H3 (e.g., MGA271), and CD27 (e.g., CDX-1127). The protein MGD009 may also be used in another example. In specific examples, the immunotherapy can also include adoptive cell therapy, such as those that include T cells engineered to target NY-ESO-1 and those that include natural killer (NK) cells. In some examples, the immunotherapy can include adjuvant immunotherapies, such as sipuleucel-T, indoximod, and mobilan. In other specific examples, the immunotherapy includes one or more of tisotumab vedotin, sacituzumab govitecan, LY3022855, BI 836845, vandortuzumab vedotin, and BAY2010112, and MOR209/ES414. In additional examples, the immunotherapy can include cytokines, such as CYT107, AM0010, and IL-12.

In some examples, the subject receiving the therapy is also administered interleukin-2 (IL-2), as part of the therapy, for example via intravenous administration. In particular examples, IL-2 is administered at a dose of at least 500,000 IU/kg as an intravenous bolus over a 15 minute period every eight hours beginning on the day after administration of the peptides and continuing for up to 5 days. Doses can be skipped depending on subject tolerance.

In some examples, the subject receiving the therapy is also administered a fully human antibody to cytotoxic T-lymphocyte antigen-4 (anti-CTLA-4) as part of the therapy, for example via intravenous administration. In some example subjects receive at least 1 mg/kg anti-CTLA-4 (such as 3 mg/kg every 3 weeks or 3 mg/kg as the initial dose with subsequent doses reduced to 1 mg/kg every 3 weeks).

In one specific example for a subject with prostate cancer, such as a subject with increased expression of AGR2, AGR3, CRISP3, CCL3, CEACAM5, CEACAM6, IL24, MMP9, CXCL14, CD90, POSTN, and SFRP4, the therapy can include one or more of abiraterone acetate, bicalutamide, cabazitaxel, casodex (bicalutamide), degarelix, docetaxel, enzalutamide, flutamide, goserelin acetate, jevtana (cabazitaxel), leuprolide acetate, lupron (leuprolide acetate), lupron depot (leuprolide acetate), lupron depot-3 month (leuprolide acetate), lupron depot-4 month (leuprolide acetate), lupron depot-ped (leuprolide acetate), mitoxantrone hydrochloride, nilandron (nilutamide), nilutamide, provenge (sipuleucel-t), radium 223 dichloride, sipuleucel-T, taxotere (docetaxel), viadur (leuprolide acetate), xofigo (radium 223 dichloride), xtandi (enzalutamide), zoladex (goserelin acetate), and zytiga (abiraterone acetate).

In another specific example for a subject with prostate cancer, such as a subject with increased expression of AGR2, AGR3, CRISP3, CCL3, CEACAM5, CEACAM6, IL24, MMP9, CXCL14, CD90, POSTN, and SFRP4, the therapy can include one or more of chemotherapy drugs, such as cabazataxel (Jevtana®), docetaxel (Taxotere®), mitoxantrone (Teva®), or androgen deprivation therapy (ADT), such as with abiraterone Acetate (Zytiga®), bicalutamide (Casodex®), buserelin Acetate (Suprefact®), cyproterone Acetate (Androcur®), degarelix Acetate (Firmagon®), enzalutamide (Xtandi®), flutamide (Euflex®), goserelin Acetate (Zoladex®), histrelin Acetate (Vantas®), leuprolide Acetate (Lupron®, Eligard®), triptorelin Pamoate (Trelstar®). The therapy can also include drugs to treat bone metastases (bisphosphate therapy), such as alendronate (Fosamax®), denosumab (Xgeva®), pamidronate (Aredia®), zoledronic acid (Zometa®), or radiopharmaceuticals, such as radium 223 (Xofigo®), strontium-89 (Metastron®), and samarium-153 (Quadramet®).

The therapy can be administered in cycles (such as 1 to 6 cycles), with a period of treatment (usually 1 to 3 days) followed by a rest period. But some therapies can be administered every day.

Example 1

Methods and Materials

This example provides technical details and procedures, including relevant instrument settings and materials, used to obtain the protein expression data from patient urine samples discussed in the Examples below.

Urine Collection, Processing, and Protein Digestion

Use of human urine samples was approved by an Institutional Review Boards with written consent of donors, and the samples were anonymized before being given to researchers. The suffix N was added to the sample codes to denote non-cancer, and the suffix C to denote cancer from pre-operative (pre-op) patients. Urine from post-operative patients (post-op) was collected after surgical resection of the prostate. All urine samples were freshly collected for this study; no archived samples were used.

Collected voided urine samples were processed within 2 h (to isolate RNA as well). The samples were centrifuged at 1,200 rpm for 5 min, and the supernatant was stored at −80° C. Fifteen to 100 mL of urine was desalted and concentrated using Amicon® Ultra-15 (3 kDa molecular weight cut-off, Millipore, USA). Protein concentrations were determined by the BCA assay (Pierce, USA). Concentrated urinary proteins from each sample, ranging from 200 to 300 µg, were denatured and reduced with 8 M urea and 10 mM DTT in 50 mM $NH_4HCO_3$, pH 8.0 for 1 h at 37° C. Protein cysteine residues were alkylated with 40 mM iodoacetamide for 1 h at room temperature in the dark. The resulting sample was diluted 6-fold with 50 mM $NH_4HCO_3$, pH 8.0, and digested by sequencing-grade modified porcine trypsin (Promega, USA) at 1:50 trypsin:protein (w/w) overnight at 37° C. The resulting digest was desalted by using a 1 mL SPE C18 column (Supelco, USA) as described previously (Shi et al., J Proteome Res 13:875-82, 2014). The final tryptic peptide concentration was determined by the BCA assay. The peptide sample was diluted to 0.5 µg/µL with 0.1% formic acid in water, and heavy isotope-labeled synthetic peptides were spiked in at an equimolar concentration, 10 fmol/µt of crude heavy peptides for the secreted protein markers, 10 fmol/µt of pure heavy peptide IVGGWECcamEK (Ccam: cysteine residue synthesized as carbamidomethyl cysteine), and 1 fmol/µt of pure heavy peptide LSEPAELTDAVK for PSA, due to the response difference between the two PSA peptides.

Database Query

The human urine proteome databases archived in PeptideAtlas (www.peptideatlas.org) were queried for data entries of marker identifiers. The UrinePA build contained high confidence peptide and protein identifications obtained from five labs using tandem mass spectrometry proteomics (Farrah et al., J Proteome Res 13:60-75, 2014). About 2,500 non-redundant proteins were cataloged at a 1% false discovery rate. Another database listed 587 entries of a "Core Urinary Proteome", which was established from an in-depth analysis of second morning urine obtained over three days from seven healthy volunteers between 25-35 years old (Nagaraj and Mann, J Proteome Res 10:637-45, 2011).

Chemical Reagents

Urea, dithiothreitol (DTT), iodoacetamide, ammonium formate, trifluoroacetic acid (TFA), and formic acid were purchased from Sigma (USA). The synthetic peptides labeled with $^{13}C/^{15}N$ on C-terminal lysine and arginine residues were from Thermo Scientific (USA). The heavy peptides for PSA protein were estimated to be of >95% purity by HPLC.

SRM Assays

Ten surrogate peptides were first chosen for the protein markers based on in silico trypsin digestion and existing MS/MS data, the Global Proteome Machine (GPM), and PeptideAtlas. These peptides were then evaluated by ESP predictor (Fusaro et al., Nat Biotechnol 27:190-8, 2009) and CONSeQuence software (Eyers et al., Mol Cell Proteomics 10:M110.003384, 2011). Three to five peptides with moderate hydrophobicity and high scores from the prediction tools were selected for peptide synthesis. The synthesized crude heavy-isotope labeled peptides were further evaluated for peptide response and fragmentation pattern. Optimal collision energy (CE) values were achieved by direct infusion of the individual peptides and/or multiple LC-SRM runs with CE ramping. The best performing peptides were used for detection and quantification of the secreted protein markers. For each peptide, the three best transitions and matrix interference were determined. The relative intensity ratios among the three selected transitions for SRM were predefined by the internal standard heavy peptides in buffer. The matrix interference for a given transition that fell into mass widths Q1 and Q3 from co-eluting peptides was identified by a deviation from the expected relative intensity ratios among the transitions. The transition with no matrix interference was used for marker quantification in urine samples.

LG-SRM Measurement

The LG-SRM approach was previously demonstrated to enable reproducible quantification of target proteins at ~10 ng/mL levels in nondepleted human serum (Shi et al., Anal Chem 85:9196-203, 2013). Typically, 4 µL of the tryptic digest samples with a peptide concentration of 0.5 µg/µL was directly loaded onto a capillary reversed-phase column, 75 µm inner diameter (i.d.)×150 cm length, packed in-house with 3-µm Jupiter C18 bonded particles (Phenomenex, USA) to permit long gradient separation without a trap column with its dead volume affecting peptide retention time. Peptide separations were performed at a mobile phase flow rate of 100 nL/min on a binary pump system using 0.1% formic acid in water as phase A and 0.1% formic acid in 90% acetonitrile as phase B. The profile for a 300-min gradient time was 5-15% B in 27 min, 15-25% B in 140 min, 25-35% B in 73 min, and 35-90% B in 60 min. The TSQ Vantage mass spectrometer was operated in the manner as previously described (Shi et al., Anal Chem 85:9196-203, 2013).

PRISM-SRM Measurement

The PRISM-SRM approach has been described for quantification of low-abundance proteins in human plasma or serum (Shi et al., Proc Natl Acad Sci USA 109:15395-400, 2012). Briefly, high-resolution reversed-phase capillary LC with pH 10 mobile phase was used as the first dimensional separation of peptides from trypsin-digested human urine proteins. Following separation, the column eluent was automatically collected every minute into a 96-well plate during a ~100-min LC run while on-line SRM monitoring of heavy internal standard peptides was performed on a small split stream of the flow. Intelligent selection (termed iSelection) of target peptide fractions was achieved based on the on-line SRM signal of internal standard peptides. Prior to peptide fraction collection, 17 µL of water was added to each well to minimize excessive loss of peptides and dilute the peptide fractions (~1:7) for LC-SRM analysis.

Following iSelection, the target peptide-containing fractions were subjected to LC-SRM measurement. All peptide fractions were analyzed by using the nanoACQUITY UPLC® system (Waters Corporation, USA) coupled on-line to a TSQ Vantage triple quadrupole mass spectrometer (Thermo Scientific). Solvents used were 0.1% formic acid in water (mobile phase A) and 0.1% formic acid in 90% acetonitrile (mobile phase B). Peptide separations were performed at a mobile phase flow rate of 400 nL/min using an ACQUITY UPLC BEH 1.7 µm C18 column (75 µm i.d.×10 cm), which was connected to a chemically etched 20 µm i.d. fused-silica emitter via a Valco stainless steel union. Four microliters of individual peptide fractions (total volume 20 µL) following PRISM were injected for LC separation using a binary gradient of 10-20% phase B in 7 min, 20-25% phase B in 17 min, 25-40% phase B in 1.5 min, 40-95% phase B in 2.5 min, and 95% phase B in 6 min for a total time of ~35 min. The TSQ Vantage was operated in the same manner as described (Shi et al., J Proteome Res 13:875-82, 2014). A scan width of 0.002 m/z and a dwell time of 40 ms were set for all SRM transitions.

Proteomics Data Analysis

SRM data were analyzed using Skyline software (MacLean et al., Bioinformatics 26:966-8, 2010). Peak detection and integration were determined based on two criteria: (1) the same retention time and (2) approximately the same relative SRM peak intensity ratios across multiple transitions between light (L) peptides and heavy (H) peptide standards (Shi et al., J Proteome Res 13:875-82, 2014; Shi et al., J Proteome Res12:3353-61, 2013]. All data were manually inspected to ensure correct peak detection and accurate integration. The signal to noise ratio (S/N) was calculated by the peak apex intensity over the highest background noise in a retention time region of ±15 s for the target peptides (Shi et al., Proc Natl Acad Sci USA 109: 15395-400, 2012; Shi et al., J Proteome Res 12:3353-61, 2013). The background noise levels were conservatively estimated by visually inspecting chromatographic peak regions. Quantifiable endogenous surrogate peptides should have SRM signals with S/N≥10. The RAW data from the TSQ Vantage were loaded into Skyline to create high resolution figures of extracted ion chromatograms (XICs) of multiple transitions monitored for the target peptides/proteins.

Statistical Analysis

GraphPad Prism 6.0 was used for statistical analysis and plotting; P<0.05 was considered statistically significant. Receiver operating characteristic (ROC) curves were produced in terms of sensitivity and specificity of protein markers at their specific cutoff values. The optimal cutoff was the point with the best sum of sensitivity and specificity. Multivariate evaluative analysis for various combinations of protein markers was performed using SPSS 16 by logistic regression to find the best-fitting model for each comparison group.

AGR2 ELISA

Urinary AGR2 was measured by a developed sandwich ELISA based on monoclonal antibodies P1G4 (IgG1) to capture and P3A5 (IgG2a) to detect as described (Wayner et al., Prostate 72:1023-34, 2012). Recombinant AGR2 (GenWay Biotech, San Diego, Calif.) was used to generate a standard curve. Purified P1G4 at 1:1,000 was used to capture the analyte, and purified P3A5 at 1:1,000 was used for detection followed by HRP-conjugated anti-mouse IgG2a (SouthernBiotech, USA). The chromogenic reaction was recorded at plate reader setting of λ=405 nm. Culture media of the AGR2-secreting prostate cancer cell line PC3 was used as a positive control. Buffer was the negative control.

Calculations

Secreted protein concentration calculation in urine (ng/100 μg of total urinary protein):

$$[\text{secreted protein}] = L/H \times IS(\text{fmol}/\mu L) \times MW \times 10^{-6} (\text{ng/fmol}) \times 200\ \mu L$$

IS: internal standard
MW: protein molecular weight (g/mol)
100 μg of urinary protein: 200 μL of 0.5 μg/μL urine peptide

Example 2

Tumor-Associated Secreted Proteins in Human Urine

This example describes methods that were used to determine the tumor-associated secreted proteins present in urine.

Through comparison of cell type-specific transcriptomes, genes showing elevated tumor expression and encoding secreted/extracellular proteins were identified from both the epithelial and stromal compartments. Furthermore, gene expression analysis indicated that many showed differential expression among tumors of different Gleason scores. The epithelial-derived marker candidates included AGR2, AGR3, CRISP3, CEACAM5, CEACAM6, CCL3, CCL4, IL24, and MMP9; the stromal-derived candidates included CXCL14, CD90, IL24, MMP9, POSTN, SFRP4, and WISP1. The database PeptideAtlas was interrogated to determine if these proteins were present in non-cancer urine. The query result is shown in FIG. 1. In the UrinePA archive of available mass spectrometry datasets, the "observed" qualifier was used to indicate protein abundance. UMOD and ALB were the most abundant with the observed times 24,115 and 33,149, respectively. Other proteins, such as APOD (2,352), LMAN2 (639), AMBP (15,223), F2 (1,164), PTGDS (4,479), and AZGP1 (1,903), were the major urinary proteins that could be visualized by staining of a polyacrylamide gel electrophoregram. Prostatic proteins, such as KLK3/PSA (193), KLK2 (2), ACPP (415), MSMB (21), PSCA (123), and PRSS8 (230), were also cataloged as was stromal cell PENK (6). ERG (0), a cytoplasmic protein in prostate cancer cells and endothelial cells, was not found. Non-secreted UPK3A (3) was present for bladder cells. A group of cell surface CD antigens expressed by luminal and cancer cells (CD26, CD10, CD57, CD38, CD107a, and CD107b) were also found. CD45 (0) was queried for leukocytes, and CD31 (9) for endothelial cells. Of the marker candidates, CRISP3 (65), CEACAM5 (21), CEACAM6 (5), THY1/CD90 (261), MMP9 (115), and SFRP4 (17) were cataloged in non-cancer, demonstrating that they could be detected in all urine samples. Therefore, those proteins that were not encountered in the database of healthy donors were more likely derived from diseased tissues, such as prostate cancer in the urinary system.

Example 3

Multiplexed Peptide Assays for Prostate Cancer Protein Markers

This example describes methods that were used to develop sensitive multiplexed peptide assays for prostate cancer-associated protein markers.

Figure 3B:
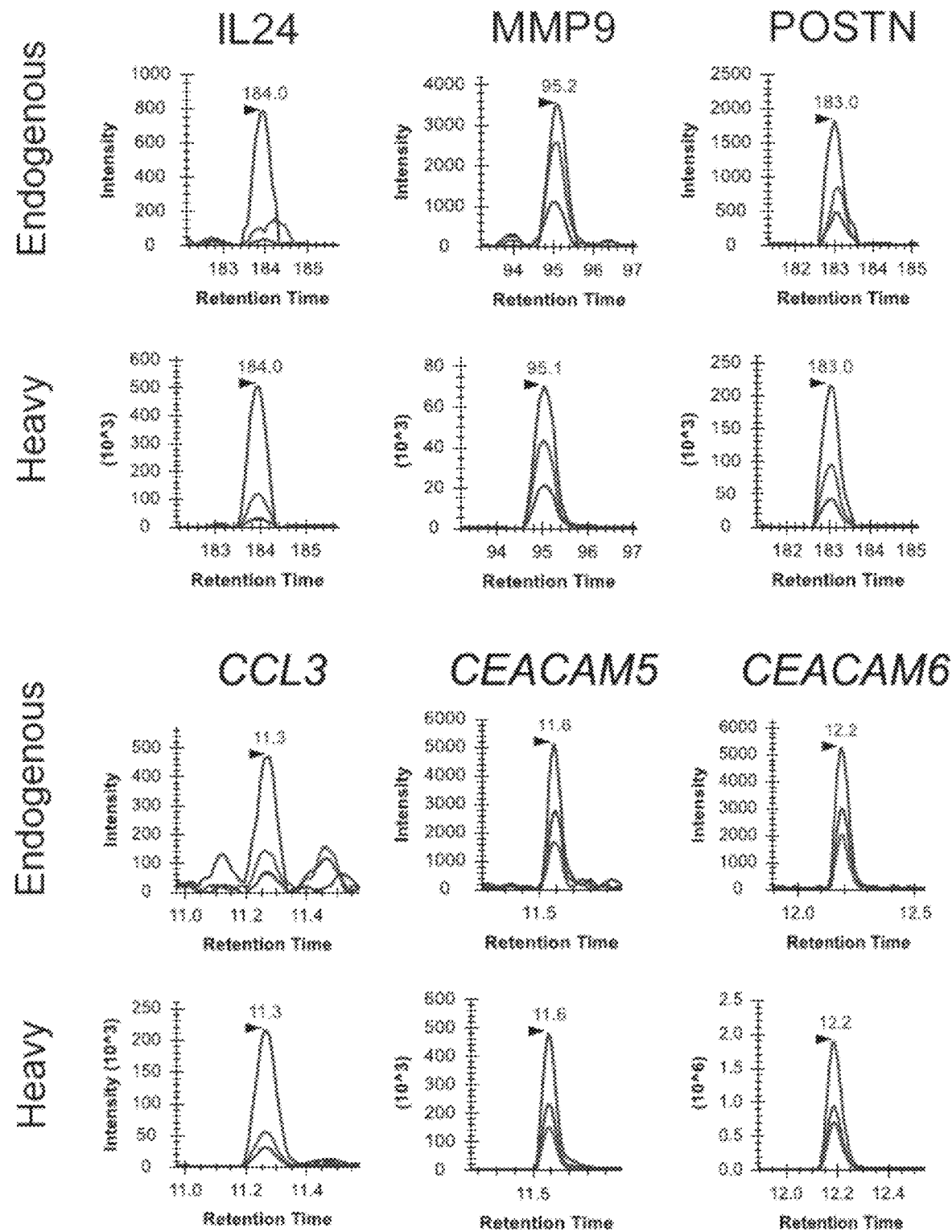
Figure 5D:
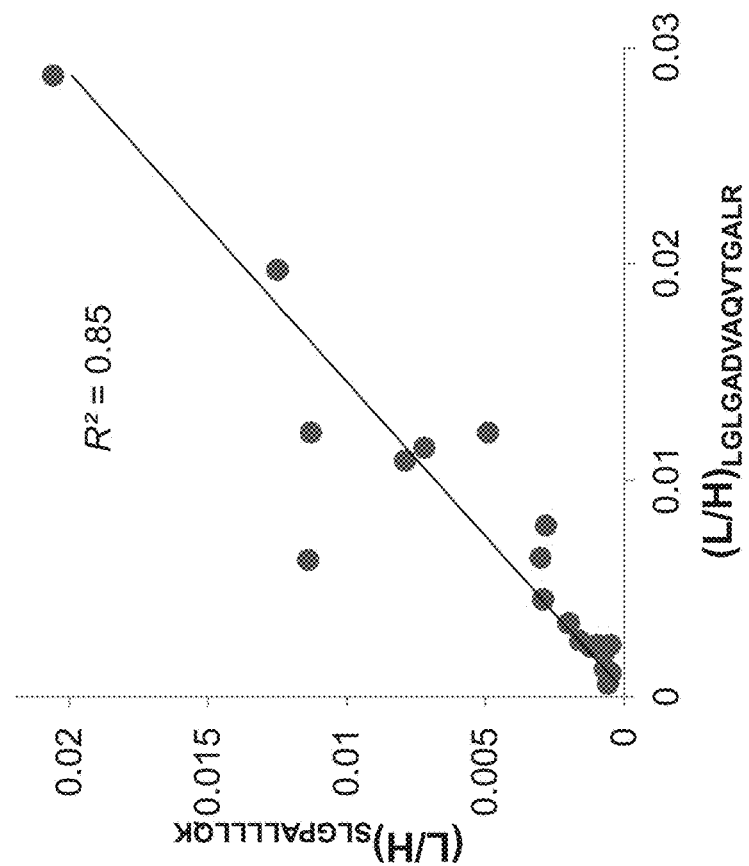
Figure 5C:
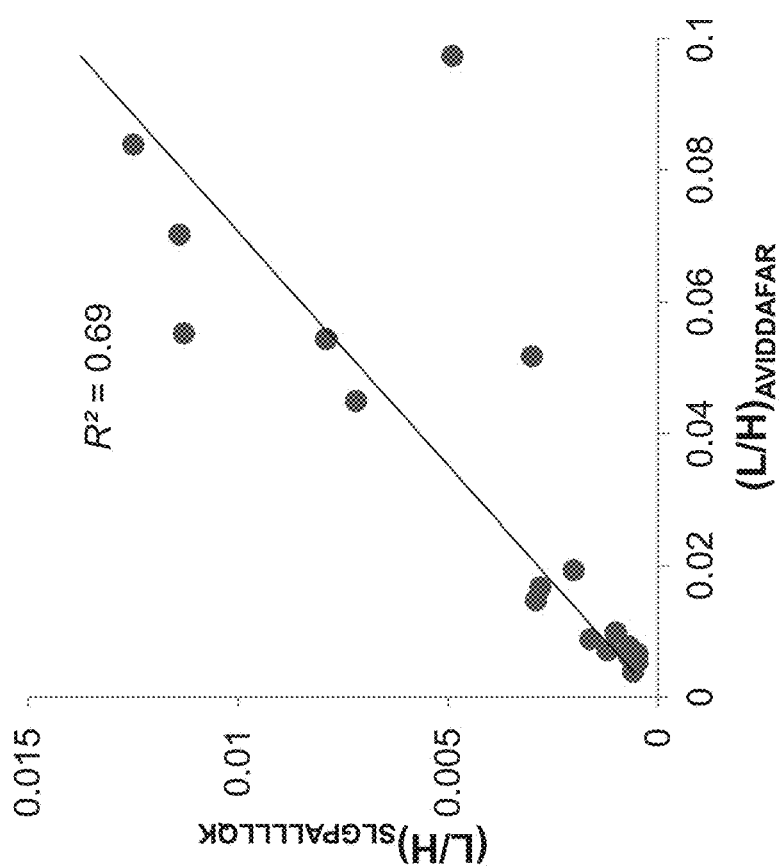
Figure 5E:
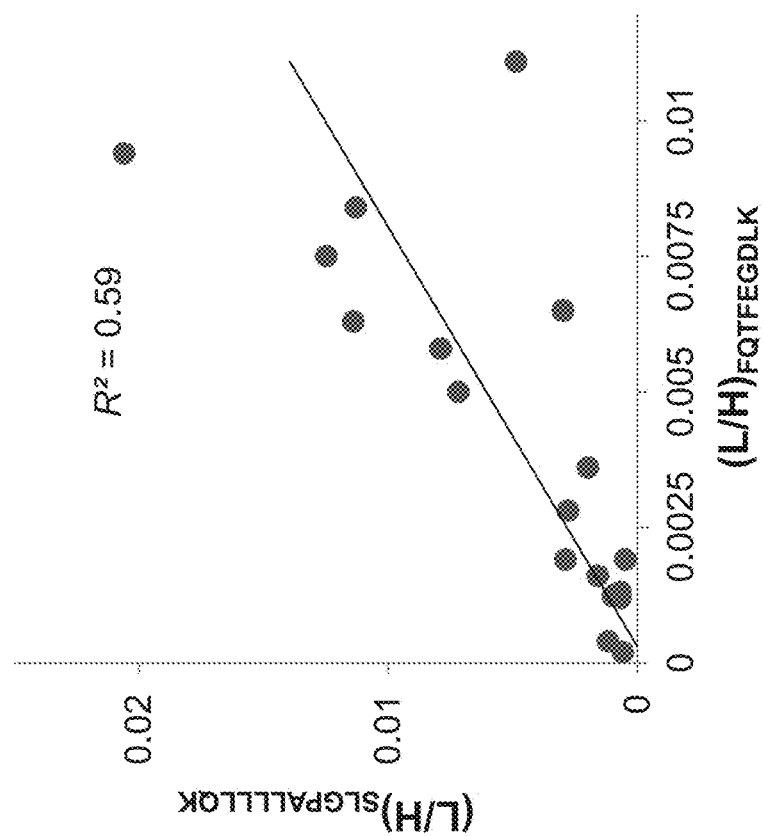
Figure 5F:
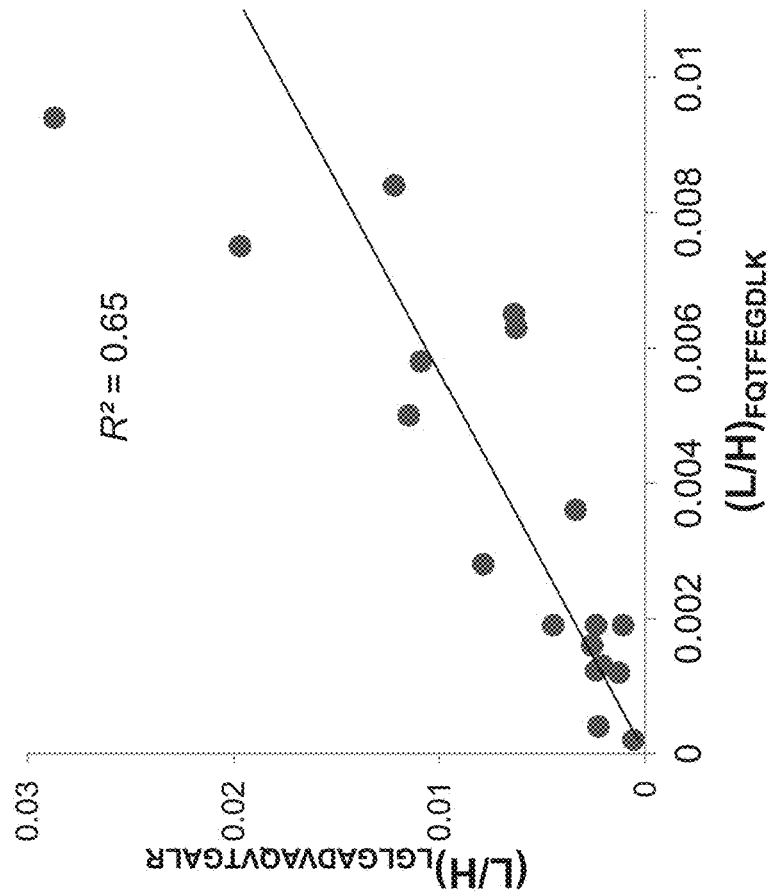

Selection of the most suitable surrogate peptides is important for sensitive accurate quantification of target proteins in patient specimens. For each prostate cancer protein marker, the surrogate peptides selected for assay development are listed in FIG. 2. For PSA, IVGGWECcamEK (SEQ ID NO: 70) and LSEPAELTDAVK (SEQ ID NO: 71) were demonstrated to be most effective for quantification (Shi et al., Proc Natl Acad Sci USA 109:15395-400, 2012; Keshishian et al., Mol Cell Proteomics 6:2212-29, 2007). For the others, a pooled prostate cancer patient urine sample was used to configure the final SRM assays with an evaluation of matrix interference, endogenous peptide detectability, and the peptide SRM response. LG-SRM was used first to simultaneously measure the 14 candidates due to its moderate sensitivity (≥10-fold higher than LC-SRM) and higher multiplexing capability (~three times higher than LC-SRM) (Shi et al. Anal Chem 85:9196-203, 2013). PSA, CD90 (THY1), CRISP3, CXCL14, IL24, MMP9, POSTN, and SFRP4 (note protein names of these genes, which could be different, are given in the figures), were confidently detected and quantified by at least one surrogate peptide (FIGS. 3A-3B and 4). The ultrasensitive PRISM-SRM (≥20-fold higher in sensitivity than LG-SRM) was then used to measure the other seven candidates. Five proteins, AGR2, AGR3, CCL3, CEACAM5, and CEACAM6, were reliably detected and quantified (FIGS. 3A-3B). The reproducibility of LG-SRM and PRISM-SRM based assays for measurements in biofluids such as urine and serum has been validated and typically exhibit a coefficient of variance (CV) <10%. Based on the LG-SRM and PRISM-SRM results, SRM assays were established for each of the detectable peptides with the three best transitions without matrix interference, and the best transition was used for quantification (FIG. 4). From the assay results, the 12 detected markers were grouped into seven moderate-to-low abundance proteins for LG-SRM analysis and five low abundance proteins for PRISM-SRM analysis. The two undetected proteins, CCL4 and WISP1, were excluded from further testing. The configured SRM assays were used for measuring the 12 protein biomarkers in a cohort of 14 cancer (pre-op) and 6 non-cancer (healthy control) urine samples. Among the 12 proteins, after excluding CCL4 and WISP1, the remaining 10 proteins can be reliably detected and quantified across the 20 urine subjects with at least one surrogate peptide without co-eluting interference. Another cohort of post-op urine samples was collected and analyzed separately to determine the origin of urinary PSA.

Example 4

Quantification Accuracy of Individual Surrogate Peptides

This example shows assessment of the quantification accuracy for individual surrogate peptides to determine which surrogate peptides are suitable for diagnosis.

Multiple surrogate peptides were tested for quantification of a specific protein in urine. Without posttranslational modifications or undocumented amino acid changes in the surrogate peptides, their measured concentrations should have a high degree of correlation across all samples because the surrogate peptide level was stoichiometric to that of their cognate protein (Worboys et al., Nat Methods 11:1041-4, 2014). With any changes in the peptide sequence, the level of the unmodified surrogate peptides would be lower, affecting accurate measurement of their corresponding proteins. For these differences, each surrogate peptide could potentially represent a distinctive signature with diagnostic value (Zhang et al., J Exp Med 210:191-203, 2013).

Figure 6A:
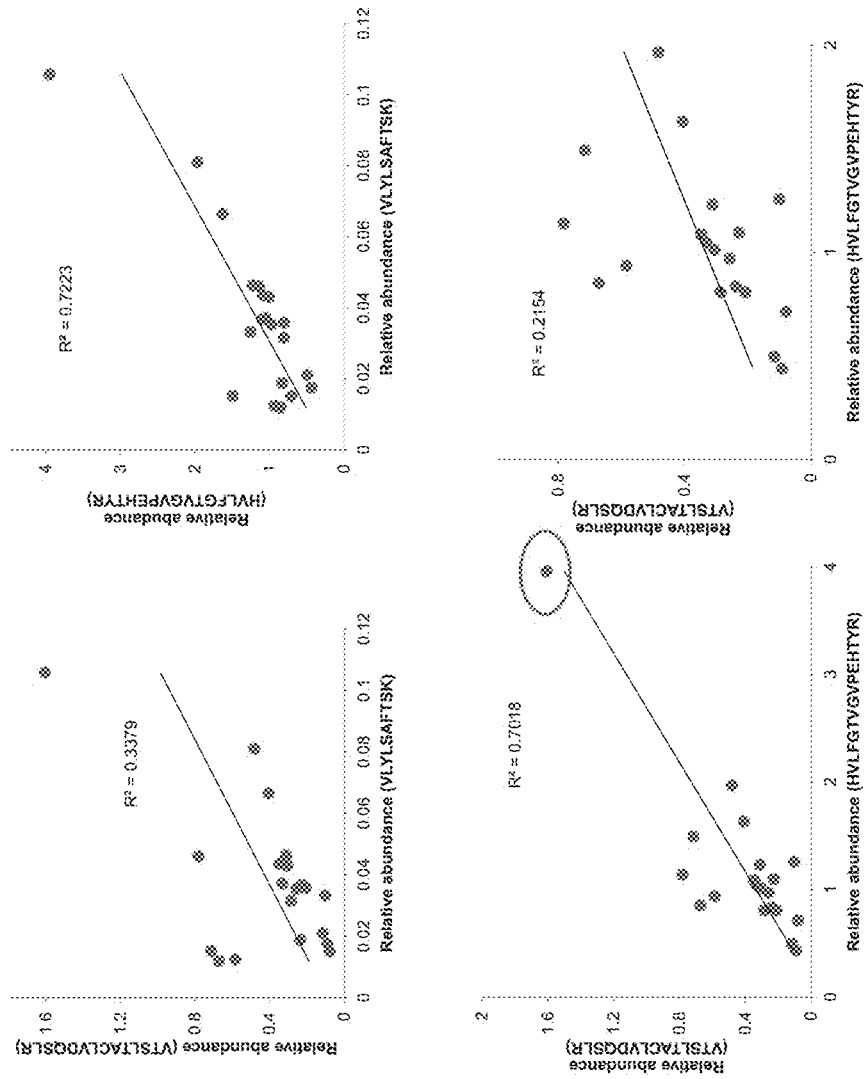
FIGS. 6A-6B show correlation curves between two surrogate peptides from the same protein.
Figure 6B:
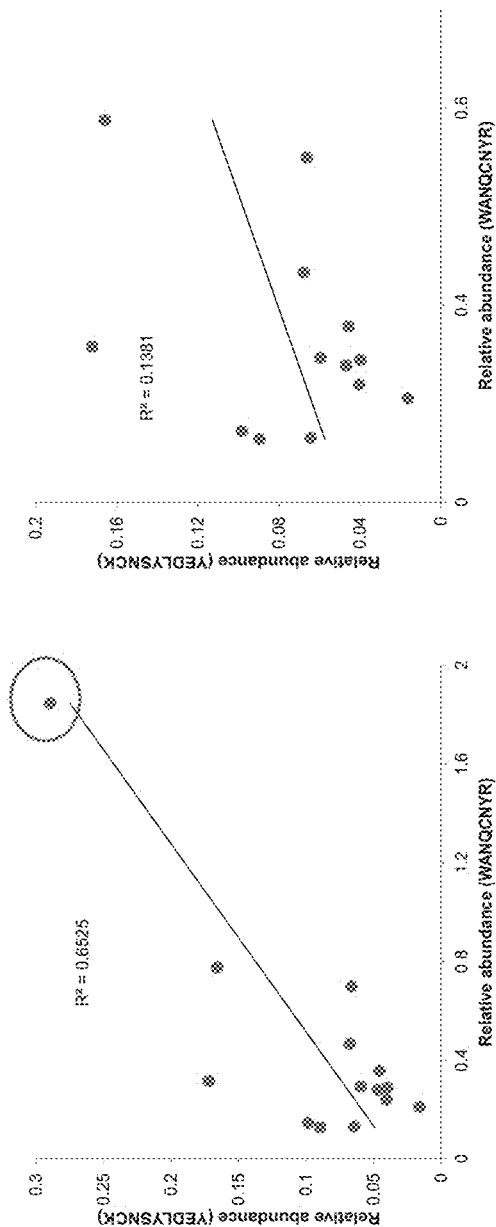

To evaluate the quantification accuracy of surrogate peptides, a correlation analysis of the L/H ratios between the surrogate peptides from the same protein was carried out. MMP9 was represented by four quantifiable surrogate peptides, and the Pearson correlation coefficients ranged from 0.59 between FQTFEGDLK (SEQ ID NO: 41) and SLGPALLLLQK (SEQ ID NO: 43) to 0.93 between AVIDDAFAR (SEQ ID NO: 40) and FQTFEGDLK (SEQ ID NO: 41), which indicated that multiple MMP9 isoforms could exist in these clinical urine samples (FIGS. 5A-5F). For CD90, low correlation coefficients between VTSLTACLVDQSLR (SEQ ID NO: 54) and the other two peptides were obtained, whereas a good correlation, $R^2$=0.72, was obtained with the other two peptides (FIGS. 6A-6B). These data show that unknown modifications were present in the VTSLTACLVDQSLR (SEQ ID NO: 54) sequence in several urine samples, making this peptide unsuitable for quantitative measurement of CD90. However, such modifications could be cancer-specific.

Figure 7A:
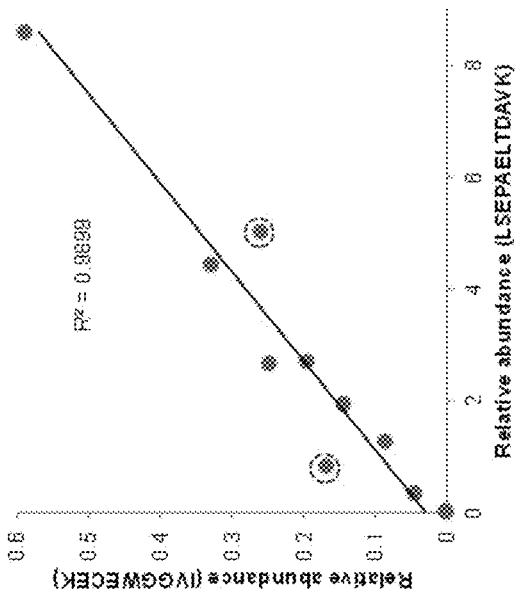
FIGS. 7A-7B show correlation curves between two PSA surrogate peptides in 20 urine subjects.
Figure 7B:
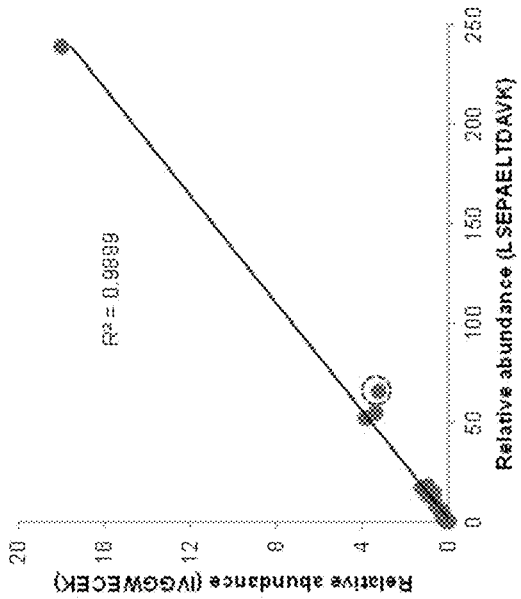
Figure 9:
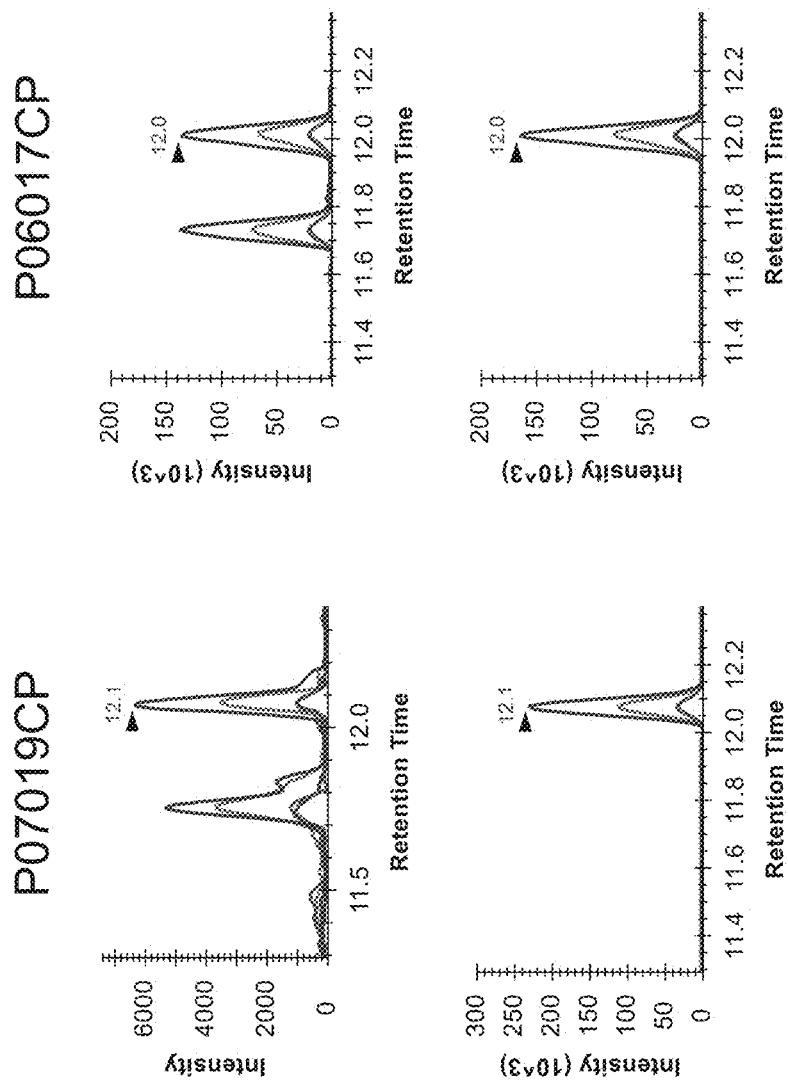
FIG. 9 shows extracted ion chromatograms of transitions monitored for the PSA peptide LSEPAE(L/I)TDAVK (SEQ ID NO: 71) in urine from two patients (for the two deviated data points on the correlation curve at the low concentration range in FIG. 7B).

A high correlation between the two widely used PSA peptides, IVGGWECcamEK (SEQ ID NO: 70) and LSEPAELTDAVK (SEQ ID NO: 71), was obtained with $R^2$=0.99 across the 20 urine samples (FIGS. 7A-7B). Closer examination revealed three data points from urine samples P08-015C, P07-040C, and P06-017C that deviated from the correlation plot (FIGS. 7A-7B and FIG. 8). These data show that the two PSA peptides in these urine samples contained amino acid alterations. For example, the P06-017C urine showed a lower L/H ratio for LSEPAELTDAVK (SEQ ID NO: 71). The experimental results indicate an amino acid change in the LSEPAELTDAVK sequence (FIG. 9; SEQ ID NO: 71). These data are supported by a recent discovery of PSA proteoforms, a nonsynonymous mutation L132I (rs2003783) within LSEPAE(L/I)TDAVK (SEQ ID NO: 71) (Végvári et al., Mol Cell Proteomics 12:2761-73, 2013). For the other two urine samples with the lower L/H ratios for IVGGWECcamEK (SEQ ID NO: 70), a similar type of change or others could be present (Mikolajczyk et al., Urology 59:797-802, 2002).

Example 5

Urinary PSA Exclusively Secreted by the Prostate Gland

This example shows that urinary PSA is primarily secreted by the prostate gland and that its secretion from other sources is negligible.

To quantitatively evaluate the percentage of urinary PSA originating from the prostate gland, LC-SRM was used to measure its concentration in seven post-op urine samples (i.e., from men without a prostate) and the cohort of 20 urine samples before radical prostatectomy (FIG. 8). The measured PSA levels ranged from 0.02 ng/100 µg to 2.95 ng/100 µg of total urinary protein with an average value of 0.98 ng/100 µg (and a median value of 0.41 ng/100 µg, FIG. 10). When compared to the PSA levels in the non-cancer and cancer samples with an average value of 110.89 ng/100 µg of total urinary protein (and a median value of 28.68 ng/100 µg), the percentage of PSA in the post-op urine was only ~1% (~1.5% median value, FIG. 10). In non-cancer and cancer, urinary PSA can be contributed by all possible sources, whereas in post-op, it cannot be contributed from an absent prostate gland. Thus, the data show that urinary PSA is secreted mostly from the prostate gland, and contribution from other sources in the urinary system is negligible.

Example 6

Normalizing the Concentration of Cancer-Associated Proteins Secreted Using PSA

This example shows normalization of cancer-associated secreted protein concentration using PSA to facilitate differentiation of cancer and non-cancer samples.

In the SRM targeted measurement, the reported L/H peak area ratios of surrogate peptides were proportional to the concentrations of their cognate protein and are expressed as ng/100 µg of total urinary protein because the same amount of the heavy internal standards was added to the digested peptide mixtures for all 20 samples, which have the same peptide concentrations. Thus, the L/H ratio is the adjusted concentration of the target protein in urine (against the total amount of the urinary proteins, Shi et al., J Proteome Res 13:875-82, 2014, FIGS. 11A-11B). This adjustment accounts for substantial variations in urinary protein concentration among donors and sometimes among donations from the same donor. For most surrogate peptides measured, the cancer urine showed higher median L/H values than the non-cancer urine; while for several other peptides (CRISP3, CXCL14, IL24, and SFRP4), a lower or equal median L/H value in cancer vs. non-cancer was found. A Mann-Whitney U test of the surrogate peptide L/H ratios revealed no significant difference between cancer and non-cancer for all of the secreted protein markers (FIG. 12). Because the secreted urinary proteome is a pool comprised of all proteins produced by organs along the urinary tract (see PeptideAtlas query result), "normalization" to the secreted proteins solely produced by the prostate was necessary. The post-op urine analysis showed that PSA levels, which were proportional to the size of the gland and the number of secretory cells, luminal and cancer, can be used for this normalization. PSA normalization was used to present urinary AGR2 levels as AGR2/PSA ratios (Shi et al., J Proteome Res 13:875-82, 2014). The amount of PSA was similarly used in the urine PCA3 assay in which the urinary PCA3 score was generated by normalizing the PCA3 transcript levels to those of PSA transcript (Marks and Bostwick, Rev Urol 10:175-81, 2008).

Based on the above peptide correlation analysis, both PSA peptides could be used to determine PSA protein concentrations in the cohort. The secreted protein marker/PSA concentration ratios were obtained by dividing the L/H peak area ratios of surrogate peptides for the protein markers by the L/H peak area ratio of the PSA peptide IVGGWECcamEK (SEQ ID NO: 70) (FIGS. 13A-13B). After PSA normalization, a significant difference between the cancer and non-cancer urine was observed for the marker peptides [except for LPQTLSR (SEQ ID NO: 3) of AGR2 (see below), VTSLTACLVDQSLR (SEQ ID NO: 54) of CD90, and MVIITTK (SEQ ID NO: 47) of CXCL14] with the P values ranging from 0.015 to 0.035 (FIG. 12 and FIGS. 14A-14F). These results demonstrate the utility of PSA protein normalization in prostate cancer urine biomarker performance.

Figure 14A:
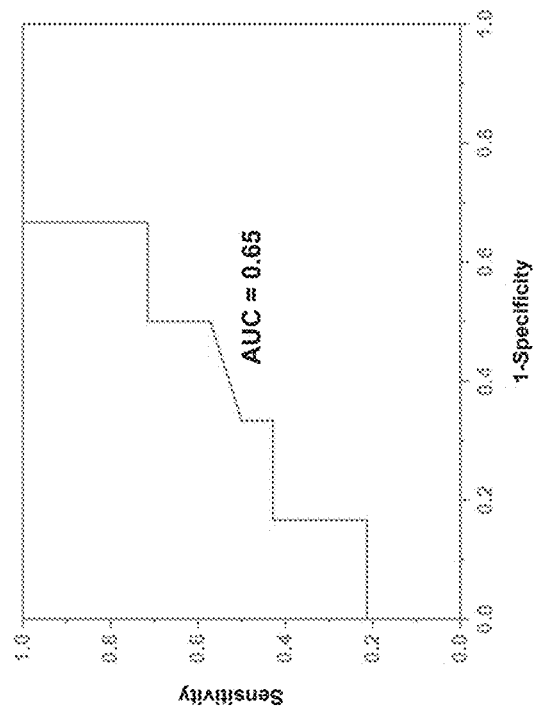
FIGS. 14A-14F show urine protein biomarkers for prostate cancer.
Figure 14B:
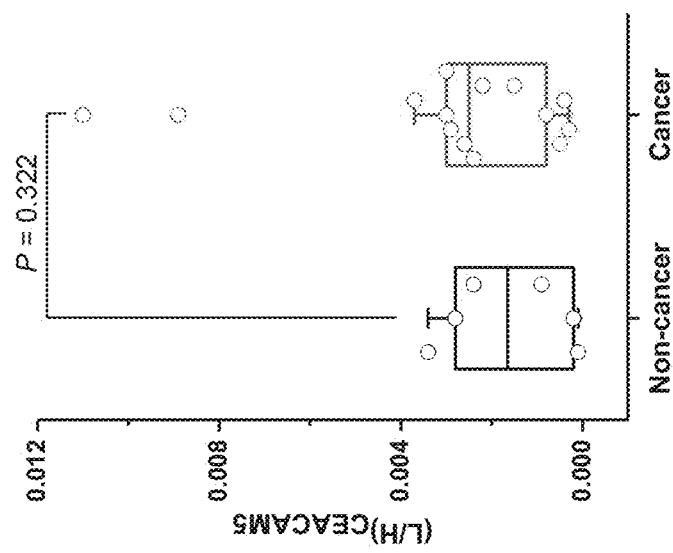
Figure 14D:
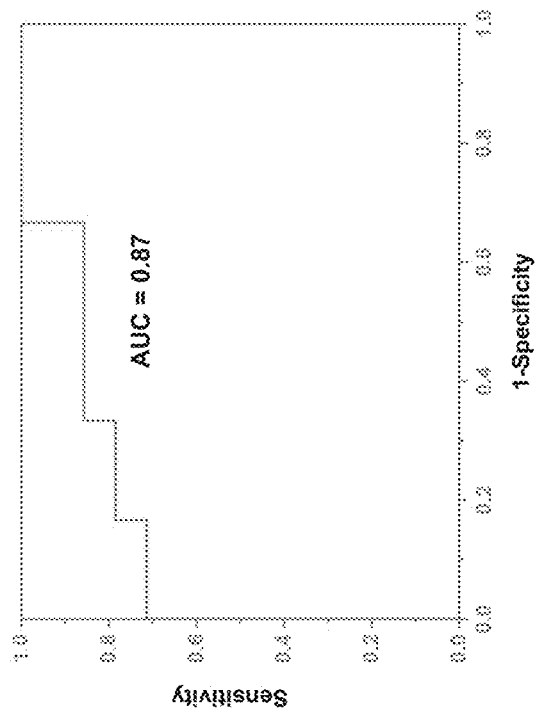
Figure 14C:
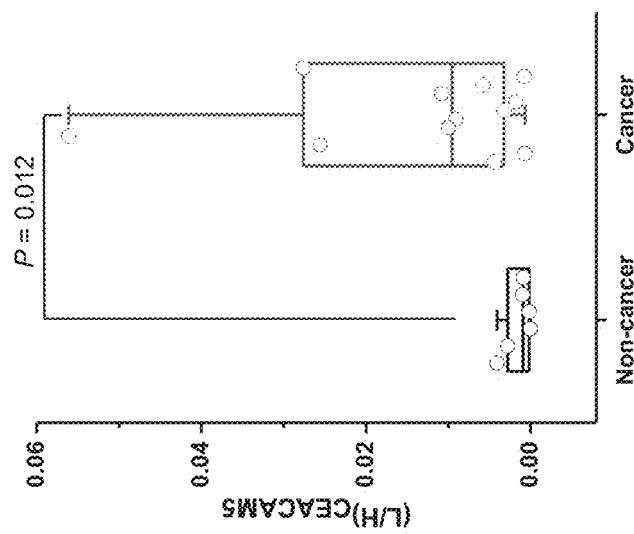
Figure 14E:
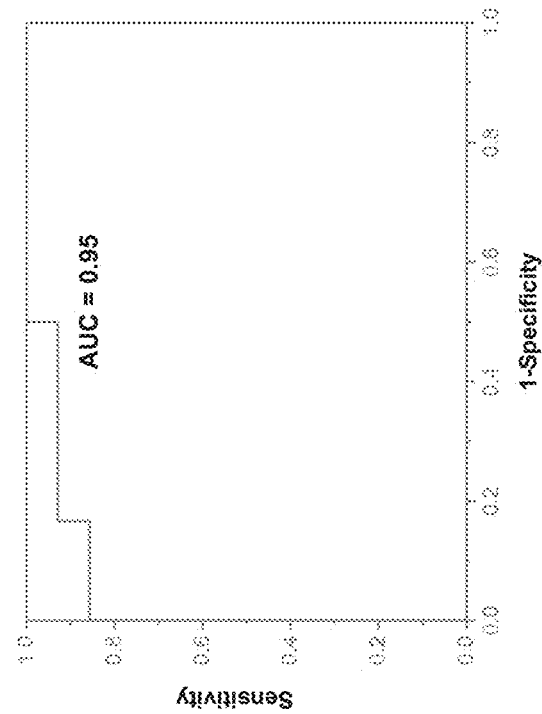
Figure 14F:
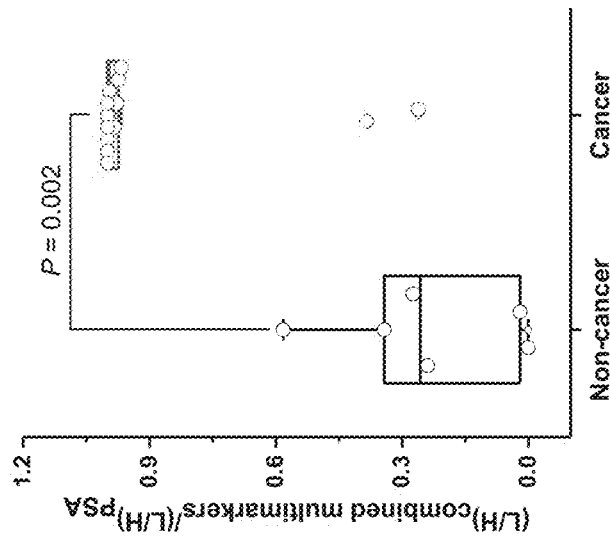

ROC analyses with 95% confidence intervals show that the peptides with P<0.05 produced AUC values>0.80, while for the three peptides with P>0.05, the AUC values produced were <0.80 (FIG. 12 and FIGS. 14A-14B). With PSA normalization, all the peptide signatures showed values of the sum of sensitivity and specificity ranging from 1.60 to 1.79 at the optimal cutoff points. These data show good biomarker performance in differentiation of prostate cancer from non-cancer through urine analysis. In addition, surrogate peptides with a good correlation produced the same AUC values. For example, the AUC values obtained from the four MMP9 surrogate peptides, AVIDDAFAR (SEQ ID NO: 40), FQTFEGDLK (SEQ ID NO: 41), LGLGADVAQVTGALR (SEQ ID NO: 42), and SLGPALLLLQK (SEQ ID NO: 43), were 0.82, 0.86, 0.86, and 0.86, respectively. The AUC values from the two well-correlated CD90 surrogate peptides, VLYLSAFTSK (SEQ ID NO: 53) and HVLFGTVGVPEHTYR (SEQ ID NO: 55), were 0.86 and 0.87, respectively. The VTSLTACLVDQSLR peptide (SEQ ID NO: 54) without significant correlations produced an AUC value of 0.77 (FIG. 12). Multi-marker performance was also assessed by using a multivariate analysis of various combinations of the surrogate peptides (FIG. 15). The best combination consisted of LPQTLSR (SEQ ID NO: 3) from AGR2, LYTYEPR (SEQ ID NO: 6) from AGR3, SDLVNEEATGQFR (SEQ ID NO: 23) from CEACAM5, VTSLTACLVDQSLR (SEQ ID NO: 54) from CD90, and GVCISPEAIVTDLPEDVK (SEQ ID NO: 64) from SFRP4. With a P value of 0.002 and an AUC value of 0.95, this peptide grouping outperformed any single marker (FIGS. 14E-14F, FIG. 12, and FIG. 15).

Example 7

Transient Increase in Urinary AGR2 in Non-Cancer Urine

This example demonstrates transient increases in urinary AGR2 in non-cancer urine and a persistently high urinary AGR2 in cancer urine.

Figure 16A:
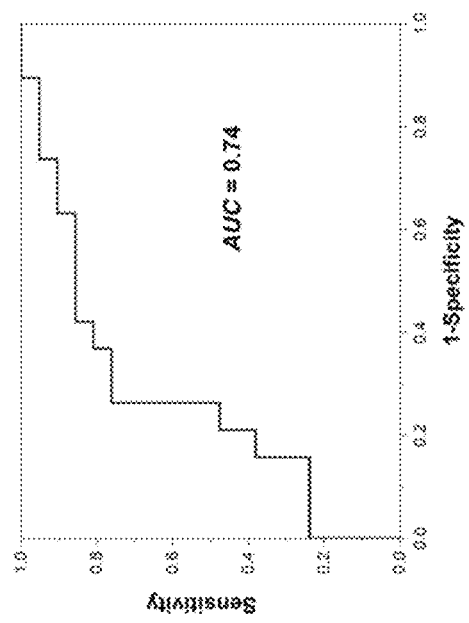
FIGS. 16A-16B show urinary AGR2 measured by ELISA.
Figure 16B:
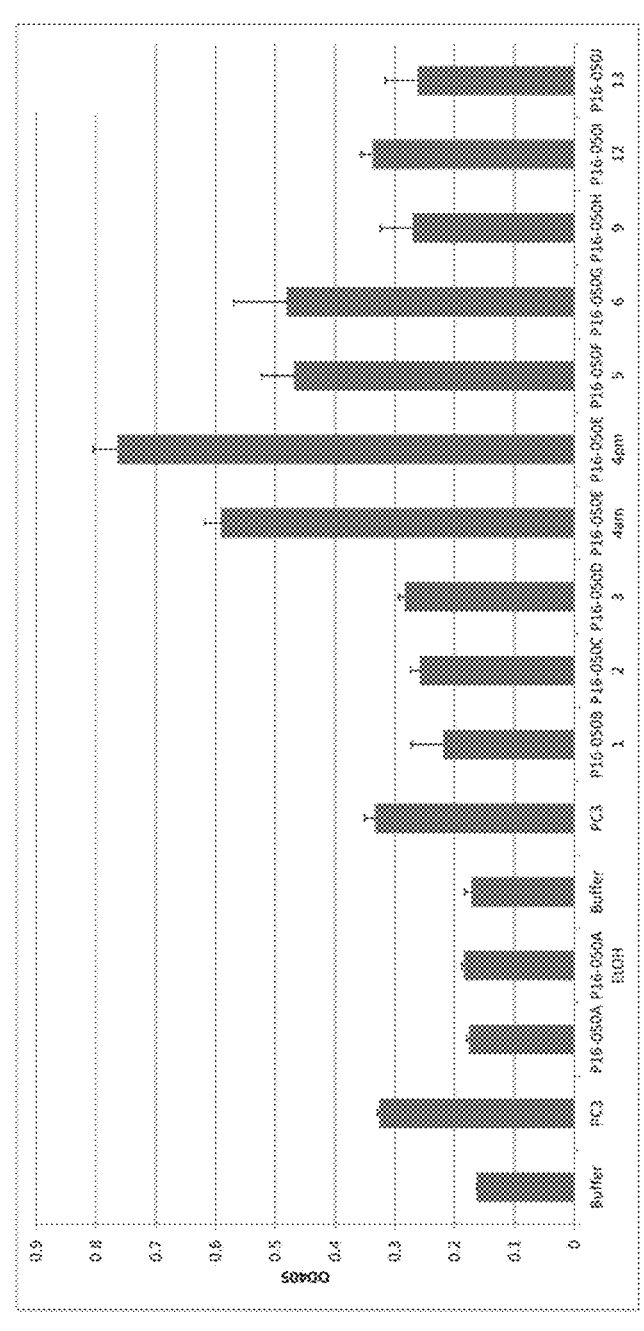

A fraction of non-cancer urine was found to have an above-background amount of urinary AGR2, although urine proteome database query yielded no AGR2 identifier (cf. FIG. 1). The AGR2 levels in a middle-age non-cancer male (with normal serum PSA (sPSA)) over a two-week period are shown in FIG. 16B. The levels increased on day 4 (for both morning and afternoon urine) followed by a decrease to the baseline level on subsequent days. Treatment of urine samples by the addition of alcohol (to lyse shed AGR2$^+$ bladder cells) did not raise the level of detectable urinary AGR2 (bars 3 vs. 4, FIG. 16B). Thus, some day-to-day physiological differences could account for AGR2 in the urine of non-cancer samples. This phenomenon affected the AUC for AGR2. Unlike non-cancer samples, AGR2 in cancer urine samples remained above the background, and the urine contained other marker proteins. Testing this hypothesis required a suitable patient donor to volunteer donations every day over a similar period of two weeks. Nevertheless, the AUC value obtained for AGR2 was 0.74 (FIG. 16A) by ELISA and 0.77 by PRISM-SRM. Hence, both biomarker measurement methods produced concordant results.

Example 8

Detection of Clinically Significant Cancers by Secreted Protein Markers

This example compares differentiative power in identifying the low-risk from the high-risk cancers among secreted protein markers. This example also shows that MMP9 expression can be used to differentiate low- and high-risk prostate cancer.

Figure 19A:
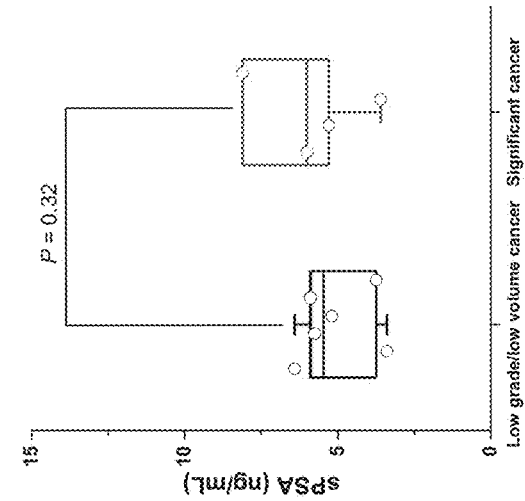
FIGS. 19A-19C show stratification of prostate cancer based on tumor volume and Gleason score.
Figure 19B:
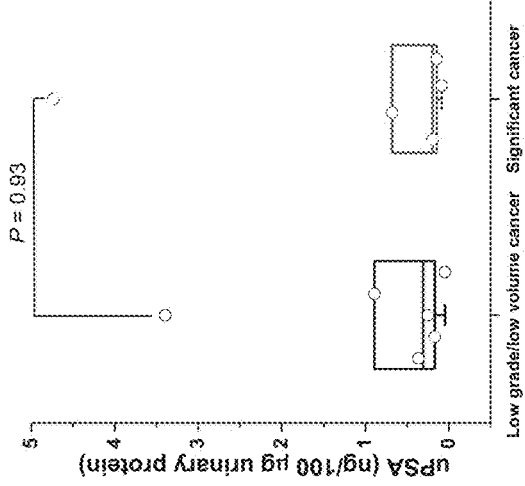
Figure 19C:
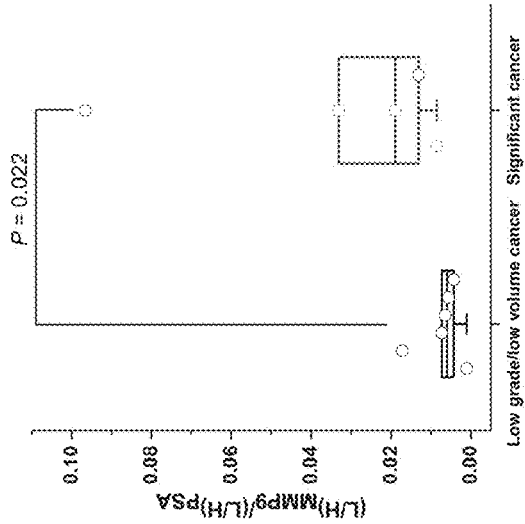
Figure 20A:
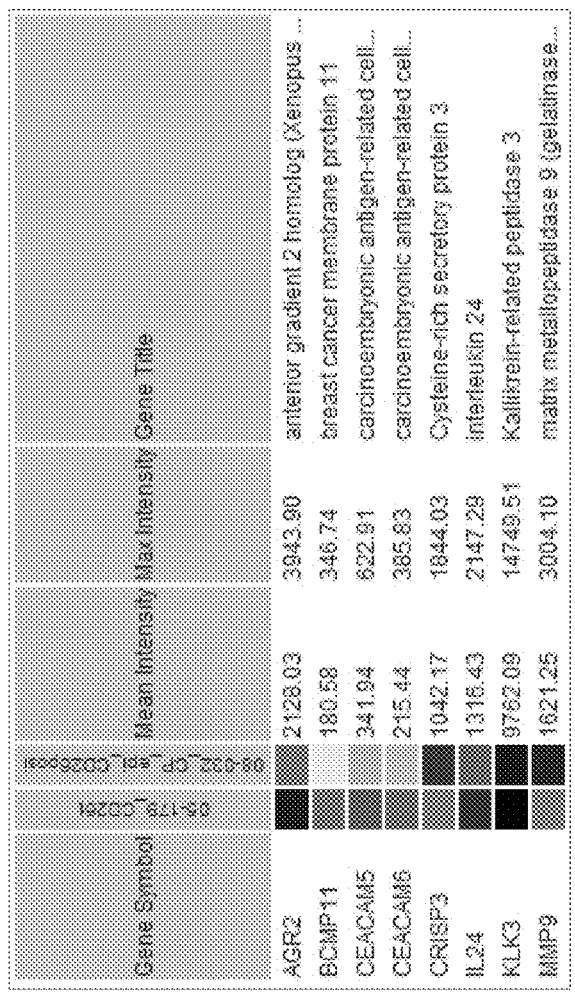
FIGS. 20A-20B show gene expression levels of protein markers in Gleason 3 (labeled 05-179_CD26t) vs. Gleason 4 (labeled 08-032_CP_epi_CD26posi) cancer cells. Differential expression is displayed using gray scale (FIG. 20A) and histogram (FIG. 20B) formats.
Figure 20B:
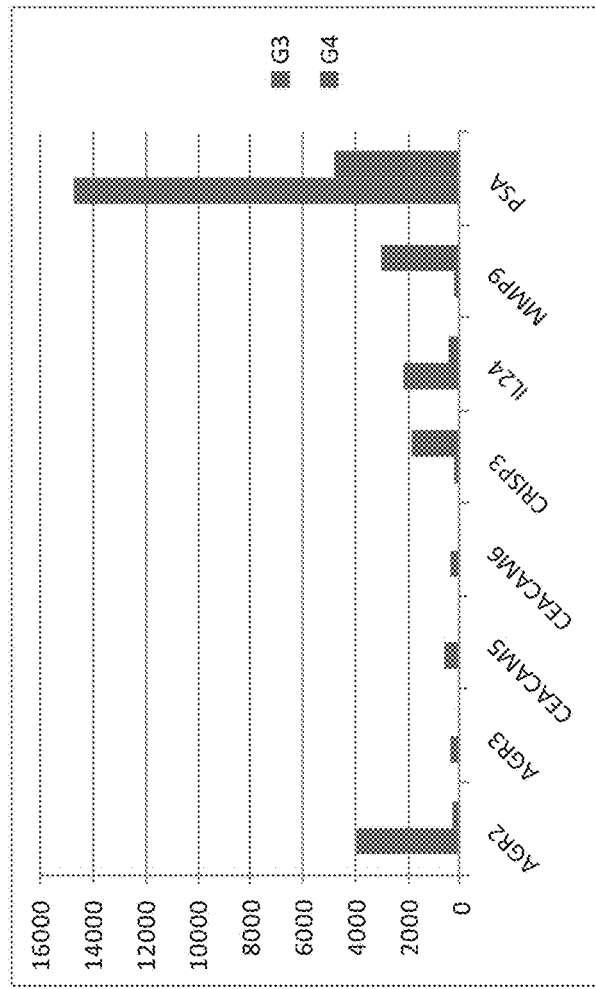

The prostate cancer cohort was grouped into either low volume/low grade: Gleason score≤6 and dominant tumor volume≤0.5 cc (Nakanishi et al., J Urol 179:1804-9, 2008) or clinically significant: not meeting the criteria for the low volume/low grade disease. The marker levels for low-risk cancer and high-risk cancer were analyzed by Mann-Whitney's U test (FIGS. 17 and 18A-18B). For most surrogate peptides, the marker/PSA ratios were lower in men with low volume/low grade than those with high volume/high grade; thus, more cancer-associated proteins were produced and secreted into urine from significant cancers. However, most surrogate peptides did not show a significant differentiative power in identifying the low-risk from the high-risk cancers (FIGS. 18A-18B). One exception was MMP9. Two surrogate peptides, FQTFEGDLK (SEQ ID NO: 41) and LGLGADVAQVTGALR (SEQ ID NO: 42), produced a P value of 0.022 in comparing low volume/low grade cancer and significant cancer (FIGS. 18A-18B and FIG. 19A). The AUC values obtained from an ROC analysis for the two MMP9 peptides were above 0.90; thus, MMP9 and Gleason and tumor volume were associated in this patient cohort. This result is supported by the dataset query of cancer cell type transcriptomes. The array signal intensity value for MMP9 in Gleason pattern 4 cancer cells is 3004.10, 12-fold higher than 238.41 in Gleason pattern 3 cancer cells. (FIGS. 20A-20B). Other secreted proteins, such as AGR2, showed lower array signal intensity values in Gleason 4 cancer cells than Gleason 3 cancer cells. For comparison, urine PSA and serum PSA showed no power in differentiating the two cancer types (FIGS. 19B-19C). This analysis was blinded because the pathology parameters were not made known before the quantitative SRM measurements.

In view of the many possible embodiments to which the principles of the disclosure may be applied, it should be recognized that illustrated embodiments are only examples of the disclosure and should not be considered a limitation on the scope of the invention. Rather, the scope of the invention is defined by the following claims. We therefore claim as our invention all that comes within the scope and spirit of these claims.

We claim:

1. A method of treating a subject with intermediate- or high-risk prostate cancer, comprising:
   measuring protein expression of MMP9 in a sample obtained from a subject, comprising measuring at least one surrogate peptide of MMP9, wherein the at least one surrogate peptide of MMP9 consists of SEQ ID NO: 41 or -SEQ ID NO: 42;
   measuring protein expression of PSA in the sample obtained from the subject;
   normalizing the protein expression of MMP9 to the protein expression of PSA in the sample from the subject;
   measuring increased protein expression of MMP9 normalized to PSA in the sample obtained from the subject as compared to a control representing protein expression of MMP9 normalized to PSA expected in a sample from a subject who has low-risk prostate cancer; and
   administering treatment for intermediate- or high-risk prostate cancer to the subject, thereby treating the subject, wherein high-, intermediate-, and low-risk prostate cancer is defined by Gleason scoring.

2. The method of claim 1, wherein the at least one surrogate peptide of MMP9 is measured using a mass spectrometry technique.

3. The method of claim 2, wherein the mass spectrometry technique is liquid chromatography-selected reaction monitoring (LC-SRM); long gradient-selected reaction monitoring (LG-SRM); or high-pressure, high-resolution separations, intelligent selection, multiplexing-selected reaction monitoring (PRISM-SRM).

4. The method of claim 1, wherein the at least one surrogate peptide of MMP9 protein is measured using an immunoassay.

5. The method of claim 4, wherein the immunoassay is an ELISA.

6. The method of claim 1, wherein normalizing to PSA protein expression comprises normalizing to at least one surrogate peptide of PSA.

7. The method of claim 6, wherein the at least one surrogate peptide of PSA comprises SEQ ID NO: 70 or SEQ ID NO: 71.

8. The method of claim 1, wherein the sample obtained from the subject is a urine sample.

9. The method of claim 1, wherein the measured protein expression of MMP9 has an AUC value of greater than 0.8.

10. The method of claim 1, wherein the measured protein expression of MMP9 has an AUC value of greater than 0.9.

11. The method of claim 1, wherein administering treatment for intermediate- or high-risk prostate cancer comprises administering surgery, radiation therapy, chemotherapy, or hormone therapy.

12. The method of claim 1, wherein the subject is human.

13. The method of claim 1, wherein Gleason scoring is used to determine high-, intermediate-, and low-risk prostate cancer.

14. The method of claim 1, wherein the high-risk prostate cancer is defined by a Gleason score greater than 7, the intermediate-risk prostate cancer is defined by a Gleason score of 7, and the low-risk prostate cancer is defined by a Gleason score less than or equal to 6.

15. A method of treating a subject with intermediate- or high-risk prostate cancer, comprising:
   measuring protein expression of MMP9 in a urine sample obtained from a subject, comprising measuring at least one surrogate peptide of MMP9, wherein the at least one surrogate peptide of MMP9 consists of SEQ ID NO: 41 or SEQ ID NO: 42;
   normalizing protein expression of MMP9 to PSA protein expression, wherein normalizing to PSA protein expression comprises normalizing to protein expression of at least one surrogate peptide of PSA;
   measuring increased protein expression of MMP9 normalized to PSA in the urine sample obtained from the subject as compared to a control representing protein expression of MMP9 normalized to PSA expected in a urine sample from a subject who has low-risk prostate cancer; and
   administering treatment for intermediate- or high-risk prostate cancer to the subject, thereby treating the subject, wherein high-, intermediate-, and low-risk prostate cancer is defined by Gleason scoring.

16. The method of claim 15, wherein Gleason scoring is used to determine high-, intermediate-, and low-risk prostate cancer.

17. The method of claim 15, wherein the high-risk prostate cancer is defined by a Gleason score greater than 7, the intermediate-risk prostate cancer is defined by a Gleason score of 7, and the low-risk prostate cancer is defined by a Gleason score less than or equal to 6.

* * * * *

UNITED STATES PATENT AND TRADEMARK OFFICE
CERTIFICATE OF CORRECTION

PATENT NO. : 10,725,053 B2
APPLICATION NO. : 15/839635
DATED : July 28, 2020
INVENTOR(S) : Qian et al.

Page 1 of 1

It is certified that error appears in the above-identified patent and that said Letters Patent is hereby corrected as shown below:

On the Title Page

<u>Item (57), In the Abstract:</u>
Line 8, "administering at therapy" should be --administering a therapy--.

In the Specification

Column 1, Line 40, "is the one of the" should be --is one of the--.

Column 20, Line 43, "are least at a" should be --are at least at a--.

Signed and Sealed this
Eighth Day of December, 2020

Andrei Iancu
*Director of the United States Patent and Trademark Office*